(12) United States Patent
Zhi

(10) Patent No.: US 11,970,482 B2
(45) Date of Patent: Apr. 30, 2024

(54) ACETAL COMPOUNDS AND THERAPEUTIC USES THEREOF

(71) Applicant: Ligand Pharmaceuticals Incorporated, San Diego, CA (US)

(72) Inventor: Lin Zhi, San Diego, CA (US)

(73) Assignee: LIGAND PHARMACEUTICALS INC., San Diego, CA (US)

( * ) Notice: Subject to any disclaimer, the term of this patent is extended or adjusted under 35 U.S.C. 154(b) by 461 days.

(21) Appl. No.: 16/960,681

(22) PCT Filed: Jan. 8, 2019

(86) PCT No.: PCT/US2019/012762
§ 371 (c)(1),
(2) Date: Jul. 8, 2020

(87) PCT Pub. No.: WO2019/139919
PCT Pub. Date: Jul. 18, 2019

(65) Prior Publication Data
US 2020/0339551 A1 Oct. 29, 2020

Related U.S. Application Data

(60) Provisional application No. 62/615,357, filed on Jan. 9, 2018.

(51) Int. Cl.
| | | |
|---|---|---|
| *C07D 405/14* | (2006.01) | |
| *C07D 239/42* | (2006.01) | |
| *C07D 405/06* | (2006.01) | |
| *A61K 31/397* | (2006.01) | |
| *A61K 45/06* | (2006.01) | |

(52) U.S. Cl.
CPC ......... *C07D 405/14* (2013.01); *C07D 239/42* (2013.01); *C07D 405/06* (2013.01); *A61K 31/397* (2013.01); *A61K 45/06* (2013.01)

(58) Field of Classification Search
CPC .. C07D 465/14; C07D 465/06; C07D 239/42; A61K 31/397; A61K 45/06
See application file for complete search history.

(56) References Cited

U.S. PATENT DOCUMENTS

| | | |
|---|---|---|
| 3,018,302 A | 1/1962 | Arnold et al. |
| 3,116,282 A | 12/1963 | Hunter |
| 3,328,388 A | 6/1967 | Shen et al. |
| 3,404,178 A | 10/1968 | Roy |
| 3,796,700 A | 3/1974 | Yoshioka et al. |
| 4,255,566 A | 3/1981 | Carrico et al. |
| 4,318,982 A | 3/1982 | Hornby et al. |
| 4,340,668 A | 7/1982 | Hornby et al. |
| 4,376,165 A | 3/1983 | Hornby et al. |
| 4,440,740 A | 4/1984 | Fix et al. |
| 4,447,529 A | 5/1984 | Greenquist et al. |
| 4,537,772 A | 8/1985 | Alexander et al. |
| 4,621,077 A | 11/1986 | Rosini et al. |
| 4,659,825 A | 4/1987 | Holy et al. |
| 4,692,441 A | 9/1987 | Alexander et al. |
| 4,705,651 A | 11/1987 | Staibano |
| 4,724,232 A | 2/1988 | Rideout et al. |
| 4,724,233 A | 2/1988 | DeClercq et al. |
| 4,729,989 A | 3/1988 | Alexander et al. |
| 4,731,360 A | 3/1988 | Alexander et al. |
| 4,749,694 A | 6/1988 | Fix et al. |
| 4,757,141 A | 7/1988 | Fung et al. |
| 4,777,163 A | 10/1988 | Bosies et al. |
| 4,804,655 A | 2/1989 | Müeller et al. |
| 4,808,716 A | 2/1989 | Holy et al. |
| 4,822,773 A | 4/1989 | Alexander et al. |
| 4,835,138 A | 5/1989 | Alexander et al. |
| 4,839,466 A | 6/1989 | Saltiel |
| 4,847,298 A | 7/1989 | Alexander et al. |
| 4,861,759 A | 8/1989 | Mitsuya et al. |
| 4,879,277 A | 11/1989 | Mitsuya et al. |
| 4,882,142 A | 11/1989 | Simon et al. |
| 4,898,724 A | 2/1990 | Simon et al. |
| 4,939,130 A | 7/1990 | Jaeggi et al. |
| 4,952,575 A | 8/1990 | Sauerbier et al. |
| 4,952,740 A | 8/1990 | Juge et al. |
| 4,963,525 A | 10/1990 | Alexander et al. |
| 4,963,556 A | 10/1990 | Alexander et al. |
| 4,973,579 A | 11/1990 | Alexander et al. |
| 5,034,394 A | 7/1991 | Daluge |
| 5,047,533 A | 9/1991 | Reist et al. |
| 5,077,280 A | 12/1991 | Sommadossi et al. |
| 5,089,500 A | 2/1992 | Daluge |
| 5,118,672 A | 6/1992 | Schinazi et al. |
| 5,130,303 A | 7/1992 | Akiyama et al. |

(Continued)

FOREIGN PATENT DOCUMENTS

| | | |
|---|---|---|
| CH | 492 738 | 6/1970 |
| CN | 102079726 A | 6/2011 |

(Continued)

OTHER PUBLICATIONS

Fabris, Synthesis, 2014, vol. 46, 2333-2346. (Year: 2014).*
Ramesh, Asian J Org Chem, 2017, VOl , 984-987. (Year: 2017).*
Ahmad, S. et al. "(3R,5S,E)-7-(4-(4-Fluorophenyl)-6-isopropyl-2-(methyl(1-methyl-1H-1,2,4-triazol-5-yl)amino)pyrimidin-5-yl)-3,5-dihydroxyhept-6-enoic acid (BMS-644950): A rationally designed orally efficacious 3-hydroxy-3-methylglutaryl coenzyme—A reductase inhibitor with reduced myotoxicity potential", J Med Chem. (2008) 51:2722-2733.
Lee, Y. H. et al. "Synthesis and characterization of rosuvastatin calcium impurity A; a HMG-CoA reductase inhibitor", Tetra Letts. (2017) 58:2614-2617.
International Search Report and Written Opinion dated Mar. 25, 2019, in Application No. PCT/US2019/012762.
International Second Written Opinion (Rule 66) dated Nov. 28, 2019, in Application No. PCT/US2019/012762.
International Third Written Opinion (Rule 66) dated Feb. 7, 2020, in Application No. PCT/US2019/012762.

(Continued)

*Primary Examiner* — D Margaret M Seaman
(74) *Attorney, Agent, or Firm* — Knobbe, Martens, Olson & Bear, LLP

(57) ABSTRACT

Disclosed herein are acetal and cyclic acetal compounds, compositions, their preparation, and their uses. Some embodiments relate to their use as liver-targeting compounds.

31 Claims, No Drawings

(56) References Cited

U.S. PATENT DOCUMENTS

| | | | |
|---|---|---|---|
| 5,130,427 A | 7/1992 | Alexander et al. | |
| 5,142,051 A | 8/1992 | Holy et al. | |
| 5,153,183 A | 10/1992 | Kawabe et al. | |
| 5,157,027 A | 10/1992 | Biller et al. | |
| 5,159,067 A | 10/1992 | Schinazi et al. | |
| 5,204,355 A | 4/1993 | Zsadon et al. | |
| 5,210,085 A | 5/1993 | Liotta et al. | |
| 5,212,304 A | 5/1993 | Fung et al. | |
| 5,240,946 A | 8/1993 | Kinney et al. | |
| 5,246,937 A | 9/1993 | Hamden et al. | |
| 5,258,538 A | 11/1993 | Fung et al. | |
| 5,366,965 A | 11/1994 | Strein | |
| 5,437,772 A | 8/1995 | De Castro et al. | |
| 5,438,073 A | 8/1995 | Saurat et al. | |
| 5,464,748 A | 11/1995 | Sommadossi et al. | |
| 5,466,841 A | 11/1995 | Horrobin et al. | |
| 5,480,875 A | 1/1996 | Isomura et al. | |
| 5,514,798 A | 5/1996 | Bischofberger et al. | |
| 5,532,225 A | 7/1996 | Reist et al. | |
| 5,567,689 A | 10/1996 | Sommadossi et al. | |
| 5,583,122 A | 12/1996 | Benedict et al. | |
| 5,599,686 A | 2/1997 | DeFeo-Jones et al. | |
| 5,627,164 A | 5/1997 | Glazier | |
| 5,658,889 A | 8/1997 | Gruber et al. | |
| 5,663,159 A | 9/1997 | Starrett, Jr. et al. | |
| 5,665,386 A | 9/1997 | Benet et al. | |
| 5,681,590 A | 10/1997 | Bechard et al. | |
| 5,686,629 A | 11/1997 | Bischofberger et al. | |
| 5,716,928 A | 2/1998 | Benet et al. | |
| 5,719,303 A | 2/1998 | Yoshida et al. | |
| 5,721,219 A | 2/1998 | Ingall et al. | |
| 5,723,449 A | 3/1998 | Sommadossi et al. | |
| 5,750,493 A | 5/1998 | Sommadossi et al. | |
| 5,767,097 A | 6/1998 | Tam | |
| 5,789,608 A | 8/1998 | Glazier | |
| 5,814,639 A | 9/1998 | Liotta et al. | |
| 5,840,716 A | 11/1998 | Ubasawa et al. | |
| 5,854,231 A | 12/1998 | Camden | |
| 5,866,679 A | 2/1999 | DeFeo-Jones et al. | |
| 5,866,684 A | 2/1999 | Attwood et al. | |
| 5,869,467 A | 2/1999 | Holy et al. | |
| 5,914,331 A | 6/1999 | Liotta et al. | |
| 5,948,750 A | 9/1999 | Garsky et al. | |
| 5,962,440 A | 10/1999 | Sulsky | |
| 5,962,522 A | 10/1999 | Wacher et al. | |
| 5,990,093 A | 11/1999 | Schinazi et al. | |
| 6,004,927 A | 12/1999 | Benet et al. | |
| 6,028,054 A | 2/2000 | Benet et al. | |
| 6,037,335 A | 3/2000 | Takashima et al. | |
| 6,045,638 A | 4/2000 | Lundstrom | |
| 6,054,587 A | 4/2000 | Reddy et al. | |
| 6,110,903 A | 8/2000 | Kasibhatla et al. | |
| 6,117,873 A | 9/2000 | Acklin et al. | |
| 6,121,234 A | 9/2000 | Benet et al. | |
| 6,128,582 A | 10/2000 | Wilson et al. | |
| 6,130,326 A | 10/2000 | Ramasamy et al. | |
| 6,130,504 A | 10/2000 | Nakayama et al. | |
| 6,143,715 A | 11/2000 | Llinas-Brunet et al. | |
| 6,143,864 A | 11/2000 | DeFeo-Jones et al. | |
| 6,177,404 B1 | 1/2001 | DeFeo-Jones et al. | |
| 6,180,666 B1 | 1/2001 | Wacher et al. | |
| 6,194,390 B1 | 2/2001 | Lori et al. | |
| 6,194,391 B1 | 2/2001 | Schinazi et al. | |
| 6,211,201 B1 | 4/2001 | Granger et al. | |
| 6,245,749 B1 | 6/2001 | Schinazi et al. | |
| 6,284,748 B1 | 9/2001 | Dang et al. | |
| 6,294,672 B1 | 9/2001 | Reddy et al. | |
| 6,312,662 B1 | 11/2001 | Erion et al. | |
| 6,348,587 B1 | 2/2002 | Schinazi et al. | |
| 6,372,883 B1 | 4/2002 | Attwood et al. | |
| 6,391,305 B1 | 5/2002 | Feng et al. | |
| 6,395,716 B1 | 5/2002 | Gosselin et al. | |
| 6,395,763 B1 | 5/2002 | Stamos et al. | |
| 6,399,773 B1 | 6/2002 | Liu et al. | |
| 6,399,782 B1 | 6/2002 | Kasibhatla et al. | |
| 6,403,566 B1 | 6/2002 | Wang | |
| 6,407,077 B1 | 6/2002 | Gosselin et al. | |
| 6,423,695 B1 | 7/2002 | Tam et al. | |
| 6,444,652 B1 | 9/2002 | Gosselin et al. | |
| 6,448,281 B1 | 9/2002 | Beaulieu et al. | |
| 6,455,508 B1 | 9/2002 | Ramasamy et al. | |
| 6,458,773 B1 | 10/2002 | Gosselin et al. | |
| 6,486,204 B2 | 11/2002 | Waldstreicher et al. | |
| 6,489,476 B1 | 12/2002 | Dang et al. | |
| 6,495,677 B1 | 12/2002 | Ramasamy et al. | |
| 6,518,253 B1 | 2/2003 | Tam | |
| 6,525,033 B1 | 2/2003 | Schinazi et al. | |
| 6,545,007 B2 | 4/2003 | Sommadossi et al. | |
| 6,566,344 B1 | 5/2003 | Gosselin et al. | |
| 6,569,837 B1 | 5/2003 | Gosselin et al. | |
| 6,596,700 B2 | 7/2003 | Sommadossi et al. | |
| 6,602,664 B2 | 8/2003 | Schinazi et al. | |
| 6,608,027 B1 | 8/2003 | Tsantrizos et al. | |
| 6,608,067 B1 | 8/2003 | Tung et al. | |
| 6,613,896 B1 | 9/2003 | Ramasamy et al. | |
| 6,635,636 B1 | 10/2003 | Artico et al. | |
| 6,653,295 B2 | 11/2003 | Glunz et al. | |
| 6,727,267 B2 | 4/2004 | Jaen et al. | |
| 6,752,981 B1 | 6/2004 | Erion et al. | |
| 6,756,360 B1 | 6/2004 | Erion et al. | |
| 6,767,991 B1 | 7/2004 | Llinas-Brunet et al. | |
| 6,777,395 B2 | 8/2004 | Bhat et al. | |
| 6,784,166 B2 | 8/2004 | Devos et al. | |
| 6,809,101 B2 | 10/2004 | Fujishita et al. | |
| 6,846,810 B2 | 1/2005 | Armstrong et al. | |
| 6,864,244 B2 | 3/2005 | Connolly et al. | |
| 6,867,284 B1 | 3/2005 | Matassa et al. | |
| 6,911,428 B2 | 6/2005 | Zhu et al. | |
| 6,914,054 B2 | 7/2005 | Sommadossi et al. | |
| 6,946,115 B2 | 9/2005 | Erion et al. | |
| 6,994,959 B1 | 2/2006 | Tam | |
| 7,081,449 B2 | 7/2006 | Pietrzkowski et al. | |
| 7,091,209 B2 | 8/2006 | Gardelli et al. | |
| 7,094,768 B2 | 8/2006 | Roberts et al. | |
| 7,094,770 B2 | 8/2006 | Watanabe et al. | |
| 7,105,493 B2 | 9/2006 | Sommadossi et al. | |
| 7,148,349 B2 | 12/2006 | Reddy et al. | |
| 7,151,092 B2 | 12/2006 | Boyer et al. | |
| 7,169,766 B2 | 1/2007 | Sommadossi et al. | |
| 7,193,081 B2 | 3/2007 | Kopcho et al. | |
| 7,205,404 B1 | 4/2007 | Erion et al. | |
| 7,214,668 B2 | 5/2007 | Erion et al. | |
| 7,261,704 B2 | 8/2007 | Tachikawa et al. | |
| 7,303,739 B2 | 12/2007 | Erion et al. | |
| 7,351,399 B2 | 4/2008 | Erion et al. | |
| 7,429,572 B2 | 9/2008 | Clark | |
| 7,491,794 B2 | 2/2009 | Blatt et al. | |
| 7,498,320 B2 | 3/2009 | Reddy et al. | |
| 7,553,826 B2 | 6/2009 | Boyer et al. | |
| 7,582,758 B2 | 9/2009 | Martin | |
| 7,608,600 B2 | 10/2009 | Storer et al. | |
| 7,666,855 B2 | 2/2010 | Reddy et al. | |
| 7,816,345 B2 | 10/2010 | Erion et al. | |
| 8,003,625 B2 | 8/2011 | Matteucci et al. | |
| 8,063,025 B2 | 11/2011 | Hecker et al. | |
| 8,080,536 B2 | 12/2011 | Erion et al. | |
| 8,207,333 B2 * | 6/2012 | Casar | A61P 43/00 544/242 |
| 8,236,820 B2 | 8/2012 | Rigas | |
| 8,354,530 B2 * | 1/2013 | Zlicar | C07D 403/12 544/332 |
| 8,476,432 B2 * | 7/2013 | Ju | C07D 209/18 548/251 |
| 8,664,195 B2 | 3/2014 | Erion et al. | |
| 9,326,991 B2 | 5/2016 | Zhi et al. | |
| 9,353,061 B2 * | 5/2016 | Lin | A61K 31/221 |
| 9,676,729 B2 * | 6/2017 | De Lange | C07D 239/42 |
| 10,292,966 B2 | 5/2019 | Benjamin et al. | |
| 10,449,210 B2 | 10/2019 | Zhi et al. | |
| 10,463,648 B2 | 11/2019 | Benjamin et al. | |
| 11,278,559 B2 | 3/2022 | Zhi | |
| 2001/0041713 A1 | 11/2001 | Waldstreicher et al. | |
| 2002/0115596 A1 | 8/2002 | Garsky et al. | |
| 2002/0120130 A1 | 8/2002 | Gosselin et al. | |

(56) References Cited

U.S. PATENT DOCUMENTS

| | | |
|---|---|---|
| 2002/0147160 A1 | 10/2002 | Bhat et al. |
| 2002/0156081 A1 | 10/2002 | Hirst et al. |
| 2002/0187945 A1 | 12/2002 | Tam |
| 2002/0193415 A1 | 12/2002 | LaColla et al. |
| 2003/0008841 A1 | 1/2003 | Devos et al. |
| 2003/0050229 A1 | 3/2003 | Sommadossi et al. |
| 2003/0050320 A1 | 3/2003 | Hashimoto et al. |
| 2003/0060400 A1 | 3/2003 | LaColla et al. |
| 2003/0083306 A1 | 5/2003 | Imbach et al. |
| 2003/0087873 A1 | 5/2003 | Stuyver et al. |
| 2003/0225277 A1 | 12/2003 | Kopcho et al. |
| 2003/0229225 A1 | 12/2003 | Reddy et al. |
| 2003/0232760 A1 | 12/2003 | Garsky et al. |
| 2004/0006002 A1 | 1/2004 | Sommadossi et al. |
| 2004/0006007 A1 | 1/2004 | Grosselin et al. |
| 2004/0014696 A1 | 1/2004 | Lau et al. |
| 2004/0019232 A1 | 1/2004 | Hostetler et al. |
| 2004/0063651 A1 | 4/2004 | Morioka et al. |
| 2004/0063658 A1 | 4/2004 | Roberts et al. |
| 2004/0067877 A1 | 4/2004 | Schinazi et al. |
| 2004/0077563 A1 | 4/2004 | Lau et al. |
| 2004/0092476 A1 | 5/2004 | Boyer et al. |
| 2004/0147464 A1 | 7/2004 | Roberts et al. |
| 2004/0192651 A1 | 9/2004 | Reddy et al. |
| 2004/0266723 A1 | 12/2004 | Otto et al. |
| 2005/0031588 A1 | 2/2005 | Sommadossi et al. |
| 2005/0054645 A1 | 3/2005 | Miyazaki et al. |
| 2005/0075309 A1 | 4/2005 | Storer et al. |
| 2005/0090463 A1 | 4/2005 | Roberts et al. |
| 2005/0101775 A1 | 5/2005 | Erion et al. |
| 2005/0101776 A1 | 5/2005 | Gosselin et al. |
| 2005/0107312 A1 | 5/2005 | Keicher et al. |
| 2005/0182252 A1 | 8/2005 | Reddy et al. |
| 2005/0282782 A1 | 12/2005 | Martin |
| 2006/0014740 A1 | 1/2006 | Miller et al. |
| 2006/0030545 A1 | 2/2006 | Cheng et al. |
| 2006/0046981 A1 | 3/2006 | Shibata |
| 2006/0234962 A1 | 10/2006 | Olsen et al. |
| 2006/0270634 A1 | 11/2006 | Miller et al. |
| 2007/0213588 A1 | 1/2007 | Reddy et al. |
| 2007/0032448 A1 | 2/2007 | Hong et al. |
| 2007/0060498 A1 | 3/2007 | Gosselin et al. |
| 2007/0078111 A1 | 4/2007 | Tigyi et al. |
| 2007/0179114 A1 | 8/2007 | Erion et al. |
| 2007/0183706 A1 | 8/2007 | Huang |
| 2007/0203339 A1 | 8/2007 | Kopcho et al. |
| 2007/0249564 A1 | 10/2007 | Erion et al. |
| 2008/0009533 A1 | 1/2008 | Tino et al. |
| 2008/0125605 A1 | 5/2008 | Erion et al. |
| 2009/0209481 A1 | 8/2009 | Hecker et al. |
| 2010/0305060 A1 | 12/2010 | Hecker et al. |
| 2011/0009356 A1 | 1/2011 | Erion et al. |
| 2011/0098251 A1 | 4/2011 | Ebetino et al. |
| 2012/0039845 A1 | 2/2012 | Hecker et al. |
| 2012/0093729 A1 | 4/2012 | Erion et al. |
| 2012/0264735 A1 | 10/2012 | Young et al. |
| 2013/0310395 A1 | 11/2013 | Dodd et al. |
| 2014/0142052 A1 | 5/2014 | Lehn et al. |
| 2017/0056429 A1 | 3/2017 | Zhi |
| 2017/0158725 A1 | 6/2017 | Zhi |
| 2017/0183314 A1 | 6/2017 | Chen et al. |
| 2018/0291050 A1 | 10/2018 | Zhi |
| 2019/0388452 A1 | 12/2019 | Zhi |
| 2021/0251238 A1* | 8/2021 | Scott ............... A01N 63/30 |

FOREIGN PATENT DOCUMENTS

| | | | |
|---|---|---|---|
| CN | 107382875 A | | 11/2017 |
| DE | 1693219 A | | 9/1970 |
| EP | 0002062 A | | 5/1979 |
| EP | 0072531 A | | 2/1983 |
| EP | 0072987 | | 3/1983 |
| EP | 0158057 A | | 10/1985 |
| EP | 0161955 | | 11/1985 |
| EP | 0180276 A1 | | 5/1986 |
| EP | 0261283 A | | 3/1988 |
| EP | 0276196 A1 | | 7/1988 |
| EP | 0338372 A2 | | 10/1989 |
| EP | 0353692 B1 | | 2/1990 |
| EP | 0481214 A | | 4/1992 |
| EP | 0521471 A1 | | 1/1993 |
| EP | 1704856 A1 | | 9/2006 |
| EP | 2351762 A1 | | 8/2011 |
| GB | 2266525 A | | 11/1993 |
| GB | 2266527 A | | 11/1993 |
| JP | S56-138181 A | | 10/1981 |
| JP | S62-195392 A2 | | 8/1987 |
| JP | S62-249996 A2 | | 10/1987 |
| JP | S63-60929 | | 3/1988 |
| JP | H06-293785 | | 10/1994 |
| JP | H06-511246 A | | 12/1994 |
| JP | H08-508245 A | | 9/1996 |
| JP | H09-241284 A | | 9/1997 |
| JP | 2003-509428 A | | 3/2003 |
| JP | 2004-504326 | | 2/2004 |
| JP | 2009-502743 | | 1/2009 |
| JP | 2009-502790 A | | 1/2009 |
| JP | 2010-535817 | | 11/2010 |
| JP | 2013-508459 | | 3/2013 |
| JP | 2013-514973 A | | 5/2013 |
| KR | 1020100087931 A | | 8/2010 |
| KR | 1020160126700 A | | 11/2016 |
| KR | 1020170078033 A | | 7/2017 |
| WO | WO 1984/001573 | | 4/1984 |
| WO | WO 1987/005297 | | 9/1987 |
| WO | WO 1990/008155 | | 7/1990 |
| WO | WO 1990/010636 | | 9/1990 |
| WO | WO 1993/019075 | | 9/1993 |
| WO | WO 1995/07287 | | 3/1995 |
| WO | WO 1995/007920 | | 3/1995 |
| WO | WO 1996/001267 | | 1/1996 |
| WO | WO 1997/003679 | | 2/1997 |
| WO | WO 1997/022614 | | 6/1997 |
| WO | WO 1997/049717 | | 12/1997 |
| WO | WO 1998/008458 | | 3/1998 |
| WO | WO 1998/009668 | | 3/1998 |
| WO | WO 1998/038888 | | 9/1998 |
| WO | WO 1998/046630 | | 10/1998 |
| WO | WO 1999/004774 | | 2/1999 |
| WO | WO 1999/036074 | | 7/1999 |
| WO | WO 1999/045016 | | 9/1999 |
| WO | WO 1999/047549 | | 9/1999 |
| WO | WO 2000/014095 | | 3/2000 |
| WO | WO 2000/052015 | | 9/2000 |
| WO | WO 2001/018013 | | 3/2001 |
| WO | WO 2001/019829 | | 3/2001 |
| WO | WO 2001/027114 | | 4/2001 |
| WO | WO 2001/045509 | | 6/2001 |
| WO | WO 2001/045642 | | 6/2001 |
| WO | WO 2002/000673 | | 1/2002 |
| WO | WO 2002/008241 | | 1/2002 |
| WO | WO 2002/083143 A1 | | 10/2002 |
| WO | WO 2003/014821 | | 2/2003 |
| WO | WO 2003/014822 | | 2/2003 |
| WO | WO 2003/026573 | | 4/2003 |
| WO | WO 2003/026589 | | 4/2003 |
| WO | WO 2003/037908 | | 5/2003 |
| WO | WO 2003/051881 | | 6/2003 |
| WO | WO 2003/051896 | | 6/2003 |
| WO | WO 2003/051897 | | 6/2003 |
| WO | WO 2003/051898 | | 6/2003 |
| WO | WO 2003/051899 | | 6/2003 |
| WO | WO 2003/052053 | | 6/2003 |
| WO | WO 2003/068244 | | 8/2003 |
| WO | WO 2003/070739 A1 | | 8/2003 |
| WO | WO 2003/095665 | | 11/2003 |
| WO | WO 2004/002422 | | 1/2004 |
| WO | WO 2004/037161 | | 5/2004 |
| WO | WO 2004/041834 | | 5/2004 |
| WO | WO 2004/041837 | | 5/2004 |
| WO | WO 2004/046105 A2 | | 6/2004 |
| WO | WO 2007/020193 | | 2/2007 |
| WO | WO 2007/107276 A2 | | 9/2007 |
| WO | WO 2007/125547 | | 11/2007 |

(56) References Cited

FOREIGN PATENT DOCUMENTS

| WO | WO 2008/116156 | 9/2008 |
|---|---|---|
| WO | WO 2009/011850 | 1/2009 |
| WO | WO 2009/073506 | 6/2009 |
| WO | WO 2010/013279 | 2/2010 |
| WO | WO 2010/042600 | 4/2010 |
| WO | WO 2010/065760 | 6/2010 |
| WO | WO 2010/103320 A1 | 9/2010 |
| WO | WO 2010/105048 | 9/2010 |
| WO | WO 2011/084402 | 7/2011 |
| WO | WO 2011/160974 | 12/2011 |
| WO | WO 2012/038785 A1 | 3/2012 |
| WO | WO 2012/158811 | 11/2012 |
| WO | WO 2013/002969 | 1/2013 |
| WO | WO 2013/074386 | 5/2013 |
| WO | WO 2015/123352 | 8/2015 |
| WO | WO 2016/130417 | 8/2016 |
| WO | WO 2017/137469 | 8/2017 |

OTHER PUBLICATIONS

International Preliminary Report on Patentability dated May 11, 2020 for Application No. PCT/US2019/012762.
Alarcon R.A., "Studies on the In Vivo Formation of Acrolein: 3-Hydroxy-propylmercapturic Acid as an Index of Cyclophosphamide (NSC-26271) Activation," Cancer Treat Rep. (1976) 60(4): 327-335.
Aleksiuk et al., "Proximal Intraannular Modifictions of Calix[4]arene via its Spirodienone Derivative", J Chem Soc Chem Commun. (1993) 1: 11-13.
Alexakis et al., "Reactivity and Diastereoselectivity of Grignard Reagents toward the Hydrazone Functionality in Toluene Solvent," J Org Chem. (1992) 57(17): 4563-4565.
Alexander et al., "Preparation of 9-(2-Phosphonomethoxyethyl) Adenine Esters as Potential Prodrugs," Collect. Czech. Chem. Commun., (1994) 59: 1853-1869.
Ali et al., 2012, New anticancer agents: recent developments in tumor therapy. Anticancer Research 32(7):2999-3006.
Allison et al., "Immunosuppressive and other anti-rheumatic activities of mycophenolate mofetil", Agents Actions Suppl. (1993) 44: 165-188.
Amin et al., "1-Hydroxy-3-(methylpentylamino)-propylidene-1, 1-bisphosphonic Acid as a Potent Inhibitor of Squalene Synthase," Arznemittelforschung. (1996) 46(8): 759-762.
Anderson et al., "2-Chloro-4(R),5(R)-dimethyl-2-oxo-1,3,2-dioxphospholane, a new chiral derivatizing agent," J Org Chem (1984) 49(7): 1304-1305.
Anderson et al., "Cyclophosphamide and 4-Hydroxycyclophosphamide/Aldophosphamide Kinetics in Patients Receiving High-Dose Cyclophosphamide Chemotherapy," Clin Cancer Res. (1996) 2: 1481-1487.
Annaert et al., "Transport, Uptake, and Metabolism of the Bis(pivaloyloxymethyl)-EsterProdrug of 9-(2-Phosphonylmethoxyethyl) Adenine in an In Vitro Cell Culture System of the Intestinal Mucosa (Caco-2)," Pharm Res. (1997) 14(4): 492-496.
Anzenbacherová, et al., "In Vivo Study of the Effect of Antiviral Acyclic Nucleotide Phosphonate(R)-9-[2(phosphono-methoxy)propyl]adenine (PMPA, tenofovir) and Its Prodrug Tenofovir Disoproxil Fumarate on Rat Microsomal Cytochrome P450," Physiol Res. (2008) 57: 761-767.
Armstrong et al., "Covalently Linked Gramicidin Channels: Effects of LinkerHydrophobicity and Alkaline Metals on Different Stereoisomers", Biophys J. (2001) 80(4):1810-1818.
Arnér et al., "Mammalian Deoxyribonucleoside Kinases," PharmaC Ther. (1995) 67(2): 155-186.
Arnold et al., "Über Beziehungen zwischen chemischer Konstitution und cancerotoxischer|Wirkung in der Reihe der Phosphamidester des Bis -(β-chloräthyl)-amins," Konstitution und Wirkung, (1961) 11(2a): 143-158.
Aso et al., "Synthesis of a new class of spin-labeled purine ribonucleosides and development of novel nucleophilic reaction to form 2,6,8-trifunctionalized purine derivatives," J Chem Soc Perkins Trans. (2000) 2: 1637-1638.
Atiq et al., "Treatment of Unresectable Primary Liver Cancer With Intrahepatic Fluorodeoxyuridine and Mitomycin C Through an Implantable Pump," Cancer (1992) 69: 920-924.
Attanasi et al., "Syntheis of some phosphorus derivatives of cardanol", Phosphor Sulfur (1988) 35(1-2): 63-65.
Auberson et al., "N-Phosphoalkyl-5-Aminomethylquinoxaline-2,3-Diones: In Vivo Active Ampa and NMDA(Glycine) Antagonists," Bioorg Med Chem Lttr. (1999) 9(2): 249-254.
Ayral-Kaloustian et al., "Synthesis of Partially-Protected D-Frutofuranoses and D-Fructose-6-Phosphates", Carbohydrate Res. (1991) 214: 187-192.
Baker et al., "Microtiter Plate Assay for the Measurement of Glutathione and Gluthione Disulfide in Large Numbers of Biological Samples," Anal Biochem. (1990) 190: 360-365.
Ballatore et al., "Carboxylic Acid (Bio) Isosteres in Drug Design", Chem Med Chem (2013) 8: 385-395.
Balthazor et al. "Nickel-Catalyzed Arbuzov Reaction: Mechanistic Observation," J Org Chem. (1980) 45: 5425-5426.
Balzarini et al., "5-Phosphoribosyl 1-Pyrophossphate Synthetase converts the acyclic nucleoside Phosphonates 9-(3-Hydroxy-2-phosphonylmethoxypropyl)adenine and 9-(2-Phosphonyl-methoxyethyl)adenine directly to their antivirally active Diposphate derivatives", J Biol Chem. (1991) 266(14): 8686-8689.
Balzarini et al., "Activity of the (R)-enantiomers of 9-(2-phosphonylmethoxypropyl)-Adenine and 9-(2-phosphonylmethoxypropyl)-2,6-diamiopurine against Human Immunodeficiency Virus in Different Human Cell Systems" Biochem Biophys Res Commun. (1996) 219: 337-341.
Banker et al., "Modern Pharmaceutics, 3ed.", Marcel Dekker, New York, 1996, pp. 451 and 596.
Banker et al. [Eds], "Modern Pharmaceutics", Marcel Dekker, Inc. Fourth Edition, (2002) Chapters 9-10; 98 pages.
Barluenga et al., "β-Substituted Organolithium Compounds. New Reagents for Synthesis," J Org Chem. (1979) 44(26): 4798-4801.
Barluenga et al., "Reduction of 1,3-Diimines. A New and General Method of Synthesis of gamma-Diamines, beta-Amino Ketones, and Derivatives with Two and Three Chiral Centers," J Org Chem. (1983) 48(13): 2255-2259.
Barluenga et al., "Stereoselective Synthesis of 1,3-Amino Alcohols and 1,3-Amino Ketones," J Org Chem. (1992) 57(4): 1219-1223.
Beaucage et al., "The Synthesis of Modified Oligonucleotides by the Phosphoramidite Approach and Their Applications," Tetrahed. (1993) 49(28): 6123-6194.
Bedford et al., "Synthesis of Water-Soluble Prodrugs of the Cytotoxic Agent Combretastatin A4," Bioorg Med Chem Lett. (1996) 6(2): 157-160.
Beigelman et al., "New Syntheses of 2'-C-Methylnucleosides Starting from D-Glucose and D-Ribose," Carbohydrate Res. (1987) 166: 219-232.
Beilstein Registry 1028505, "2-phenoxy-6,6-diphenyl-[1,3,2]oxazaphosphinane 2-oxide", Beilstein Institute for Organic Chemistry, Frankfurt, Germany; Nov. 28, 1988, 2 pages.
Beilstein Registry 1083232, "2-phenoxy-4-phenyl-<1,3,2>diazaphosphinane", Beilstein Institute for Organic Chemistry, Frankfurt, Germany, Nov. 29, 1988; 1 page.
Beilstein Registry 1085700, "3-mehtyl-2-phenoxy-6-phenyl-[1,3,2]diazaphosphinane 2-oxide", Beilstein Institute for Organic Chemistry, Frankfurt, Germany, entry date Nov. 29, 1988, in 1 page.
Beilstein Registry 6530655, "2-phenoxy-6,6-diphenyl-[1,3,2]oxazaphosphinane 2-oxide", Beilstein Institute for Organic Chemistry, Frankfurt, Germany, Apr. 18, 1994, 2 pages.
Beilstein Registry No. 3635189, "carboxy-phosphonic acid; sodium salt", Beilstein Institute for Organic Chemistry, Frankfurt, Germany, Feb. 26, 1991, 31 pages.
Benhamou et al., "Safety and efficacy of adefovir dipivoxil in patients co-infected with HIV-1 and lamivudine-resistant hepatitis B virus: an open-label pilot study," Lancet. (2001) 358(9283): 718-23.
Bentrude et al., "Stereo- and Regiochemistries of the Oxidations of 2-Methoxy-5-tert-butyl-1,3,2-dioxaphosphorinanes and the Cyclis Methyl 3'5'-Phosphite of Thymidine by $H_2O/I_2$ and $O_2$/AIBN to P-Chiral Phos-

(56) References Cited

OTHER PUBLICATIONS phates. $^{17}$O NMR Assignment of Phosphorus Configuration to the Diasteromeric Thymidine Cyclic Methyl 3'5'-Monophosphates," J Am Chem Soc. (1989) 111: 3981-3987.
Bentrude et al. "Conformation of Saturated Six-Membered-Ring Phosphorus|Heterocycles. 2-Aryl-1,3,2lambda$^{5}$-oxazapphosphorinanes" J Am Chem Soc. (1988) 110: 7119-7127.
Benzaria et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," J Med Chem. (1996) 39(25): 4958-4965.
Berry et al., "High-Yield Preparation of Isolated Rat Liver Parenchyman Cells," J Cell Biol. (1969) 43: 506-520.
Bertocchio et al., "Additions nucléophiles des cétones sur les fonctions éthyléiques activés," Bull. Soc. Chim. Fr, 1962, fasciclue 7, 307: 1809-1813.
Bespalov et al., "Prologation of morphine analgesia by competitive NMDA receptor antagonist D-CPPene (SDZ EAA 494) in rats," Euro J Pharmacol. (1998) 351: 299-305.
Bhatia et al., A new approach to the Synthesis of Ether Phospolipids. Etc. Tetra Lttrs. (1987) 28(3): 271-274.
Bhongle et al., "Expedient and High-Yield Synthesis of Alkylphosphonyl Dichlorides Under Mild, Neutral Conditions: Reaction of Bis(Trimethylsilyl) Alkyl Phosphonates with Oxalyl Chloride/Dimethylformamide," Synth Commun. (1987) 17(9-16): 1071-1076.
Bijsterbosch et al., "Disposition of the Acyclic Nucleoside Phosphonate (S)-9-(3-Hydroxy-2-Phosphonylmethoxypropyl) Adenine," Antimic Agt Chemother. (1998) 42(5): 1146-1150.
Bird et al., "Synthesis of Novel N-Phosphonoalkyl Dipeptide Inhibitors of Human Collagenase," J Med Chem. (1994) 73: 158-169.
Boddy et al., "Individual Variation in the Activation and Inactivation of Metabolic Pathways of Cyclophosphamide," J Nat Cancer Inst. (1992) 84(22): 744-748.
Borch et al.: "The Mechanism of Activation of 4-Hydroxycyclophosphamide," J Med Chem. (1987) 30: 427-431.
Borch et al., "Synthesis and Antitumor Properties of Activated Cyclophosphamide Analogues," J Med Chem. (1991) 34(10): 3044-3052.
Borch et al., "Synthesis, Activation and Cytotoxicity of Aldophosphamide Analogues," J Med Chem. (1991) 34(10): 3052-3058.
Boyd et al., "Synthesis and Antitumor Activity of Cyclophosphamide Analogues. 3. Preparation, Molecular Structure Determination, and Anticancer Screening of Racemic cis- and trans-4-Phenylcyclophosphamide," J Med Chem. (1980) 23(4): 372-375.
Boyer et al., "The Discovery of MB07133: A HepDirect® Prodrug of Cytarabine Monophosphate for the Treatment of Hepatocellular Carcinoma", Poster; Prospective, Boston, MA (May 2006); 1 page.
Boyer et al., "Synthesis and Characterization off a Novel Liver-Targeted Prodrug of Cytosine-1-beta-D-arabinofuranoside Monophosphate for the Treatment of Hepatocellular Carcinoma," J Med Chem (2006) 49: 7711-7720.
Braess et al. "Oral Cytarabine Ocfostate in Acute Myeloid Leukemia and non-Hodgkins's Lymphoma—Phase I/II Studies and Pharmacokinetics", Leukemia (1998) 12: 1618-1626.
Brain et al., "Modulation of P450-Dependent Ifosfamide Pharmacokinetics: a Better Understanding of Drug Activation In Vivo," British J Cancer 77(11): 1768-1776.
Brechbühler et al., "Die Reaktion von Carbonsäuren mit Acetalen des N,N-Dimethylformamids: eine Veresterungsmethode," Helvetica Chimica Acta (1965) 48(7): 1746-1771.
Brenna et al., "Affinity-Chromatography Purification of Alkaline Phosphatase from Calf Intestine," Biochem J., (1975) 151: 291-296.
Brill et al., "Arbuzov-like Dealkylation Reactions of Transition-Metal-Phosphite Complexes," Chem Rev (1984) 84(6): 577-585.
Brock et al., "Acrolein, the Causative Factor of Urotoxic Side-effects of Cyclophosphamide, Ifosfamide, Trofosfamide and Sufosfamide," Drug Res. (1979) 29(4): 659-661.

Bronson et al., "Synthesis and Antiviral Activity of Nucleotide Analogs Bearing the (S)-(3-hydroxy-2-phosphonylmethoxy)propyl Moiety Attached to Adenine, Guanine, and Cytosine," in Nucleotide Analogues as Antiviral Agents; (1989) Chapter 6, pp. 88-102.
Bronson et al., "Synthesis and Antiviral Activity of Phosphonylmethoxyethyl Derivatives of Purine and Pyrimidine Bases," in Nucleotide Analogues as Antiviral Agents (1989), ACS Symposium Series 401, American Chemical Society; Chapter 5, pp. 72-87.
Brown et al., "The Nucleophilic Displacement Route to Homochiral Arylphosphine Oxides," Tetrahedron, (1990) 46(13/14): 4877-4886.
Burrows et al., "Synthesis, Characterization, and Electrochemistry of a Series of Iron(II) Complexes Containing Self-Assembled 1,5-Diaza-3,7-diphosphabicyclo[3.3.1]nonane Ligands", Inorg Chem. (2009) 48(20): 9924-9935.
Campagne et al. "Synthesis of Mixed Phosphonate Diester Analogues of Dipeptides using BOP or PyBOP Reagents," Tetra Lttrs., (1993) 34(42): 6743-6744.
Campbell D.A., "The Synthesis of Phosphonate Esthers; An Extension of the Mitsunobu Reation," J Org Chem. (1992) 57(23): 6331-6335.
Canas et al., "Regioselective Ring Opening of Chiral Epoxyalcohols by Primary Amines," Tetrahedron Ltts. (1991) 32(47): 6931-6934.
CAS Registration No. 1348947-75-0; 1223158-02-8; 1222732-28-6; 921435-69-0; 874098- 86-9; available 2011 (Search Date: Aug. 28, 2020).
CAS Registration No. 1348535-65-8; 56687-50-4; 56599-48-5; 56599-47-4; 56599-46-3; 10564-28-2; available 2011 (Search date: Aug. 28, 2020).
Casara et al., "Synthesis of Acid Stable 5'-o-Fluorometer Phosphonates of Nucleosides," Bioorg Med Chem Lett. (1992) 2(2): 145-148.
Casteel et al., "Steric and Electronic Effects in the Aryl Phosphate to Arylphoshonate Rearrangement," Synthesis, (1991) 1999(9): 691-693.
Chabner et al., "Purification and Properties of Cytidine Deaminase from Normal and Leukemia Granulocytes", J Clin Invest. (1974) 53: 922-931.
Chabner B.A., "Cytidine Analogues", in Cancer Chemotherapy. Principles and Practice, Lippincott Williams & Wilkins (1990); Chapter 6; 154-179.
Chang et al., "Enhanced Cyophosphamide and Ifosfamide Activation in Primary Human Hepatocyte Cultures: Response to Cytochrome P-450 Inducers and Autoinduction by Oxazaphosphorines," Cancer Res. (1997) 57: 1946-1954.
Chen et al., "Intratumoral Activation and Enhanced Chemotheraputic Effect of Oxazaphosphorines following Cytochrome P-450 Gene Transfer: Development of a Combined chemptherapy/Cancer Gene Therapy Strategy," Cancer Res. (1995) 55: 581-589.
Chen et al., , "Sensitization of Human Breast Cancer Cells to Cyclophosphamide and Ifosfamide by Transfer of al Liver Cytochrome P450 Gene," Cancer Res.(1996) 56: 1331-1340.
Chen et al., "Conformation Analysis of Guanosine-5'-Diphospho-Fucose", Chin Chem Ltt. (1996) 7(1):29-32.
Chen et al., "Conformation Analysis of Tunicamycin V and its Natural Substrate", Chin Chem Ltt. (1996) 7(2):153-156.
Chu et al., "A Regiospecific Synthesis of 1-Methylamino-6-fluoro-7-(4-methylpiperazin-1-yl)-1,4-dihydro-4-oxoquinoline-3-carboxylic Acid," J Het Chem. (1985) 22: 1033-1034.
Chu et al., "Chemistry and Antiviral Activities of Acyclonucleosides," J Het Chem. (1986) 23(2): 289-319.
Clarke et al., "Oxidative Metabolism of Cyclophosphamide: Identification of the Hepatic Monooxygenase Catalysts of Drug Activation," Cancer Res. (1989) 49: 2344-2350.
Coates et al., "Annelative Ring Expansion via Intramolecular [2+2] Photocycloaddition of αβ-Unsaturated γ-Lactones and Reductive Cleavage: Synthesis of Hydrocyclopentacyclooctene-5-carboxylates," J Org Chem. (1982) 47(19): 4005.
Cohen, S.S. "The Mechanisms of Lethal Action of Arabinosyl Cytosine (araC) and Arabinosyl Adenine (araA)", Cancer (1977) 40(1): 509-518.

(56) References Cited

OTHER PUBLICATIONS

Commercon et al., "Diastereoselective Chlorocyclofunctionalization of N-Allylic Trichloroacetamides : Synthesis of an Analogue and Potential Precursor of RP49532," Tetrahed Ltts. (1990) 31(27): 3871-3874.

Cooper et al., "Use of Carbohydrate Derivatives for Studies of Phosphorus Stereo-chemistry. Part II. Synthesis and Configurational Assignments of 1,-3,2-Oxathiaphosphrinan-2-ones and 1,3,2-Dioxaphosphorinan-2-thiones," J.C.S. Perkin I, (1974) 3/2422:1049-1052.

Coppi, et al., "Lewis Acid Mediated Condensation of Alkenols and Aldehydes. A Selective Synthesis of Tetrahydropyrans and Oxepanes," J Org Chem., (1988) 53(4): 911-913.

Corey et al., "Enantioselective and Practical Syntheses of R- and S-Fluoxetines," Tetra Lttrs. (1989) 30(39): 5207-5210.

Cote et al., "D-2 dopamine receptor-mediated inhibition of adenylate cyclase activity in theintermediate lobe of the rat pituitary gland requires guanosine 5'-triphosphate," Endocrinology (1982) 110(3):812-819.

Cruz-Hernandez et al., Benefits of Structured and Free Monoacylglycerols to Deliver Eicosapentaenoic (EPA) in a Model of Lipid Malabsorption, Nutrients (2012) 4(12):1781-1793.

Cullis, P.M., "The Stereochemical Course of Iodine-Water Oxidation of Dinucleoside Phosphite Triesters," J Chem Soc. Chem. Commun., No. 1, 1984, pp. 1510-1512.

Cundy K.C., "Clinical pharmacokinetics of the antiviral nucleotide analogues cidofovir and adefovir," Clin Pharmacokinet. (1999) 36(2): 127-143.

Cundy et al., "Oral formulations of adefovir dipivoxil: in vitro dissolution and in vivo bioavailability in dogs," J Pharm Sci. (1997) 86(12): 1334-1338.

Curran et al., "Thermolysis of Bis[2-[(trimethylsilyl)oxy]prop-2-yl]furoXan (TOP—furoxan). The First Practical Method for Intermolecular Cycloaddition of an in Situ Generated Nitrile Oxide with 1,2-Di- and Trisubstituted Olefins," J Am Chem Soc. (1985) 107(21): 6023-6028.

Dang et al., "A New Regio-Defined Synthesis of PMEA," Nucleosides & Nucleotides (1998) 17(8): 1445-1451.

Das U.N., "Biological Significance of Essential Fatty Acids," J Assoc Physicians of India (Apr. 2006) 54: 310-319.

Database Registry. Chemical Abstracts Service, Columbus, Ohio, US; STN Database Accession No. 1982:159892. XP002777344, 2 pages.

Database Registry. Chemical Abstracts Service, Columbus, Ohio, US; STN Database Accession No. 94444-94-7; entered Jan. 26, 1985; 1 Page.

Database Registry. Chemical Abstracts Service, Columbus, Ohio, US; STN Database Accession No. 125083-67-2; entered Feb. 2, 1990; 1 Page.

Database Registry. Chemical Abstracts Service, Columbus, Ohio, US; STN Database Accession No. 1996:144369. 1 page.

Database Registry. Chemical Abstracts Service, Columbus, Ohio, US; STN Database Accession No. 1996:204511; XP-002777346. 3 pages.

Database Registry. Chemical Abstracts Service, Columbus, Ohio, US; STN Database Accession No. 745762-82-7; entered Sep. 19, 2004; 1 Page.

Database Registry. PubChem—SID #22395163—NCBI Structure "Adenosine-5'-Triphosphate", Feb. 23, 2007, retrieved Jan. 10, 2020, 9 pages.

Database Registry. Chemical Abstracts Service, Columbus, Ohio, US; Sep. 28, 2008. XP002777347, retrieved from STN Database Accession No. 1053732-62-9; 1 page.

Database Registry. Chemical Abstracts Service, Columbus, Ohio, US; Sep. 28, 2008. XP002777348, retrieved from STN Database Accession No. 1053654-17-3; 1 page.

Davis et al., "Effect of Withania somnifera on cyclophosphamide-induced urotoxicity," Cancer Lett. (2000) 148: 9-17.

Dearfield et al., "Analysis of the Genotoxicity of Nine Acrylate/Methacrylate Coumpounds in L5178Y Mouse Lymphoma Cells," Mutagen. (1989) 4: 381-393 (1989).

Dechant et al., "Ifosfamide/Mesna—A Review of its Antineoplastic Activity, Pharmacokinetic Properties and Therapeutic Efficacy in Cancer," Drugs (1991) 42(3), 428-467.

De Clercq et al., "A novel selective broad-spectrum anti-DNA virus agent," Nature (1986) 323: 464-467.

De Clercq et al., "Antiviral activity of phosphonylmethoxyalkyl derivatives of purine and pyrimidines.," Antiviral Res. (1987) 8(5-6): 261-272.

Deeks et al., "The Safety and Efficacy of Adefovir Diplvoxil, a Novel Anti-Human Immunodeficiency Virus (HIV) Therapy, in HIV-Infected Adults: A, Randomized, Double-Blind, Placebo-Controlled Trial," J Infect Dis. (1997) 176(6): 1517-1523.

DeLeve et al., "Cellular Target of Cyclophosphamide Toxicity in the Murine Liver: Role of Glutathione and Site of Metabolic Activation," Hepatol. (1996) 24(4): 830-837.

De Lombaert et al., "N-Phosphomomethyl Dipeptides and Their Phosphonate Prodrugs, a New Generation of Neutral Endopeptidase (NEP, EC 3.4.24.11) Inhibitors", J Med Chem. (1994) 37(4): 498-511.

De Lombaert et al., "Pharmacological profile of a Non-Peptidic Dual Inhibitor of Neutral Endopeptidase 24.11 and Endothelin-converting enzyme," Biochem Biophys Res Commun. (1994) 204(1): 407-412.

Denmark et al., "Asymmetric Electrophilic Amination of Chiral Phosphorus-Stabilized Anions" Tetrahedron (1992) 48(11): 2191-2208.

Desos et al., "Structure-Activity Relationships in a Series of 2(1H)-Quinolones Bearing Different Acidic Function in the 3-Position: 6,7-Dichloro-2(1H)-oxoquinoline-3-phosphonic Acid, a New Potent and Selective AMPA/Kainate Antagonist with Neuroprotective Properties," J Med Chem. (1996) 39(1): 197-206.

Desta et al., "Stereoselective Metabolism of Cisapride and Enantiomer-Enantiomer Interaction in Human Cytochrome P450 Enzymes: Major Role of CYP3A," J Pharmacol Exp Ther. (2001) 298(2): 508-520.

De Waziers et al., "Cytochrome P450 Isoenzymes, Epoxide Hydrolase and Glutathlone Transferases in Rat and Human Hepatic and Extrahepatic Tissues1," J Pharm Exp Ther., (1990) 253(1): 387-394.

Dickson et al., "Orally Active Squalene Synthase Inhibitors: Bis((acyloxy)alkyl) Prodrugs of the alpha-Phosphonosulfonic Acid Moiety," J Med Chem. (1996) 39: 661-664.

Dornow et al., "Über einige Derivate der Benzoylessigsäure," in Chemische Berichte by C. Schöpf [Ed.], (1949) 82: 254-257.

Dyatkina et al., "Synthesis of the Four Possible Stereoisomeric 5'-Nor Carbocyclic Nucleosides from One Common Enantiomerically Pure Starting Material," Tetrahed Lttr. (1994) 35(13): 1961-1994.

Dymock, B.W., "Emerging Therapies for Hepatitis C Virus Infection," Expert Opin Emerg Drugs (2001) 6(1): 13-42.

Echizen et al., "Identifcation of CYP3A4 as the Enzyme Involved in the Mono-N-Dealkylation of Disopyramide Enantiomers in Humans," Drug Metab Dispos. (2000) 28(8): 937-944.

Edmunson et al., "Cyclic Organophosphorus Compounds, Part 23, Configurational Assignments in the 4-Phenyl-1.3,2lambd5-dioxaphosphorinane Series. X-Ray Molecular Structure of cis-2-Benzylamino-4-phenyl-1.3.2-dioxaphosphorinane 2-Oxide," J Chem Res Synop.(1989) 5: 122-123.

Eliel et al., "Oxygen-17 NMR Spectra of Cyclic Phosphites, Phosphates, and Tiophosphates", J Am Chem Soc. (1986) 108(21): 6651-6661.

Elliot et al., "Synthesis and Biological Evaluation of Phosphonamidate Peptide Inhibitors of Enkephalinas and Angiotensin-Converting Enxyme," J Med Chem. (1985) 28(9): 1208-1216.

Enriquez et al., "Conjugation of Aadenine Arabinoside 5'-Monophosphate toArabinogalactan: Cynthesis, Characterization, and Antiviral Activity," Bioconj Chem. (1995) 6(2): 195-202.

Erion et al. "HepDirectTM Prodrugs for Targeting Nucleotide-Based Antiviral Drugs to the Liver" Curr Opin Invest Drugs (2006) 7(2): 109-117.

(56) References Cited

OTHER PUBLICATIONS

Erion et al., "Design, Synthesis, and Characterization of a Series of Cytochrome P450 3A-Activated Prodrugs (HepDirect Prodrugs) Useful for Targeting Phosph(on)ate-Based Drugs to the Liver," J Am Chem Soc. (2004) 126(16): 5154-5163.
Erion et al., "Liver-Targeted Drug Delivery Using HepDirect Prodrugs" J Pharmacol Exper Ther. (2005) 312(2): 554-560.
Erion et al., "Liver-Targeted Nucleoside Prodrugs," presented at the Gordon Research Conference: Purines, Pyrimidines and Related Substances, Newport, RI (Jun.-Jul. 2003), 38 pages.
Erion et al., "HepDirect(TM) Prodrugs: A Novel Strategy for Targeting Drugs to the Liver," Hepatology (2002) 36(4-2): Abstract No. 551, p. 301A.
Erion et al., "Prodrugs phosphorus-containing compounds and pharmacodynamic action", retrieved from STN Database accession No. 2001:808252; 1 pages.
Erion et al., "Preparation of cyclic nucleotides as FBPase inhibitor prodrugs" retrieved from STN Database accession No. 1999:576934; 4 pages.
Evans et al., "New Procedure for the Direct Generation of Titanium Enolates. Diastereoselective Bond Constructions with Representative Electrophiles," J Am Chem Soc. (1998) 112(22): 8215-8216.
Evans et al., "Stereoselective Aldol Reactions of Chlorotitanium Enolates. An Efficient Method of the Assemblage of Polypropionate-Related Synthons," J Am Chem Soc. (1991) 113(3): 1047-1049.
Farquhar et al., "Synthesis and Antitumor Evaluation of Bis[(pivaloyloxy)methyl] 2'-Deoxy-5-fluorouridine 5'-Monophosphate (FdUMP): A Strategy to Introduce Nucleotides into Cells," J Med Chem. (1994) 37(23): 3902-3909.
Farquhar et al. "Biologically-Cleavable Phosphate Protective Groups: 4-Aclioxt-1,3,2-Dioxaphosphorinanes as Neutral Latent Precursors of Dianionic Phosphates," Tetra Lttrs. (1995) 36(5): 655-658.
Farquhar et al., "5'-[4-(Pivaloyloxy)-1,3,2-dioxaphosphorinan-2-yl]-2'-deoxy-5-fluorouridine: A membrane-permeating Prodrug of 5-fluoro-2'-deoxyuridylic acid (FdUMP)", J Med Chem. (1995) 38(3): 488-495.
Farquhar et al., "Biologically Reversible Phosphate-Protective Groups," J Pharm Sci. (1983) 72(3): 324-325.
Farquhar et al., "Synthesis and Biological Evaluation of Neutral Derivatives of 5-Fluoro-2'- deoxyuridine 5'-Phosphate," J Med Chem. (1983) 26(8): 1153-1158.
Farquhar et al., "Synthesis and Biological Evaluation of 9-[5'-(2-Oxo-1,3,2-oxazaphosphorinan-2-yl)-beta-D-arabinosyl]adenine and 9-[5'-(Oxo-1,3,2-dioxazaphosphorinan-2-yl)-beta-D-arabinosyl]adenine: Potential Neutral Precursors of 9-[-62 -D-Arabinofuranosyl]adenine 5'-Monophosphate," J Med Chem. (1985) 28(9): 1358-1361.
Fiume et al., "Inhibition of Hepatitis B Virus Replication By Vidarbine Monophosphate Conjugated with Lactosaminated Serum Albumin," The Lancet (1988) 2: 13-15.
Fraiser et al., "Murine strain differences in metabolism and bladder toxicity of cyclophosphamide," Toxicol. (1992)75: 257-272.
Freed et al., "Evidence for Acyloxymethyyl Esters of Pyridmidenc, 5'-Deoxyribonucleotides as extracellular sources of active 5'-deoxyribonucleotides in cultured cells," Biochem Pharmcol. (1989) 38(19): 3193-3198.
Freeman et al., "Prodrug Design for Phosphates and Phosphonates", Chapter 3; Prog Med Chem. (1997) 34: 111-147.
Freer et al., "A new route to famiciclovir via palladium catalysed allylation", Tetrahedron (2000) 56(26): 4589-4595.
Friis et al., "Prodrugs of Phosphates and Phosphonates: Novel Lipophilic alpha-acyloxyalkyl Ester Derivatives of Phosphate- or Phosphonate Containing Drugs Masking the Negative Charges of these Groups," Euro J Pharm Sci., (1996) 4: 49-59.
Fujii et al., "Ruthenium(II)-Catalyzed Asymmetric Transfer Hydrogenation of Ketones Using A Formic Acid-Triethylamine Mixture," J Am Chem Soc.(1996) 118: 2521-2522.
Furegati et al., "Stereochemistry of the Inhibition of alpha-Chymotrypsin with Optically Active cis-Decaline-Type Organosphosphates: $^{31}$P-NMR Studies," Helvetica Chimica Acta (1998) 81: 1127-1138.
Gao et al., "Asymmetric Synthesis of Both Enantiomers of Tomoxetine and Fluoxetine. Seletive Reduction of 2,3-Epoxycinnamyl Alcohol with Red-A1," J Org Chem. (1988) 53(17): 4081-4084.
Gilard et al., "Chemical Stability and Fate of the Cytostatic Drug Ifosfamide and its N-Dechloroethylated Metabolites in Acidic Aqueous Solutions," J Med Chem. (1999) 42(14): 2542-2560.
Gilead Press Release, "Gilead Achieves Primary Endpoint in Phase III Study of Adefovir Dipivoxil for Chronic Hepatitis B Virus Infection," (2001); 3 pages.
Goodman and Gilman's, "The Pharmacological Basis of Therapeutics", Eighth Edition, Pergamon Press, Inc., (1990); TOC.
Gish et al., "Nucleic Acids. 11. Synthesis of 5'-Esters of 1-beta-D-Arabinofuranosylcytosine Possessing Antileukemic and Immunosuppressive Activity", J Med Chem. (1971) 14(12): 1159-1162.
Gorenstein et al., "Stereoelectronic Effects in the Reactions of Epimeric 2-Aryloxy-2-oxy-1,3,2-dioxaphosphorinanes and Oxazaphosphorinanes," J Am Chem Soc. (1980) 102(15): 5077-5081.
Grant, S., "Biochemical Modulation of Cytosine Arabinoside", Pharmac Ther. (1990) 48: 29-44.
Greene et al., Protective Groups in Organic Synthesis, John Wiley, New York, 1999; (TOC only) 4 pages.
Groen et al., "Intracellular Compartmentation and Control of Alanine Metabolism in Rat Liver Parenchymal Cells," Eur J Biochem. (1982) 122: 87-93.
Gududuru et al., "Identification of Darmstoff analogs as selective agonists and antagonists of lysophosphatidic acid receptors", Bioorg Med Chem Lett. (Dec. 31, 2006) 16:451-456.
Guida et al., "Structure-Based Design of Inhibitors of Purine Nucleoside Phosphorylase. 4. A Study of Phosphate Mimics," J Med Chem. (1994) 37(8): 1109-1114.
Gurtoo et al., "Role of Glutathione in the Metabolism-dependent Toxicity and Chemotherapy of Cyclophosphamide," Cancer Res. (1981) 41: 3584-3591.
Gustin et al., "A Rapid, Sensitive Assay for Adenosine Deaminase," Anal Biochem. (1976) 71: 527-532.
Haddad et al., "Stereocontrolled Reductive Amination of 3-Hydroxy Ketones," Tetrahedron Ltts. (1997) 38(34): 5981-5984.
Hadváry et al., "Conformationally Restricted Analogs of Platelet-Activating Factor (PAF)", Helv Chim Acta 69(8): 1862-1871.
Hales et al., "Embryotoxicity of Phenyl Ketone Analogs of Cyclophosphamide," Teratology (1989) 39(1): 31-37.
Han et al., "Study of the prodrugs of peptide aldehydes as proteasome inhibitors", J Chin Pharma Sciences, (Dec. 31, 2012) 21:21-27.
Hammer et al., "Phosphorylation of the Nucelear Receptor SF-1 Modulates CofactorRecruitment: Integration of Hormone Signaling in Reproduction and Stress", Mol Cell (1999) 3: 521-526.
Hanson et al., "Regioselective enzymatic aminoacylation of Lobucavir to give an intermediate for Lobucavir prodrug," Biorg Med Chem. (2000) 8(12): 2681-2687.
Harada et al., "Resolution of 1,3-alkanediols via Chiral Spiroketals Derivatives from iota-Menthone," Tetra Lttr. (1987) 28(41): 4843-4846.
Hartung et al., "1,5-Diphosphabicyclo[3.3.1]nonane 1,5-Disulfide", Acta Cryst. (1988) C44: 1438-1440.
Harvey D.J., "Pyridine-containing Derivatives for the Structural Elucidation of the Alkyl Chains of Lipids by Mass Spectrometry and a Comparison with the Spectra of Related Heterocyclic Derivatives", Spectros. Int. J. (1990) 8:211-244.
Hatse S., "Mechanistic study on the cytostatic and tumor cell differentiation-inducing properties of 9-(2-phosphonylmethoxyethyl)adenine (PMEA, adefovir)-collected publications," Verh K Acad Geneeskd Belg. (2000) 62(5): 373-384.
Hayakawa et al., "A General Approach to Nucleoside 3'- and 5'-Monophospates", Tetra Lttrs. (1987) 28(20): 2259-2262.
Hayakawa et al., "Benzimidazolium Triflate as an Efficient Promoter for Nucleotide Synthesis via the Phosphoramidite Method," J Org Chem. (1996) 61(23): 7996-7997.

(56) References Cited

OTHER PUBLICATIONS

He et al., "Inactivation of Cytochrome P450 3A4 by Bergamottin, a Component of Grapefruit Juice," Chem Res Toxicol. (1998) 11(4): 252-259.
Hecker et al., "Prodrugs of Phosphates and Phosphonates", J Med Chem. (2008) 51(8): 2328-2345; publ online Feb. 1, 2008.
Hessler E.J., "An Efficient Synthesis of 1-beta-D-Arabinofuranosylcytosine," J Org Chem. 41(10):1828-1831 (1976).
Hillers et al., "Analogs of pyrimidinemono- and polynucleotides. VI. Phosphates of 1-(1,4-dihydroxy-2-pentyl) thymine and 1-(1,3-dihydroxy-2-propyl)uracil", Chemical Abstracts by The American Chemical Society (1978) 89 (17): 607-608; Chemical Abstr. 146864u.
Hilton J., "Role of Aldehyde Dehydrogenase in Cyclophosphamide-resistant L1210 Leukemia," Cancer Res. (1984) 44: 5156-5160.
Hirayama et al., "Structure and conformation of a novel inhibitor of angiotensin I converting enzyme-a tripeptide containing phosphonic acid," Int J Pept Protein Res. (1991) 38: 20-24.
Ho et al., "Cytotoxicity of cytotoxicity of antiviral nucleotides adefovir and cidofovir is induced by the expression of human renal organic anion transporter 1", J Am Soc Nephrol. (2000) 11(3): 383-393.
Hoeffler et al., "Chemical Synthesis of Enantiopure 2-C-Methyl-D-Erythritol 4-Phosphate,the Key Intermediate in the Mevalonate-Independent Pathway for Isoprenoid Biosynthesis", Tetrahed. (2000) 56(11): 1485-1489.
Hoffman M., "A Simple, Efficient Synthesis of Dibenzyl and Di-p-nitrobenzyl 1-Hydroxyalkanephosphonates," Synthesis, J Synth Org Chem. (1988) 1: 62-64.
Holy et al., "Acyclic nucleotide analogues: synthesis, antiviral activity and inhibitory effects on some cellular and virus-encoded enzymes in vitro," Antiviral Res. (1990) 13(6):295-311.
Hong Z., "Hepavir B: a Safer and Liver-Targeting Prodrug of PMEA," Presented at the SRI-Antiviral Drug Discovery & Development Summit, Ribopharm Inc., Mar. 27, 2003; 19 pages.
Hong et al., "Clinical Update of Remofovir (Hepavir B): a Liver-targeting Prodrug of PMEA for the Treatment of Hepatitis B," Presented at the SRI-Antiviral Drug Discovery & Development Summit, Mar. 30, 2004; 23 pages.
Hori et al., "Palladium(II)-Catalyzed Asymmetric 1,3-Dipolar Cycloaddition of Nitrones to 3-Alkenoyl-1,3-oxazolidin-2-ones," J Org Chem. (1999) 64(14): 5017-5023.
Hughes D.L., "The Mitsunobu Reaction," Org React. (1992) vol. 42, Chapt. 2, pp. 335-656.
Hulst et al.: "A New 31P NMR Method for the Enantiomeric Excess Determination of Alcohols, Amines and Amino Acid Esters," Tetra Lttrs. (1993) 34(8): 1339-1342.
Hunston et al., "Synthesis and Biological Properties of Some Cyclic Phosphotriesters Derived from 2'-Deoxy-5-fluorouride," J Med Chem. (1984) 27: 440-444.
Inanaga et al., "A Rapid Esterification by Means of Mixed Anhydride and its Application to Large-Ring Lactonization," Bull Chem Soc Jpn., (1979) 52(7): 1989-1993.
Iwata et al., "Asymmetric Functionalization at a Prochiral Carbon Center by the Aid of Sulfinyl Chirality: A Selective Formation of 6-Substituted (3R,Ss)—and (3S,Ss)-3-Hydroxymethyl-3,4-Dihydro-5-(p-Tolyl)Sulfinyl-2H-Pyrans," Tetra Lttrs. (1987) 28(27): 3131-3134.
Jacobsen et al., [Eds.] Comprehensive Asymmetric Catalysis—Catalysis I-III; Publisher: Springer (1999). (TOC only).
Jain et al., "Sulfonyl-Containing Aldophosphamide Analogues as Novel Anticancer Prodrugs Targeted against Cyclophosphamide-Resistant Tumor Cell Lines," J Med Chem. (2004) 47(15): 3843-3852.
Jones et al., "Minireview: nucleotide prodrugs", Antiviral Res. (1995) 27(1-2): 1-17.
Jones et al., "A Simple and Effective Method for Phosphoryl Transfer Using TiCl4 Catalysis" Org. Lett. (2002) 4(21): 3671-3673.

Jordheim et al., "Advances in the development of nucleoside and nucleotide analogues for cancer and viral diseases"., Nat Rev Drug Discov. 12(6):447-464.
Jounaidi et al., "Retroviral Transfer of Human Cytochrome P450 Genes for Oxazaphosphorine-based Cancer Gene Therapy," Cancer Res. (1998) 58(19): 4391-4401.
Jounaidi et al., "Frequent, Moderate-Dose Cyclophosphamide Administration Improves the Efficacy of Cytochrome P-450/Cytochrome P-450 Reductase-based Cancer Gene Therapy," Cancer Res. (2001) 61: 4437-4444.
Jung et al., "Hybridization of Alternating Cationic/Anionic Oligonucleotides to RNA Segments," Nucleosides and Nucleotides (1994) 13(6 & 7): 1597-1605.
Kachel et al., "Cyclophosphamide-Induced Lung Toxicity: Mechanism of Endothelial Cell Injury," J Pharmacol Exper Thera. (1994) 268(1): 42-46.
Keenan et al., "Pathology Reevaluation of the Kociba et al. (1978) Bioassay of 2,3,7,8-TCDD: Implications for Risk Assessment," J Tox Envir Health (1991) 34: 279-296.
Kelley et al., "[[(Guaninylalkl) phosphinico]methyl]phosphonic Acids. Multisubstrate Analogue Inhibitors of Human Erythrocyte Purine Nucleoside Phosphorylase," J Med Chem. (1995) 38(6): 1005-1014.
Khamnei et al., "Neighboring Group Catalysis in the Design of Nucleotide Prodrugs," J Med Chem. (1996) 39(20): 4109-4115.
Khorana et al., "Cyclic Phosphates. III. Some General Observations on the Formation andProperties of Five-, Six- and Seven-membered Cyclic Phosphate Esters," J Am Chem Soc. (1957) 79(2): 430-436.
Kim et al., "L-beta-(2S,4S)- and L-alpha-(2S,4R)-Dioxolanyl Nucleosides as Potential Anti-HIV Agents: Asymmetric Synthesis and Structure-Activity Relationships", J Med Chem. (1993) 36(5):519-528.
Kimura et al., "Studies on Nucleosides and Nucleotides. VII. 1) Preparation of PyrimidineNucleoside 5'-Phosphates and N3,5'-Purine Cyclonucleosides by Selective Activation of the 5'-Hydroxyl Group," Bull Chem Soc Jpn., (1979) 52(4): 1191-1196.
Kirschbaum, J., "Amantadine", Anal Prof Drug Subs. (1983) 12: 1-36.
Kirsten et al., "A General Strategy to Enantiomerically Pure Aliphatic and Olefinic Ketone Cyanohydrins by Stereoselective Alkylation of Umpoled Aldehyde Derivatives," J Org Chem. (1997) 62(20): 6882-6887.
Kobayashi et al., "Acylation of Active Methylene Compounds via Palladium Complex-Catalyzed Carbonylative Cross-Coupling of Organic Halides," Tetra Lttr., (1986) 27(39): 4745-4748.
Koh et al., "Design, Synthesis, and Antiviral Activity of Adenosine 5'-PhosphonateAnalogues as Chain Terminators against Hepatitis C Virus", J Med Chem. (2005) 48(8): 2867-2875.
Korba et al., "Liver-targeted Antiviral Nucleosides: Enhanced Antiviral Activity of Phosphatidyl-dideoxyguanosine in Woodchuck Hepatitis Virus Infection in Vivo," Hepatol. (1996) 25(5): 958-963.
Kramata et al., "9-(2-Phosphonylmethoxyethyl) derivatives of purine nucleotide analogs: A comparison of their metabolism and interaction with cellular DNA synthesis", Mol Pharmacol. (1999) 56(6): 1262-1270.
Kryuchkov et al., "Influence of Solvent on the Strength of Cyclic Oxygen-Containing Phosphorus Acids," Bull Acad SCI USSR, A translation of Izvestiya Akademii Nauk SSSR, Ser. Khim. (1987) 36(6) Part 1: 1145-1148.
Kuriyama et al., "Transient Cyclophosphamide Treatment Before Intraportal Readministration of an Adenoviral Vector can Induce Re-expression of the Original Gene Construct in Rat Liver," Gene Thera. (1999) 6: 749-757.
Kwon et al., "Effects of N-Substitution on the Activation Mechanisms of 4-Hydroxycylophosphamide Analogues," J Med Chem. (1989) 32(7): 1491-1496.
Larock R.C. [Ed.], "Comprehensive Organic Transformations—A Guide to Functional Group Preparations", VCH Publishers, Inc. (1989) TOC.
Latour et al., "Simple Synthesis of 2-hydroxymethyl-1, 3-propanediol and related compounds", Synthesis, 1987, 8: 742-745.
Lau et al., "Safety, Tolerability, Pharmacokinetics and Pharmacodynamics of Remofovir in Chronic HBV Patients in USA and Canada Following Daily Dosing for 28 Days," Presented at the 40th Annual

(56) References Cited

OTHER PUBLICATIONS

Meeting of EASL, Paris, France, J Hepatology 42(Suppl. 2)132, Abstract No. 74, Elsevier Ireland Ltd. (Apr. 2005).
Leach et al. "Toxicity Studies in Mice Treated with 1-β-D-Arabinofuranosyl-cytosine (ara-C)", Cancer Res. (1969) 29: 529-535.
Lefebvre et al., "Mononucleoside Phosphotriester Derivatives with S-acyl-2-thioethyl Bioreversible Phosphate-protecting Groups: Intracellular Delivery of 3'azido-2',3'dideoxythymidine 5'-monophosphate," J Med Chem. (1995) 38(20): 3941-3950.
Li et al., "Enantiomer/Enantiomer Interactions between the S-and R-Isomers of Omeprazole in Human Cytochrome P450 Enzymes: Major Role of CYP2C19 and CYP3A44," J Pharmacol Exp Ther. (2005) 315(2): 777-787.
Li et al., "Synthesis of D-arabinofuranosides Using Propane-1,3-diyl Phosphate as the Anomeric Leaving Group," Tetrahed Ltts. (2001) 42: 6615-6618.
Lieberman et al. [Eds.], "Pharmaceutical Dosage Forms—Tablets", Marcel Dekker, Inc. (1989) 2nd Edition; TOC.
Lilo et al., "Synthesis and Configurational Assignment of Bicyclic "Preactivated" Analogues of Cyclophosphamide," Tetra Lett. (1990) 31(6): 887-890.
Lin et al., "Comparative Disposition and Metabolic Profiles of [14C]Remofovir and [14C]Adefovir Dipivoxil in Rat Liver and Kidney," Abstracts of the 40th Annual Meeting of the European Association for the Study of the Liver, Paris, France, J Hepatology (2005) 42/2 Abstract #405.
Lin et al., "Development of Hepavir B, A Prodrug of PMEA with Excellent Liver-Targeting Properties," Abstracts of the 39th Annual Meeting of the EASL, Berlin, Germany, J Hapatology (2004) 40: Abs No. 374; p. 112.
Lin et al. "Single-Dose Pharmacokinetics and Metabolism of [$^{14}$C]Remofovir in Rats and Cynomolgus Monkeys" Antimicrobial Agents Chemother. (2005) 49(3): 925-930.
Lin et al., "Pradefovir is a Substrate, but Neither an Inhibitor nor an Inducer for Cytochrome P450," AASLD Abstracts, Hepatology (2005) 514A: Abstract No. 811; 1 page.
Lin et al., "Remofovir Mesylate: a Prodrug of PMEA with Improved LIver-Targeting and Safety in Rats and Monkeys," Antiviral Chem Chemother. (2004) 15: 307-316.
Lin et al., "Safety, Tolerance, Pharmacokinetics and Pharmacodynamics of Remofovir, A Liver-Targeting Prodrug of PMEA in HBV Patients Following Daily Dosing for 28 Days," AASLD Abstracts No. 1141, Hepatology(2004) 40(4 Suppl.): 659A; 2 pages.
Löhr et al., "Targeted chemotherapy by intratumor injection of encapsulated cells engineered to produce CYP2B1, and ifosfamide activating cytochrome P450," Gene Thera. (1998) 5: 1070-1078.
Lok et al., "Neurotoxicity associated with adenine arabinoside monophosphate in the treatment of chronic hepatitis B virus infection," J Antimicrob Chemother. (1984) 14: 93-99.
Lorey et al., "A New Cyclic Phosphoramidate D4T Prodrug Approach CycloAmb-D4T-Phosphoramidates," Nucleo Nucleo. (1999) 18(4 &5): 947-948.
Low et al., Conversion of 4-Hydroperoxycyclophosphamide and 4-Hydroxycyclophosphamide to Phosphoramide Mustard and Acrolein Mediated by Bifunctional Catalysts, Cancer Res. (1982) 42: 830-837.
Lown et al., "Grapefruit Juice Increases Felodipine Oral Availability in Humans by Decreasing Intestinal CYP3A Protein Expression," J Clin. Invest. (1997) 99: 2545-2553.
Lu et al., "Palladium-Catalyzed Reaction of Aryl Polyfluoroalkanesulfonates with O,O-Dialkyl Phosphonates", Synthesis (1987) 8: 726-727.
Ludeman et al., "Synthesis and Antitumor Activity of Cyclophosphamide Analogues. 1. Benzo Annulated Cyclophosphamide and Related Systems," J Med Chem. (1975) 18(12): 1251-1253.
Ludeman et al., "Synthesis and Antitumor Activity of Cyclophosphamide Analogues. 2. Preparation, Hydrolytic Studies, and Anticancer Screening of 5-Bromocyclophosphamide, 3,5-Dehydrocyclophosphamide, and Related Systems," J Med Chem. (1979) 22(2): 151-158.
Ludeman et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide," J Med Chem. (1986) 29(5): 716-727.
Ludeman et al., "Synthesis of Reactive Metabolite-Analogues of Cyclophosphamide for Comparisons of NMR Kinetic Parameters and Anticancer Screening Data," Drugs Exptl Clin Res. (1986) XII(6/7): 527-532.
Ma et al., "A Phase I/II Study to Assess the Safety, Tolerability and Pharmacokinetics (PK) of Intravenous (IV) Infusion of MB07133 in Subjects with Unresectable Hepatocellular Carcinoma (HCC) (Poster ID 2054, No. 19)", Poster Presentation; American Society of Clinical Oncology (ASCO) Conference, Atlanta, Georgia (Jun. 2006); 1 page.
MacKenna et al., "MB07133: A HepDirect(TM) Prodrug of Cytarabine Monophosphate for Use in Hepatocellular Carcinoma," Hepatol. (2003) 38(Suppl. 1):411A, AASLD Abstract No. 524, 1 page.
March, J. [Ed], "Effects of Structure on Reactivity" in Advanced Organic Chemistry, McGraw Hill Book Company, New York, (1977 2nd Ed.); Chapter 9, pp. 251-259.
Martin et al., "Synthesis and Antiviral Activity of Various Esters of 9-[1,3-Dihydroxyl-2-proposy)methyl]guanine," J Pharma Scie. (1987) 76(2): 180-184.
Marx et al., "Darmstoff analogues. 3. Actions of choline esters of acetal phosphatidic acids on visceral smooth muscle". J Med Chem. (1989) 32(6): 1319-1322.
Matsushima et al., "The nucleotide and deduced amino acid sequences of porcine liver proline-β-naphthylamidase," FEBS. (1991) 293(1-2): 37-41.
May-Manke et al., "Investigation of the Major Human Hepatic Cytochrome P450 Involved in 4-Hydroxylation and N-dechlorethylation of Trofosfamide," Cancer Chemother Pharmacol. (1999) 44: 327-334.
Maynard-Faure et al., "New Strategy for the Diastereoselective Synthesis of Bicyclic 'Pre-activiated' Analogues of Cyclophosphamide," Tetrahedron Lett. (1998) 39: 2315-2318.
McGuigan et al., "Intracellular Delivery of Bioactive AZT Nucleotides by Aryl Phosphate Derivatives of AZT," J Med Chem. (1993) 36(8): 1048-1052.
McGuigan et al., "Kinase Bypass: A new strategy for Anti-Hiv Drug Design," Bioorg Med Chem Lttrs. (1993) 3(6): 1207-1210.
McOmie J.F.W. [Ed.], "Protective Groups in Organic Chemistry", Plenum Press (1973); TOC.
Meek et al., "Synthesis of Inositol Phosphates", J Am Chem Soc. (1988) 110(7): 2317-2318.
Mei et al., Hollow mesoporous silica nanoparticles conjugated with pH-sensitive amphiphilic diblock polymer for controlled drug release, Microporous and Mesoporous Materials (2012) 152:16-24.
Meier et al., "Cyclic Saligenyl Phosphotriesters of 2',3'-Dideoxy-2',3'-didehydrothymidine (d4T)—A New Pro-Nucleotide Approach," Bioorg Med Chem Lttrs. (1997) 7(2): 99-104.
Meier et al. "ADA-Bypass by Lipophilic cycloSal-ddAMP Pro-Nucleotides. A Second Example of the Efficiency of the cycloSal-Concept", Bioorg Med Chem Lett. (1997) 7(12): 1577-1582.
Meijer et al., "Covalent and Noncovalent Protein Binding of Drugs: Implications for Hepatic Clearance, Storage, and Cell-Specific Drug Delivery," Pharm Res. (1989) 6(2): 105-118.
Mellor et al., "Aspects of the Chemistry of Dioxolanes: Synthesis of C-Nucleoside Analogues", Tetrahed. (1998) 54(1-2):243-256.
Melvin, "An Efficient Synthesis of 2-Hydroxyphenylphosphonates," Tetra Lttrs. (1981) 22(35): 3375-3376.
Merckling et al., "Diasteroselectivity in Nucleophilic Displacement Reactions at Phosphorus; Isolation and Characterization of a Pentacoordinated Intermediate," Tetrahed Ltts. (1996) 37(13): 2217-2220.
Meyer et al., "2-O'-Acyl-6-thioinosine Cyclic 3', 5'-Phosphates as Prodrugs of Thioinosinic Acid", J Med Chem. (1979) 22(7): 811-815.

(56) References Cited

OTHER PUBLICATIONS

Mikhailov et al., "Nucleoside Analogues on the Basis of 4(R), 5®-Dihydroxymethyl-2-Methyl-1, 3-Dioxolane", Nucleos Nucleot. (1994) 13(1-3):615-623.

Mikolajczyk et al., "Dimethyl Selenoxide Oxidation of Trivalent Phosphorus Compounds, Thio- and Selenophosphoryl Compounds, and Thiocarbonyl Compounds. Stercochemical Studies and Selective Modification of the Thiocarbonyl-Containing Nucleic Acid Components," J Org Chem., (1978) 43(11): 2132-2138.

Misiura et al., "Synthesis and Antitumor Activity of Analogues of Ifosfamide Modified in the N-(2-Chloroethyl) Group," J Med Chem. (1987) 31(1): 226-230.

Mitchell et al., "Acetaminophen-Induced Hepatic Necrosis. IV. Protective Role of Glutathione," J Pharm Exp Thera. (1973) 187(1): 211-217.

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J Chem Soc Perkin Trans. I. (1992) 2345-2353.

Mitsunobu, "The Use of Diethyl Azodicarboxylate and Triphenylphosphine in Synthesis and Transformation of Natural Products," Synthesis. (1981) 1981(1): 1-28.

Montag et al., "The Effect of Dexamethasone Treatment on CYP3A Activity Distribution, the Liver Targeting of MB07133 and CYP3A Activity in a Highly Proliferating State in Rats," Hepatol. (2004) 40(Suppl. 1): 649A, AASLD Abstract No. 1123, 1 page.

Moore et al., "Comparison of Mutagenicity results for Nine Compounds evaluated at the hgprt Locus in the Standard and Suspension CHO Assays," Mutagenisis (1991) 6(1): 77-85.

Moriarty et al., "Diphenyl Methylphosphonate as a Phosphonylation Reagent with High Diastereoselectivity at Phosphorus," Tetrahedron Lett. (1997) 38(15): 2597-2600.

Mosbo et al. "Dipole Moment, Nuclear Magnetic Resonance, and Infrared Studies ofPhosphorus Configurations and Equilibria in 2-R-2-Oxo-1,3,2-dioxaphosphorinanes," J Org Chem. (1977) 42(9): 1549-1555.

Mukaiyama, "The Directed Aldol Reaction", Org. React., (1982) 28: Chapter 3, pp. 203-251.

Mulato et al., "Nonsteroidal Anti-Inflammatory Drugs Effeciently Reduce the Transport andlCytotoxicity of Adefovir Mediated by the Human Renal Organic Anion Transporter 1," J Pharm Exp Ther. (2000) 295(1): 10-15.

Murono et al., "Prevention and inhibition of nasopharyngeal carcinoma growth by antiviral phosphonated nucleoside analogs," Cancer Res. (2001) 61(21): 7875-7877.

Murray et al., "Cytochrome P450 Expression is a common Molecular Event in Soft Tissue Sarcomas," J Phatol. (1993) 171: 49-52.

Murray et al., "Cytochrome P450 CYP3A in human renal cell cancer," Brit J Cancer (1999) 79(11/12): 1836-1842.

Naesens et al., "HPMPC (cidofovir), PMEA (adefovir) and Related Acyclic NucleosidePhosphonate Analogues: A Review of Their Pharmacology and Clinical Potential in the Treatment of Viral Infections," Antiviral Chem Chemother., (1997) 8(1): 1-23.

Naesens et al., "Therapeutic Potential of HPMPC (Cidofovir), PMEA (Adefovir) and Related Acyclic Nucleoside Phosphonate Analogues as Broad-Spectrum Antiviral Agents," Nucleosides Nucleotides. (1997) 16(7-9): 983-992.

Nagamatsu et al., "New Phosphorylating Agents for General Synthesis of Mixed Phosphate Esters," Tetrahedron Lett. (1987) 28(21): 2375-2378.

Nakayama et al., "A Highly Enantioselective Synthesis of Phosphate Triesters," J Am Chem Soc. (1990) 112(19): 6936-6942.

Neidlein et al., "Mild Preparation of 1-Benzyloxyiminoalkylphosphonic Dichlorides: Application to the Synthesis of Cyclic Phosphonic Diesters and Cyclic Monoester Amides," Heterocycles (1993) 35(2): 1185-1203.

Nema et al., "Excipients and their role in approved injectable products: Current Usage and Future Directions", PDA J Pharm Sci Technol. (2011) 65:287-332.

Nifant'Ev et al., et al., "Hexahydro-1,3,2,-Diazaphosphorines—II. Synthesis and Stereochemistry of Hexahydro-1,3-Dimethyl-1,3,4-Diazaphosphorines", J General Chemistry—USSR/Zh Obshch Khim., (1979) 49(1) Part 1: 53-61.

Nifantyev et al., "Synthesis and Structure of Some Stable Phospholane-Phospholanes," Phosphorus, Sulfur Silicon and Related Elements (1996) 113: 1-13.

Noble et al., "Adefovir Dipivoxil," Drugs. (1999) 58(3): 479-487.

Noyori et al., Asymmetric Catalysis on Organic Synthesis, (1994) John Wiley & Sons, Inc. (TOC only).

Ogg et al., "A reporter gene assay to assess the molecular mechanisms of xenobiotic-dependent induction of the human CYP3A4 gene in vitro," Xenobiotica (1999) 29(3): 269-279.

Ogilvie et al., A General Transesterification Method for the Synthesis of Mixed Trialkyl Phosphates, J Am Chem Soc. (1977) 99(1): 1277-1278.

Ohashi et al., "Synthesis of Phosphonosphingoglycolipid found in Marine Snail *Turbo cornutus*," Tetra Lttrs. (1988) 29(10): 1189-1192.

Oka et al., An oxazaphospholidine approach for the stereocontrolled synthesis of oligonucleoside phosphorothioates. J Am Chem Soc. (2003) 125(27):8307-8317.

Oliyai et al., "Kinetic Studies of the Degradation of Oxycarbonyloxymethyl Prodrugs of Adefovir and Tenofovir in Solution," Nucleosides, Nucleotides & Nucleic Acids, 20(4-7):1295-1298 (2001).

Ozaki et al., "Synthesis, Isolation and Characterization of Diastereochemically Pure Dithymidine Phosphormorpholidate Derivatives," Tetrahed Letts. (1989) 30(43): 5899-5902.

Ozaki et al., "Synthesis of Bis(deoxyribonucleoside) Phosphoromorpholidate Derivatives for Oligodeoxyribonucleotide Preparation by Use of a Selective Phosphitylating Reagent," Bull Chem Soc Jpn. (1989) 62(12): 3869-3876.

Ozoe et al., "Actions of cyclic esters, S-esters, and amides of phenyl-and phenylthiophosphonic acids on mammalia and insect GABA-gated chloride channels," Bioorg Med Chem. (1998) 6(1): 73-83.

Paine et al., "The Human Intestinal Cytochrome P450 'Pie'," Drug Metab Dispos. (2006) 34(5): 880-886.

Pankiewicz et al., "Nucleosides", J Org Chem. (1985) 50(18): 3319-3322.

Paquette et al., "Encyclopedia of Reagents for Organic Synthesis", John Wiley and Sons (1995); TOC.

Patois et al., "2-alkyl-5,5-dimethyl-1,3,2-dioxaphosphorinan-2-ones alpha-lithiated carbanions", J Chem Soc Perkin Trans. 1; (1990) 6: 1577-1581.

Patois et al., "Easy preparation of alkylphosphonyl dichlorides," Bull Soc Chim Fr. (1993) 130: 485-487.

Perich et al., "Di-tert-butyl N,N-Diethylphosphoramidite. A New Phosphitylating Agent for the Efficient Phosphorylation of Alcohols," Snthesis (1988) 1: 142-144.

Perich et al., "Synthesis of Casein-Related Peptides and Phosphopepties. V* The Efficient Global Phosphorylation of Protected Serine Derivatives and Peptides by Using Dibenzyl or Di-t-butyl N,N-Diethylphosphoramidite," Aust J Chem. (1990) 43(7-12): 1623-1632.

Perrillo et al., "A Multicenter United States—Canadian Trial to Assess Lamivudine Monotherapy before and after Liver Transplantation for Chronic Hepatitis B", Hepatol. (2001) 33(2): 424-432.

Petrakis et al., "Palladium-Catalyzed Substitutions of Triflates Derived from Tyrosine-Containing Peptides and Simpler Hydroxyarenes Forming 4-(Diethoxyphosphinyl) phenylalanines and Diethyl Arylphosphonates", J Am Chem Soc. (1986) 109(9): 2831-2833.

Pettit et al., "Antineoplastic agents 322. Synthesis of combretastatin A-4 prodrugs*," Anti-Cancer Drug Design. (1995) 10: 299-309.

Pilcher, "Built-In bypass," Nature (2004) 429: 39.

Plunkett et al. "Pharmacologically Directed Ara-C Therapy for Refractory Leukemia", Semin Oncol. (1985) 12(2) Supp. 3: 20-30.

Pogatchnik et al., "Enantioselective Synthesis of α-Hydroxy Phosphonates via Oxidation with (Camphorsulfonyl)oxaziridines," Tetrahedron Lett. (1997) 38(20): 3495-3498.

(56) References Cited

OTHER PUBLICATIONS

Posner et al., "3-Bromo-2-Pyrone: An Easily Prepared Chameleon Diene and a Synthetic Equivalent of 2-Pyrone in Thermal Diels-Alder Cucloadditions," Tetrahed Letts. (1991) 32(39): 5295-5298.
Postel et al., "Autocleavage of O-Isopropylidene Protected O-Phosphono- and O-Thionophosphono Esters of Sugars", J Carbohyd Chem. (2000) 19(2): 171-192.
Powell et al., "Compendium of excipients for parenteral formulations", PDA J Pharm Sci Technol. (1998) 52(5):238-311.
Predvoditelev et al., "Glycero-2-hydroxymethylene phosphates" J Org Chem.—USSR (1977) 13(8) Part1: 1489-1492.
Predvoditelev et al., "Synthesis of lipids and their models on the basis of glycerol alkylene phosphites. V. Cyclic phosphatidylglycerol and phosphatidylhydroxyhomocholine" J Org Chem.—USSR (1981) 17(6) Part 2: 1156-1165.
Prisbe et al., "Synthesis and Antiherpes Virus Activity of Phosphate and Phosphonate Deriviates of 9-[(1,3-Dihydorzy-2-propoxy)methyl]guanine", J Med Chem (1986) 29: 671-675.
Pubchem. SID 22395163; online: Feb. 23, 2007; NIH U.S. National Library of Medicine, [retrieved on Aug. 25, 2015]; 9 pages.
Quast et al., "Herstellung von Methylphosphonsäure-dichlorid," Synthesis, International Journal of Methods in Synthetic Organic Chemistry, 1974, p. 490.
Ramachandran et al., "Efficient General Synthesis of 1,2- and 1,3-diols in High Enantiomeric Excess via the Intramolecular Asymmetric Reduction of the Corresponding Ketoalkyl Diisopinocampheylborinate Intermediates," Tetra. Lttr. (1997) 38(5): 761-764.
Ramu et al., "Acrolein Mercaptures: Synthesis, Characterization, and Assessment of Their Role in the Bladder Toxicity of Cyclophosphamide," Chem Res TaxicoL. (1995) 8(4): 515-524.
Rao et al., "Studies Directed Towards The Synthesis of Immunosuppressive Agent FK-506 : Synthesis of The Entire Top-Half," Tetrahedron Letts. (1991) 32(4): 547-550.
Rathore et al., "Synthesis of aryl dichlorophospates using phase transfer catalysts", Indian J Chem B. (1993) 32(10): 1066-1067.
Rautio et al., "Prodrugs: design and clinical applications", Nature Rev Drug Disc. (2008) 7: 255-270.
Reddy et al., "Stereoselective Synthesis of Nucleoside Monophosphate HepDirect™ Prodrugs," Tetra Lttrs. (2005) 46: 4321-4324.
Reddy et al., "Development of a Quantum Mechanics-Based Free-Energy Perturbation Method: Use in the Calculation of Relative Solvation Free Energies", J Am Chem Soc.(2004) 126(20): 6224-6225.
Reddy et al., "Pradefovir (MB06866Q+): A Novel Hepatitis B Antiviral Therapy Using the HepDirect Prodrug Technology for Targeting Adefovir to the Liver," poster presented at the XVII International Roundtable on Nucleosides, Nucleotides and Nucleic Acids, Bern, Switzerland (Sep. 3-7, 2006).
Reddy et al., "HepDirect™ Prodrugs of Adefovir: Design, Synthesis and Optimization," Abstract for 227th ACS National Meeting in Anaheim, CA (Mar. 28-Apr. 1, 2004).
Redmore, "Phosphorus Derivatives of Nitrogen Heterocycles. 2. Pyridinephosphonic Acid Derivatives," J Org Chem. (1970) 35(12): 4114-4117.
Ren et al., "Inhibition of Human Aldehyde Dehydrogenase 1 by the 4-Hydroxycyclophosphamide Degradation Product Acrolein," Drug Metabol Disp. (1999) 27(1): 133-137.
Ren et al., "Pharmacokinetics of cyclophosphamide and its metabolites in bone marrow transplantation patients," Clinical Pharm Thera. (1998) 64(3): 289-301.
Roodsari et al., "A new approach to the stereospecific synthesis of Phospholipids, etc.", J Org Chem. (1999) 64(21): 7727-7737.
Roy et al., "Development of a Substrate-Activity Based Approach to Identify the Major Human Liver P-450 Catalysts of Cyclophosphamide and Ifosfamide Activation Based on cDNA-Expressed Activities and Liver Microsomal P-450 Profiles," Drug Metab Dispos. (Mar. 1999) 27(6): 655-666.

Russell et al., "Determination of 9-[(2-phosphonylmethoxy)ethyl]adenine in rat urine by high-performance liquid chromatography with fluorescence detection," J Chromatogr. (1991) 572(1-2): 321-326.
Rustum et al. "1 B-Arabinofuranosylcytosine in Therapy of Leukemia: Preclinical and Clinincal Overview," Pharmac Ther. (1992) 56: 307-321.
Sakamoto et al., "The Palladium-Catalyzed Arylation of 4H-1,3-Dioxin," Tetra Lttrs. (1992) 33(45): 6845-6848.
Sartillo-Piscil et al., "Fosfato-ésteres ciclicos diastereoisoméricos: 5-bromo-4-fenil-2-fenoxi-2-oxo-1,3,2-dioxafosforinanos, precursores de radicales libres alquilo β-fosfatoxi y generadores de radicales cationicos en medio no oxidativo," Rev. Soc. Quim. Mexico 46(4): 330-334, Journal of the Mexican Chemical Society (Dec. 2002); English translation.
Sasaki et al., "A General Method for Convergent Synthesis of Polycyclic Ethers Based on Suzuki Cross-Coupling: Concise Synthesis of the ABCD Ring System of Ciguatoxin", Org Letters (1999) 1(7):1075-1077 and Supporting Information.
Schlachter et al., "Anti-Inflammatory/Antiarthritic Ketonic Bisphosphonic Acid Esters," Bioorg Med Chem. Lett. (1998) 8(9): 1093-1096.
Schultz, "Prodrugs of Biologically Active Phosphate Esters" Bioorg Med Chem. (2003) 11: 885-898.
Schultze et al., "Practical Synthesis of the anti-HIV Drug, PMPA " Tetrahedron Lett. (1998) 39(14): 1853-1856.
Schwartz et al., "Cyclophosphamide Induces Caspase 9-Dependent Apoptosis in 9L Tumor Cells," Mol Pharmacol. (2001) 60(6): 1268-1279.
Serafinowska et al., "Synthesis and in Vivo Evaluation of Prodrugs of 9-[2-(Phosphonomethoxy)ethoxy]adenine," J Med Chem. (1995) 38: 1372-1379.
Shan et al., "Prodrug Strategies Based on Intramolecular cyclization Reactions," J Pharm Sci. (1997) 86(7): 765-767.
Shao et al., Synthesis of new cyclicphosphates of 3-hydroxyisoxazole and their diastereomers. Chin Chem Ltts (1993) 4(9):767-768.
Shaw et al., "Biological Screens of PMEA Prodrugs," Pharm Res. (1993) 10(10): S294, Contributed Papers Abstract No. PDD 7480.
Shaw et al., "Pharmacokinetics and Metabolism of Selected Prodrugs of PMEA in Rats," Drug Metabolism Dis. (1997) 25(3): 362-366.
Shen et al., "Nucleosides I. A New Synthesis of 1-β-D-Arabinofuranosyl Pyrimidine Nucleosides," J Org Chem. (1965) 30: 835-838.
Shiina et al., "An Effective Use of Benzoic Anhydride and Itds Derivatives for the Synthesis of Carboxylic Esters and Lactones: A Powerful and Convenient Mixed Anhydride method Promoted by Basic Catalysts", J Org Chem. (2003) 69(6):1822-1830 and Supporting Information.
Shih et al., "Preparation and Structures of 2-Dimethylamino-4-phenyl-1.3.2-dioxaphosphorinane-2-oxides," Bull Inst Chem Acad Sin. (1994) 41 : 9-16.
Shih et al., "Synthesis and Structure of 6-Phenylcyclophosphamides," Heterocycles (1986) 24(6): 1599-1603.
Shih et al., "Studies on Potential Antitumor Agents (III). Synthesis of 4-Arylcyclophosphamides", Heterocycles (1978) 9(9): 1277-1285.
Shimada et al., "Interindividual Variations in Human Liver Cytochrome P-450 Enzymes Involved in the Oxidation of Drugs, Carcinogens and Toxic Chemicals: Studies with Liver Microsomes of 30 Japanes and 30 Caucasians," J Pharmacol Exp Ther. (1994) 270: 414-423.
Shimma et al., "The Design and Synthesis of a New Tumor-Selective Fluoropyrimidine Carbamate, Capecitabine" Bioorg Med Chem. (2000) 8: 1697-1706.
Shirai et al., "Asymmetric Synthesis of Antimitotic CombretadioXolane with Potent Antitumor Activity Against Multi-Drug Resistant Cells," Bioorg Med Chem Lett (1998) 8: 1997-2000.
Shoshani et al., "Enzymatic synthesis of unlabeled and beta-32P-labeled beta-L-2',3'- dideoxyadenosine-5'-triphosphate . . . ", CAS Abstract Accession No. 1999:798820 in 2 pages.
Shoshani et al., "Enzymatic synthesis of unlabeled and beta-32P-labeled beta-L-2',3'- dideoxyadenosine-5'-triphosphate . . . ", J Biol Chem. 1999, 274(49):34735-34741.

(56) References Cited

OTHER PUBLICATIONS

Sinicrope et al., "Modulation of P-glycoprotein-mediated Drug Transport by Alterations in Lipid Fluidity of Rat Liver Canalicular Membrane Vescicles", J Biol Chem. (1992) 267(36): 24995-25002.
Sladek et al. "Influence of Diuretics on Urinary General Base Catalytic Activity and Cyclophosphamide-Induced Bladder Toxicity", Canc Treat Repts. (1982) 65(11): 1889-1990.
Sladek et al., "Restoration of Sensitivity to Oxazaphosphorines by Inhibitors of AldehydeDehydrogenase Activity in Cultured Oxazaphosphorine-resistant L 1210 and Cross-Linking Agent-resistant P388 Cell Lines1," Canc Res. (1985) 45: 1549-1555.
Slowinski et al., "Highly Stereoselective Induction in the Cobald-mediated [2+2+2] Cycloaddition of Chiral Phosphine Oxides Substituted Linear Enediynes", Tetrahedron Ltts. (1999) 40: 5849-5852.
Smolarek et al., "Metabolism and cytotoxicity of acetaminopen in hepatocyte cultures from rat, rabbit, dog, and monkey", Drug Metab Dispos. (1989) 18(5): 659-663.
Springate et al. "Toxicity of Ifosfamide and It's Metaboline Chloroacetaldehyde in Cultured Renal Tubule Cells", In Vitro Cell Dev Biol.—Animal (1999) 35: 314-317.
Starrett et al., "Synthesis, Oral Bioavailability Determination, and in Vitro Evalution of Prodrugs of the Antiviral Agent 9-[2-(Phosphonomethoxy)ethyl]adenine (PMEA)," J Med Chem. (1994) 37(12): 1857-1864.
Stepanov et al., "Total Syntheses of Chiral sn-myo-Inositol-1,4,5-Trisphosphate and its Enantiomer," Tetrahedron Letts. (1989) 30(38): 5125-5128.
Still et al., "Direct Synthesis of Z-Unsaturated Esters. A Useful Modification of The Horner-Emmons Olefination," Tetrahedron LettS. (1983) 24(41): 4405-4408.
Stella V.J., "Prodrugs as Therapeutics", Expert Opin. Ther. Patents (2004) 14(3): 277-280.
Stowell et al., "The Mild Preparation of Synthetically Useful Phosphonic Dichlorides: Application to the Synthesis of Cyclic Phosphonic Diesters and Diamides," Tetrahedron Letts. (1990) 31(23): 3261-3262.
Strömberg et al., "Iodide and Iodine Catalysed Phosphorylation of Nucleosides by Phosphorodiester Derivatives," Nucleo Nucleo. (1987) 6(5): 815-820.
Sullivan-Bolyai et al., "Safety, Tolerability, Antiviral Activity, and Pharmacokinetics of Pradefovir Mesylate in Patients with Chronic Hepatitis B Virus Infection: 24-Week Interim Analysis of a Phase 2 Study," AASLD Program, Hepatol. (2005) 78A: Abstract No. LB 07.
Sumida et al., "Quantitative Analysis of Constitutive and Inducible CYPs mRNA Expressionin the HepG2 Cell Line Using Reverse Transcription-Competitive PCR," Biochem Biophys Res Commun. (2000) 267(3): 756-780.
Suto et al. "The Effect of YNK-01 (an Oral Prodrug of Cytarabine) on Hepatocellular Carcinoma" Semin Oncol. (1997) 24(2) Suppl 6: S6-122 to S6-129.
Szymańska-Michalak et al., "New 3'-O-aromatic acyl-5-fluoro-2'-deoxyuridine derivatives as potential anticancer agents". Eur J Med Chem. (2016) 115:41-52.
Taapken et al., "Stereoselective Synthesis of Homochrial (E)-Vinyl Phosphonates Derived from (-)-Ephedrine," Tetrahedron Letts. (1995) 36(37): 6659-6662.
Takaku et al., "Synthesis of Bis(5-chloro-8-quinolyl) Nucleoside 5'-Phosphates in Oligoribonucleotide Systhesis by the Phosphotriester Approach," J Org Chem. (1982) 47(25): 4937-4940.
Takaku et al., "Synthesis of Deoxyribooligonucleotides Using Cesium Fluoride by the Phosphotriester Approach," Nippon Kagaku Kaisha (1985) 10: 1968-1973, The Chemical Society of Japan, Inc.; English Translation.
Takaku et al., "Use of 2-(2-Pyridyl) Ethyl Group as a new Protecting Group of Internucleotidic Phosphates in Oligonucleotide Synthesis", Chem Lttrs. (1986) 5: 699-702.
Tawfik et al., "1,8-Diazabicyclo[5.4.0]undecene Mediated Transesterification of p-Nitrophenyl Phosphonates: A Novel Route to Phosphono Esters," Synthesis (1993) 10: 968-972.

Ten Hoeve et al.: "The Design of Resolving Agents Chiral Cyclic Phosphoric Acids," J Org Chem. (1985) 50(23): 4508-4514.
Thomson et al., "Synthesis, Bioactivation and Anti-HIV Activity of the Bis(4-acyloxybenzyl) and Mono(4-acyloxybenzyl) Esters of the 5'-monophosphate of AZT," J Chem Soc. Perkin Trans. I. (1993) 2/06723D: 1239-1245.
Thuong et al., "Nouvelle méthode de préparation de la phosphorylcholine, de laphosphorylhomocholine et de leurs dérivés," Bull Soc Chim France, (1974) No. 130; 1-2: 667-671; English translation.
Torneiro et al., "A Short, Efficient, Copper-Mediated Synthesis of 1alpha, 25-Dihydroxyvitamin D2 (1alpha, 25-Dihydroxyergocalciferol) and C-24 Analogs", J Org Chem. (1997) 62(18): 6344-6352.
Tullis et al., "Reagent Control of Geometric Selectivity and Enantiotopic Group Preference in Asymmetric Horner-Wadsworth-Emmons Reactions with meso-Dialdehydes," J Org Chem. (1998) 63(23): 8284-8294.
Turner et al., "Acylation of Ester Enolates by N-Methoxy-N-methylamides: An Effective Synthesis of beta-Keto Esters", J Org Chem. (1989) 54(17): 4229-4231.
Turner J. A., "A General Appproach to the Synthesis of 1,6-, 1,7-, and 1,8-Naphthyridines," J Org Chem. (1990) 55(15): 4744-4750.
Vaccaro et al., "Lipid based nanovectors containing ruthenium complexes: a potential route in cancer therapy". Chem Commun (Camb). (2009) 11:1404-1406.
Valentine Jr., "Preparation of the Enantiomers of Compounds Containing Chiral Phosphorus Centers," Asym Synth. (1984) 41: 263-312.
Van Haperen et al., "Induction of Resistance to 2',2'-Difluorodeoxycytidine in the Human Ovarian Cancer Cell Line A2780", Semin Oncol. 22 Suppl. (1995) 11(4): 35-41.
Van Poelje et al., "MB6866 (Hepavir B), A HepDirectTM Prodrug of Adefovir: Mechanism of Activation and Liver Targeting," AASLD Abstracts, Hepatology (2003) 706A:Abstract No. 1143.
Vankayalapati et al., "Stereoselective synthesis of alpha-L-Fucp-(1,2)- and -(1,3)-beta-D-Galp(1)-4-methylumbelliferone using glycosyl donor substituted by propane-1,3-diyl phosphate as leaving group", J Chem Soc Perkin Trans J. (2000) 14: 2187-2193.
Venook, "Treatment of Heptacellular Carcinoma: Too Many Options?" J Clin Oncol. (1994) 12(6): 1323-1334.
Verfürth et al., "Asymmetrische Synthese chiraler Phosphorverbindungen durch destruktiv-selektive Oxidation von P(III)-Verbindungen mittels chiraler Oxaziridine," Chem. Ber. (1991) 124(7): 1627-1634.
Vitarella et al. "Hepavir B, A CYP3A4-Activated Prodrug of PMEA, Showed Better Safety then Hepsera in Pre-Clinical Studies" Abstract #995 of the 43rd Annual Meeting of the Society of Toxicology, Baltimore, MD (Mar. 2004).
Vo-Quang et al., "(1-Amino-2-propenyl) Phosphonic Acid, and Inhibitor of Alanine Racemase and D-Alanine:D-Alanine Ligase.," J Med Chem. (1986) 29(4): 579-581.
Wacher et al., "Active Secretion and Enterocytic Drug Metabolism Barriers to Drug Absorption," Adv Drug Del Rev. (2001) 46: 89-102.
Wada et al., "Nucleoside 3'-N,N-Dialkyphosphonamidates: Novel Building Blocks for Oligonucleotide Synthesis," Tetrahedron Letts. (1990) 31(44): 6363-6366.
Waga et al., "Synthesis of 4'-C-Methylnucleosides", Biosci Biotech Biochem. (1993) 57(9): 1433-1438.
Wagner et al., "Direct Conversion of Tetrahydropyranylated Alcohols to the Corresponding Bromides," Tetra Lttrs. (1989) 30(5): 557-558.
Wallace et al., "Design and Synthesis of Potent, Selective Inhibitors of Endothelin-Converting Enzyme," J Med Chem (1998) 41(9): 1513-1523.
Walsh et al. "Phenoxymethylphosphonic Acids and Phosphonic Acid Ion-exchange Resins," J Am Chem Soc. (1956) 78: 4455-4458.
Watanabe et al., "Dibenzyl Phosphorofluoridate, A New Phosphorylating Agent," Tetrahedron Letts. (1988) 29(45): 5763-5764.
Watanabe et al., "A Short Step and Practical Synthesis of MYO-Inositol 1,3,4,5-Tetrakisphosphate," Chem Pharm Bull. (1990) 38(2): 562-563.

(56) References Cited

OTHER PUBLICATIONS

Watkins et al., "Noninvasive tests of CYP3A enzymes," Pharmacogenetics (1994) 4: 171-184.
Weber et al., "Activation of the Anti-cancer Drug Ifosphamide by Rat Liver Microsomal P450 Enzymes," Biochem Pharm. (1993) 45(8): 1685-1694.
Wechter et al., "Nucleic Acids, 16. Orally Active Derivatives of ara-Cytidine", J Med Chem. (1976) 19(8), 1013-1017.
Wedmid et al., "Long-Chain Steromeric 2-Alkyl-4-methozycarbonyl-1,3-dioxolanes in Glyceraol Acetal Synthesis", J Org Chem. (1977) 42(22):3624-3626.
Weibel et al., "Potentiating Effect of {2-[2-[(2-Amino-1,6-Dihydro-6-oxo-9H-Purin-9-yl) Methyl]-Phenyl]Ethenyl}-Phosphonic Acid (MDL 74,428), A Potent Inhibitor of Purine Nucleoside Phosphorylase, on the Antiretroviral Activities of 2',3''-Dideoxyinosine Combined to Ribavirin in Mice," Biochem Pharmacol. (1994) 48(2): 245-252.
Weinhardt et al., "Synthesis and antidepressant Profiles of Phenyl-Substituted 2-Amino- and 2-[(Alkoxycarbonyl)amino]-1,4,5,6-tetrahydropyrimidines1," J Med Chem. (1985) 28: 694-898.
Welch et al., "The Stereochemistry of the Aryl Phosphate/Aryl Phosphonate Rearrangement in 1,3,2-Oxazaphospholidine 2-Oxides," J Org Chem. (1990) 55(24): 5991-5995.
Werle et al., "Synthese der Dimethylolessigsäure," Liebigs. Ann. Chem., 1986, pp. 944-946.
Wileman et al., "Receptor-mediated endocytosis," Biochem J. (1985) 232: 1-14.
Wolfe et al., "A Concise Synthesis of 2'-C-Methylribonucleosides", Tetrahedron Lttrs. (1995) 36(42): 7611-7614.
Wolff M. E. [Ed] "Burger's Medicinal Chemistry And Drug Discovery, 5ed, Part I", John Wiley & Sons, 1995, pp. 975-977.
Woźniak et al., "Oxidation in Organophosphorus Chemistry: Potassium Peroxymonosulphate", Tetrahedron Letts. (1999) 40(13): 2637-2640.
Xu et al. "Toxicokinetics of Adefovir Dipivoxil and Remofovir in 28-Day Toxicity Studies" Abstract #PB-P009 of the 64th International Congress FIP World Congress of Pharmacy and Pharmaceutical Science, New Orleans, LA (Sep. 2004).
Xu et al., "Toxicokinetics of Remofovir in Mice, Rats and Monkeys After Repeated Oral Administrations" Abstract #PB-P008 of the 64th International Congress FIP World Congress of Pharmacy and Pharmaceutical Science, New Orleans, LA (Sep. 2004).
Yamakage et al., "1, 1, 1,3,3,3-Hexafluoro-2-Propyl Group as a New Phosphate Protection|Group for Oligoribonucleotide Synthesis in the Phosphotriester Approach," Tetrahedron (1989) 45(17): 5459-5468.
Yamamoto et al., "Synthesis of Pyridine N-Oxide-SbC15 Complexes and Their Intramolecular and Oxygen-Transfer Reaction," Tetra Lttrs. (1981) 37: 1871-1873.
Yamanaka et al., "Metabolic Studies on BMS-200475, a New Antiviral Compound Active against Hepatitis B Virus", Antimicrob Agents Chemother. (1999) 43(1): 190-193.
Yang et al., Accession No. 1974:421578 CAPLUS, "Effects of guanosine tetraphosphate et al.", XP-002777343 in 1 page.
Yang et al., "Effects of Guanosine Tetraphosphate, Guanosine Pentaphosphate, and β-γMethylenyl-Guanosine Pentaphosphate on Gene Expression of *Escherichia coli* In Vitro" Proc. Nat. Acad. Sci. USA. vol. 71, No. 1, pp. 63-67, Jan. 1974.
Yip et al. "Use of High-Performance Liquid Chromatography in the Preparation of Flavin Adenine Dinucleotide Analyte Conjugates," J Chromatography (1985) 326: 301-310.
Yoshida et al., "Participation of the Peroxisomal β-Oxidation System in the Chain-Shortening of PCA16, A Metabolite of the Cytosine Arabinoside Prodrug, YNKO1, in Rat Liver," Biochem Pharmacol. (1990) 39(10): 1505-1512.
Yu et al., "In Vivo Modulation of Alternative Pathways of P-450-Catalyzed Cyclophosphamide Metabolism: Impact on Pharmacokinetics and Antitumor Activity," J Pharm Exp Ther. (1999) 288(3): 928-937.

Yule et al., "The Effect of Fluconazole on Cyclophosphamide Metabolism in Children," Drug Metabo Disp. (1999) 27(3): 417-421.
Zahran et al., "The Potential of Aspirin in Prodrug Synthesis: A New Potential Delivery System of ACT and FLT", Arch Pharm Pharm Med Chem. (1996) 329:417-420.
Zhou et al., "IDX184, A liver-targeted Nucleotide HCV Polymerase Inhibitor: Results of a First-in-Man Safety and Pharmacokinetic Study", Poster No. 966; 44th Annual Meeting European Association for the Study of the Liver (EASL); Copenhagen, Denmark Apr. 22-26, 2009; 1 page.
Zon G., "Cyclophosphamide Analogues", Progress Med Chem. Ellis G.P. et al. [Eds] (1982) 19: 205-246.
Zon et al., "NMR Spectroscopic Studies of Intermediary Metabolites of Cyclophosphamide. A Comprehensive Kinetic Analysis of the Interconversion of cis- and trans-4-Hydroxycyclophosphamide with Aldophosphamide and Concomitant Partitioning of Adophosphamide Between Irreversible Fragmentation and Reversible Conjugation Pathways," J Med Chem. (1984) 27(4): 466-485.
Das U.N., "Essential Fatty Acids and Their Metabolites Could Function as Endogenous HMG-COA Reductase . . . ", Lipids Health Dis. (2008) 7(37) in 18 pages.
Evans "Chemistry 206 Advanced Organic Chemistry", Harvard University, [online] Fall 2002 Lectures and Handouts; [retrieved via Wayback Machine on Feb. 14, 2003]; from the internet, <http://www.courses.fas.harvard.edu/~chem206/Fall-2003/Lectures-and-Handouts/>; in 2 pages.
Fang C., et al. "Liver-Targeting Prodrug of PMEA Induces a Much More Favorable Kidney and Liver Toxicological Gene Expression-in Rats Compared to BisPOM-PMEA" Abstract #1274, 42nd Annual Meeting of the Society of Toxicology, Salt Lake City, UT (Mar. 9-13, 2003).
Fang C., et al., "Renal Toxicological Gene Response to Anti-Hepatitis B Prodrugs Hepavir B and Hepsera in Rats" Abstract #1472, 43rd Annual Meeting of the Society of Toxicology, Baltimore, MD (Mar. 21-25, 2004).
Ferroni et al., "A Three-step Preparation of Dihydroxyacetone Phosphate Dimethyl Acetal", J Org Chem. (1999) 64(13): 4943-4945.
Gensler et al., "Configuration of 9,10-Dihydroxystearic Acid", J Am Chem Soc. (1956) 78(1): 169-172.
Hanaoka et al., "Transformation of 2,3,9,10--tetraoxygenated protoberberine alkaloids into 2,3, 10, 11-tetraoxygenated protoberberine alkaloids", Heterocycles (1985) 23(11): 2927-2930.
Harry-O'Kuru et al., "A short, flexible route toward 2'-C-branchedribonucleosides", J Org Chem. (1997) 62(6): 1754-1759.
Kim et al., "Synthesis and Biological Activities of Phosphonylalkylpurine Derivatives," Nucleosides & Nucleotides (1989) 8(5-6): 927-931.
Krise et al., "Prodrugs of phosphates, phosphonates, and phosphinates," Adv Drug Del Rev. (1996) 19(2): 287-310.
Reusch, W., "Virtual Text of Organic Chemistry," Michigan State University, [online] Aug. 1, 2004, [retrieved on Jan. 19, 2005]. Retrieved from the internet, <http://www.cem.msu.edu/%7Ereusch/VirtualText/speciall2.htm#topl>; TOC in 2 pages.
Robins et al., Design and synthesis of beta-D-ribofuranosyl nucleosides active against RNA viral infections, Adv Antiviral Drug Design. (1993) 1: 39-85.
Sales-Campos et al., "An Overview of the Modulatory Effects of Oleic Acid in Health and Disease", Med Chem. (2013) 13(2): 201-210.
Schmidt et al., "Identification of a New Member of the Steroid Hormone Receptor Superfamily that is Activated by a Peroxisome Proliferator and Fatty Acids", Mol Endocrinol. (1992) 6(10): 1634-1641.
Silverberg et al., "A simple, rapid and efficient protocol for the selective phosphorylation of phenols with dibenzyl phosphite", Tetrahedron Lttrs. (1996) 37(6): 771-774.
European Examination Report dated Aug. 16, 2021 in Application No. 19738393.8.
European Examination Report dated Jun. 15, 2022 in Application No. 19738393.8.

(56) References Cited

OTHER PUBLICATIONS

Eriguchi et al., "Studies on Hypolipidemic Agents. I. Synthesis of 1,3-Dioxolanes and 1,3-Dioxanes." Chem Pharm Bull. Feb. 25, 1982; 30(2): 428-439.
Sasaki et al., "Total Synthesis and Bioactivities of Two Proposed Structures of Maresin." Chemistry—An Asian Journal. Feb. 1, 2011;6(2): 534-543.
Japanese Office Action dated Feb. 6, 2023 for Application No. 2020-527621, filed Jul. 7, 2020.

* cited by examiner

ACETAL COMPOUNDS AND THERAPEUTIC USES THEREOF

CROSS REFERENCE TO RELATED APPLICATIONS

This application is a U.S. National Phase of International Application No. PCT/US2019/012762, filed on Jan. 8, 2019 and published on Jul. 18, 2019 as WO 2019/139919, which claims the benefit of U.S. Provisional Application No. 62/615,357 filed Jan. 9, 2018 entitled "ACETAL COMPOUNDS AND THERAPEUTIC USES THEREOF", which is incorporated by reference in its entirety.

BACKGROUND

Field

The present disclosure relates to the field of chemistry and medicine. More specifically, the present disclosure relates to acetal and cyclic acetal compounds, compositions, their preparation, and their use as therapeutic agents.

Description of the Related Art

Statins are a class of liver-targeting compounds that inhibit HMG-CoA reductase, one of the liver enzymes in the cholesterol biosynthetic pathway. Statins are used as lipid-lowing medicines for the prophylactic and therapeutic treatment of coronary heart disease. Despite their ubiquitous use, statins, like other liver-targeting drugs, suffer from poor oral bioavailability and inadequate distribution to the liver. In fact, a significant portion of patients cannot take statins because of side effects from statin biological activity outside of the liver.

Thus, there is a need for improved liver-targeting compounds and strategies to increase the bioavailability of liver-targeting drugs, to increase drug distribution to the liver, and to reduce drug biological activity outside of the liver.

SUMMARY

Some embodiments described herein relate to compounds having the structure of Formula I:

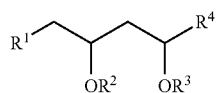

I or a pharmaceutically acceptable salt thereof, wherein $R^1$, $R^2$, $R^3$, and $R^4$ have any of the values described herein.

In some embodiments, $R^1$ is selected from the group consisting of optionally substituted $C_{1-8}$alkyl, —COOR$^5$, optionally substituted $C_{2-10}$alkoxyalkyl, and optionally substituted 3-12 membered heterocyclyl. Alternatively, in some embodiments, $R^1$ and $R^2$ together with the atoms to which they are attached form an optionally substituted 4-10 membered heterocyclyl, or $R^1$ and $R^3$ together with the atoms to which they are attached form an optionally substituted 6-10 membered heterocyclyl.

$R^2$ in some embodiments is selected from the group consisting of H, —C(O)R$^6$, and optionally substituted $C_{2-10}$alkoxyalkyl. Alternatively, in some embodiments, $R^1$ and $R^2$ together with the atoms to which they are attached form an optionally substituted 4-10 membered heterocyclyl, or $R^2$ and $R^3$ together with the atoms to which they are attached form a 6-10 membered heterocyclyl, optionally substituted with one or more $R^7$.

In some embodiments, $R^3$ is selected from the group consisting of H, —C(O)R$^8$, and optionally substituted $C_{2-10}$alkoxyalkyl. Alternatively, in some embodiments, $R^1$ and $R^3$ together with the atoms to which they are attached form an optionally substituted 6-10 membered heterocyclyl, or $R^2$ and $R^3$ together with the atoms to which they are attached form a 6-10 membered heterocyclyl, optionally substituted with one or more $R^7$.

$R^4$ in some embodiments is a fragment of a therapeutic agent.

In some embodiments, each of $R^5$, $R^5$, and $R^8$ is independently selected from the group consisting of H, optionally substituted $C_{1-6}$alkyl, halogen, optionally substituted $C_{2-6}$alkenyl, optionally substituted $C_{2-6}$alkynyl, optionally substituted $C_{3-7}$carbocyclyl, optionally substituted $C_{6-10}$aryl, optionally substituted 5-10 membered heteroaryl, and optionally substituted 3-10 membered heterocyclyl.

In some embodiments, each $R^7$ is independently selected from the group consisting of optionally substituted $C_{1-8}$alkyl, oxo, optionally substituted $C_{6-18}$aryl, and optionally substituted 5-18 membered heteroaryl.

In some embodiments, at least one of $R^2$ and $R^3$ is not or $R^1$ is not —COOH. Moreover, in some embodiments, if $R^1$ and $R^3$ together with the atoms to which they are attached form a 6 membered heterocyclyl, then $R^2$ is not H.

Some embodiments described herein relate to compounds having the structure of Formula II:

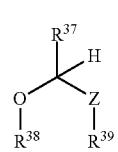

II or a pharmaceutically acceptable salt thereof, wherein $R^{37}$, $R^{38}$, $R_{39}$, and Z have any of the values described herein.

In some embodiments, Z is O, S, or $NR^{40}$.

$R^{37}$ in some embodiments is selected from the group consisting of H, a fragment of a therapeutic agent, optionally substituted $C_{1-8}$alkyl, $C_{1-6}$haloalkyl, $C_{1-6}$heteroalkyl, optionally substituted $C_{3-7}$carbocyclyl, optionally substituted 3-10 membered heterocyclyl, optionally substituted $C_{6-18}$aryl, 5-10 membered heteroaryl, and optionally substituted $C_{2-10}$alkoxyalkyl.

In some embodiments, each of $R^{38}$ and $R^{39}$ is independently selected from the group consisting of a fragment of a therapeutic agent, optionally substituted $C_{1-6}$alkyl, $C_{1-6}$haloalkyl, $C_{1-6}$heteroalkyl, optionally substituted $C_{3-7}$carbocyclyl, optionally substituted 3-10 membered heterocyclyl, optionally substituted $C_{6-18}$aryl, optionally substituted $C_{2-10}$alkoxyalkyl and optionally substituted 5-10 membered heteroaryl.

In some embodiments, at least one of $R^{37}$, $R^{38}$, and $R^{39}$ is a fragment of a therapeutic agent.

In some embodiments, the fragment of a therapeutic agent is further optionally substituted with one or more moieties selected from the group consisting of

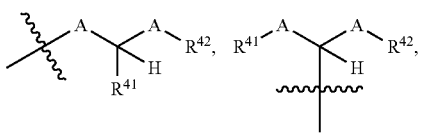

$C_{1-6}$alkyl, halo, and $C_{6-18}$aryl. In some such embodiments, each A is independently selected from O, S, and $NR^{43}$, provided that at least one A is O. In some such embodiments, each of $R^{41}$, $R^{42}$, and $R^{43}$ is independently selected from the group consisting of H, optionally substituted $C_{1-6}$alkyl, $C_{1-6}$haloalkyl, $C_{1-6}$heteroalkyl, optionally substituted $C_{3-7}$carbocyclyl, optionally substituted 3-10 membered heterocyclyl, optionally substituted $C_{6-18}$aryl, optionally substituted $C_{2-10}$alkoxyalkyl, and optionally substituted 5-10 membered heteroaryl.

In some embodiments, $R^{40}$ is independently selected from the group consisting of optionally substituted $C_{1-6}$alkyl, $C_{1-6}$haloalkyl, $C_{1-6}$heteroalkyl, optionally substituted $C_{3-7}$carbocyclyl, optionally substituted 3-10 membered heterocyclyl, optionally substituted $C_{6-18}$aryl, optionally substituted $C_{2-10}$alkoxyalkyl, and optionally substituted 5-10 membered heteroaryl.

DETAILED DESCRIPTION

Compounds of Formula I and II

In some embodiments, liver-targeting compounds containing an acetal moiety are provided that afford increased bioavailability relative to their active drug counterparts, increased drug distribution to the liver relative to their active drug counterparts, and/or reduced biological activity outside of the liver.

Various embodiments of these compounds include compounds having the structures of Formula I or II as described above or pharmaceutically acceptable salts thereof. In some embodiments, the compounds of Formula I are also represented by the structure of Formula Ia, Ib, Ic, Id, Ie, If, or Ig:

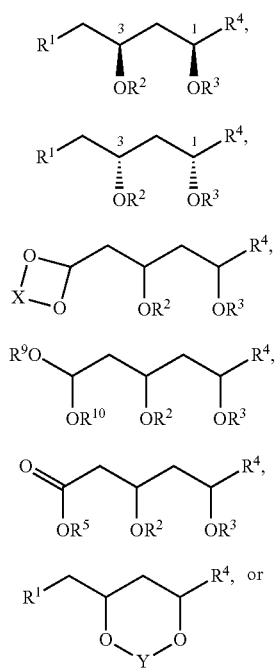

or pharmaceutically acceptable salts thereof, wherein R1, R2, R3, R4, R5, R6, R7, R8. R9, R10, R11, R12, R13, R14, R15, R16, R17, R18, R19, R20, R21, R22, R23, R24, R25, R26, R27, R28, R29, R30, R31, R32, R33, R34, R35, R36, X, and Y have any of the values described herein.

In some embodiments of the compounds of Formula Ic, X is an optionally substituted C1-7alkylene linker. In some such embodiments, X is a C1-7alkylene linker optionally substituted with one or more R11. In some such embodiments, R11 is selected from the group consisting of C1-6alkyl, C1-6alkenyl, C1-6alkynyl, C1-6heteroalkyl, C3-7carbocyclyl, 3-10 membered heterocyclyl, C6-18aryl, C6-18arylC1-6alkyl, 5-10 membered heteroaryl, 5-10 membered heteroarylC1-6alkyl, halo, cyano, hydroxy, C1-6alkoxy, C2-10alkoxyalkyl, C6-18aryloxy, sulfhydryl, haloC1-6alkyl, haloC1-6alkoxy, C1-6alkylthio, C6-18arylthio, and nitro. In some such embodiments, R11 is selected from the group consisting of C1-6alkyl, C3-7carbocyclyl, C1-6alkoxy, C6-18aryl, or halo. In some further embodiments, X is a C2alkylene linker. In some particular embodiments, X is —CH2CH2—. In some further embodiments, X is a C3alkylene linker. In some particular embodiments, X is —CH2CH2CH2—. In some particular embodiments, X is —CH2(CH2CH3)CH2—. In other particular embodiments, X is —CH2(CH3)CH2CH2(CH3)—.

In some embodiments of the compounds of Formula Id, each of R9 and R10 is independently an optionally substituted C1-6alkyl. In some such embodiments, each of R9 and R10 is independently a C1-6alkyl optionally substituted with one or more R12. In some such embodiments, R12 is selected from the group consisting of C1-6alkyl, C1-6alkenyl, C1-6alkynyl, C1-6heteroalkyl, C3-7carbocyclyl, C3-7carbocyclylC1-6alkyl, 3-10 membered heterocyclyl, 3-10 membered heterocyclylC1-6alkyl, C6-18aryl, C6-18arylC1-6alkyl, 5-10 membered heteroaryl, 5-10 membered heteroarylC1-6alkyl, and haloC1-6alkyl. In some further embodiments, R9 is a C1-6alkyl. In some particular embodiments, R9 is ethyl. In some further embodiments, R10 is a C1-6alkyl. In some particular embodiments, R10 is ethyl.

In some embodiments of the compounds Formula If, Y is a C1-5alkylene linker, optionally substituted with one or more R7. In some such embodiments, R7 is selected from the group consisting of optionally substituted C1-8alkyl, oxo, optionally substituted C6-18aryl, and optionally substituted 5-18 membered heteroaryl. In some further embodiments, Y is a C1alkylene linker.

In some embodiments of the compounds of Formula I, Ia, Ib, or If, R1 is an optionally substituted C1-8alkyl. In some such embodiments, R1 is a C1-8alkyl optionally substituted with one or more R13. In some such embodiments, R13 is selected from the group consisting of halo, cyano, hydroxy, C1-6alkoxy, C6-10aryloxy, sulfhydryl, haloC1-6alkoxy, C1-6alkylthio, C6-10arylthio, and nitro. In some particular embodiments, R1 is —CH2OH.

In some embodiments of the compounds of Formula I, Ia, Ib, or If, R1 is —COOR5. In some such embodiments, R5 is H. In other such embodiments, R5 is methyl.

In some embodiments of the compounds of Formula I, Ia, Ib, or If, R1 is an optionally substituted C2-10alkoxyalkyl. In some such embodiments, R1 is a C2-10alkoxyalkyl optionally substituted with one or more R14. In some such embodiments, R14 is selected from the group consisting of halo, cyano, hydroxy, C1-6alkoxy, C6-10aryloxy, sulfhydryl, haloC1-6alkoxy, C1-6alkylthio, C6-10arylthio, and nitro. In some particular embodiments, R1 is —CH2OCH2OCH2CH3. In some particular embodiments, R1 is —CH(OCH2CH3)2.

In some embodiments of the compounds of Formula I, Ia, Ib, or If, R1 is an optionally substituted 3-12 membered heterocyclyl. In some such embodiments, R1 is a 3-12 membered heterocyclyl optionally substituted with one or more R15. In some such embodiments, R15 is selected from the group consisting of C1-6alkyl, C1-6alkenyl, C1-6alkynyl, C1-6heteroalkyl, C3-7carbocyclyl, 3-10 membered heterocyclyl, C6-18aryl, C6-18arylC1-6alkyl, 5-10 membered heteroaryl, 5-10 membered heteroarylC1-6alkyl, halo, cyano, hydroxy, C1-6alkoxy, C2-10alkoxyalkyl, aryloxy, sulfhydryl, haloC1-6alkyl, haloC1-6alkoxy, C1-6alkylthio, C6-18arylthio, and nitro. In some further embodiments, R1 is a 5 membered heterocyclyl. In some particular embodiments, R1 is

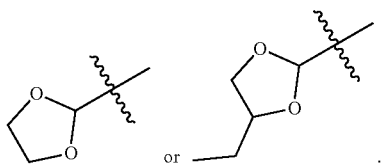

In some further embodiments, R1 is a 6 membered heterocyclyl. In some particular embodiments, R1 is

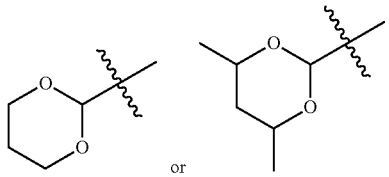

In some embodiments of the compounds of Formula I, Ia, Ib, Ic, Id, or Ie, R2 is H.

In some embodiments of the compounds of Formula I, Ia, Ib, Ic, Id, Ie, or Ig, R2 is —C(O)R6. In some such embodiments, R6 is an optionally substituted C1-6alkyl. In some such embodiments, R6 is a C1-6alkyl optionally substituted with one or more R16. In some such embodiments, R16 is selected from the group consisting of halo, cyano, hydroxy, C1-6alkoxy, C6-10aryl, C6-10aryloxy, sulfhydryl, haloC1-6alkoxy, C1-6alkythio, C6-10arylthio, and nitro. In some particular embodiments, R6 is —CH(CH3)2.

In some embodiments of the compounds of Formula I, Ia, Ib, Ic, Id, Ic, or Ig, R2 is an optionally substituted C2-10alkoxyalkyl. In some such embodiments, R2 is a C2-10alkoxyalkyl optionally substituted with one or more R17. In some such embodiments, R17 is selected from the group consisting of halo, cyano, hydroxy, C1-6alkoxy, C6-10aryl, C6-10aryloxy, sulfhydryl, haloC1-6alkoxy, C1-6alkylthio C6-10arylthio, and nitro. In some particular embodiments, R2 is —CH2OCH2CH3.

In some embodiments of the compounds of Formula I, Ia, Ib, Ic, Id, or Ie, R3 is H.

In some embodiments of the compounds of Formula I, Ia, Ib, Ic, Id, or Ie, R3 is —C(O)R8. In some such embodiments, R8 is an optionally substituted C1-6alkyl. In some such embodiments. R8 is a C1-6alkyl optionally substituted with one or more R18. In some such embodiments, R18 is selected from the group consisting of halo, cyano, hydroxy, C1-6alkoxy, C6-10aryl, C6-10aryloxy, sulfhydryl, haloC1-6alkoxy, C1-6alkylthio, C6-10arylthio, and nitro. In some particular embodiments, R8 is —CH(CH3)2.

In some embodiments of the compounds of Formula I, Ia, Ib, Ic, Id, or Ie, R3 is an optionally substituted C2-10alkoxyalkyl. In some such embodiments, R3 is a C2-10alkoxyalkyl optionally substituted with one or more R19. In some such embodiments, R19 is selected from the group consisting of halo, cyano, hydroxy, C1-6alkoxy, C6-10aryl, C6-10aryloxy, sulfhydryl, haloC1-6alkoxy, C1-6alkylthio, C6-10arylthio, and nitro. In some particular embodiments, R3 is —CH2OCH2CH3.

In some embodiments of the compounds of Formula I, Ia, Ib, Ic, Id, Ie, or If, R7 is an optionally substituted C1-8alkyl. In some such embodiments, R7 is a C1-8alkyl optionally substituted with one or more R20. In some such embodiments, R20 is selected from the group consisting of halo, cyano, hydroxy, C1-6alkoxy, C6-10aryl, C6-10aryloxy, sulfhydryl, haloC1-6alkoxy, C1-6alkylthio, C6-10arylthio, and nitro. In some particular embodiments, R7 is methyl. In some other particular embodiments, R7 is —CH2CH2CH2OH.

In some embodiments of the compounds of Formula I, Ia, Ib, Ic, Id, Ie, or If, R7 is oxo.

In some embodiments of the compounds of Formula I, Ia, Ib, Ic, Id, Ic, or If, R7 is an optionally substituted C6-18aryl. In some such embodiments, R7 is a C6-18aryl optionally substituted with one or more R21. In some such embodiments, R21 is selected from the group consisting of C1-6alkyl, halo, cyano, hydroxy, C1-6alkoxy, haloC1-6alkyl, haloC1-6alkoxy, nitro, —C(=O)NR22R23, —N(R24)C(=O)R25, —C(=O)OR26, —OC(=O)R27, and —C(=O)R28. In some such embodiments, each of R22, R23, R24, R25, R26, R27, and R28 is independently selected from the group consisting of hydrogen, C1-6alkyl, C2-6alkenyl, C2-6alkynyl C3-7carbocyclyl, C6-10aryl, 5-10 membered heteroaryl, and 3-10 membered heterocyclyl. In some further embodiments, R7 is a phenyl. In some particular embodiments, R7 is

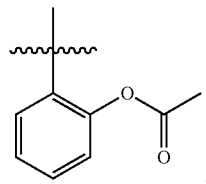

In some embodiments of the compounds of Formula I, Ia, Ib, Ic, Id, Ie, or If, R7 is an optionally substituted 5-18 membered heteroaryl. In some such embodiments, R7 is a 5-18 membered heteroaryl optionally substituted with one or more R29. In some such embodiments, R29 is selected from the group consisting of C1-6alkyl, halo, cyano, hydroxy, C1-6alkoxy, haloC1-6alkyl, haloC1-6alkoxy, nitro, —C(=O)NR30R31, —N(R32)C(=O)R33, —C(=O)OR34, —OC(=O)R35, and —C(=O)R36. In some such embodiments, each of R30, R31, R32, R33, R34, R35, and R36 is independently selected from the group consisting of hydrogen, C1-6alkyl, C2-6alkenyl, C2-6alkynyl, C3-7carbocyclyl, C6-10aryl, 5-10 membered heteroaryl, and 3-10 membered heterocyclyl. In some further embodiments, R7 is a 6 membered heteroaryl. In some particular embodiments, R7 is

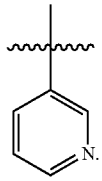

In some embodiments of the compounds of Formula I, Ia, Ib, Ic, Id, Ie, If, or Ig, R4 is a fragment of a liver-targeting therapeutic agent or a fragment of a liver-activated therapeutic agent. In some such embodiments, R4 is a fragment of a lipid-lowering therapeutic agent or a fragment of a cholesterol-biosynthesis-inhibiting therapeutic agent. In some such embodiments, R4 is a fragment of a HMG-CoA reductase inhibitor. In some such embodiments, R4 is a fragment of a statin. In some further embodiments, R4 is selected from the group consisting of

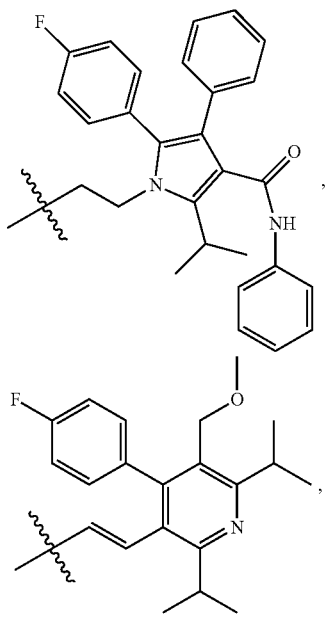

-continued

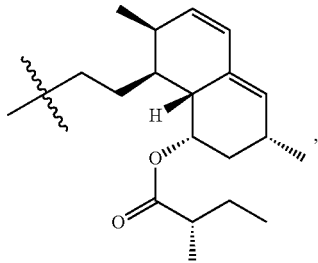

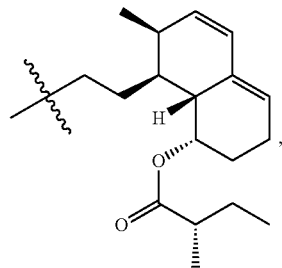

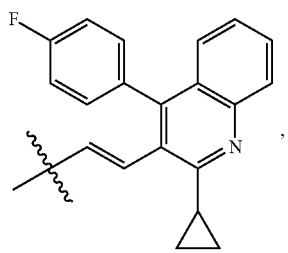

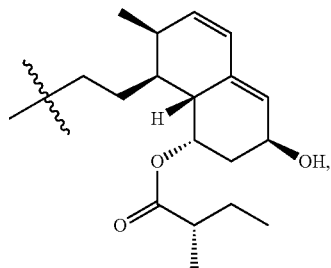

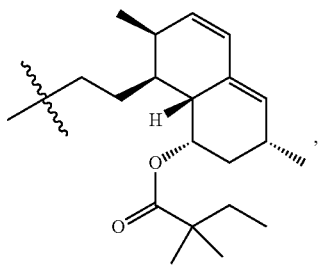

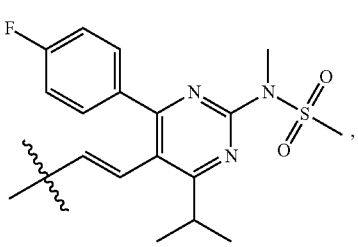

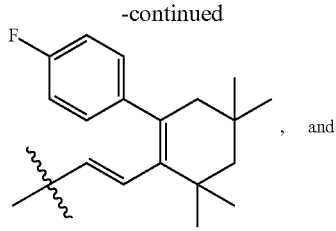

, and

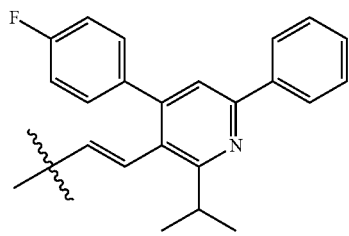

In some particular embodiments, R4 is

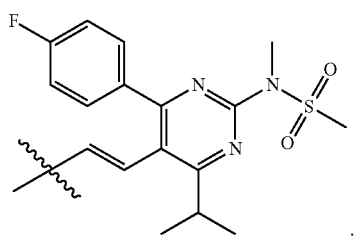 [SMILES: */C=C/c1c(-c2ccc(F)cc2)nc(N(C)S(C)(=O)=O)nc1C(C)C]

In some embodiments of the compounds of Formula II, Z is O.

In some embodiments, R37 is H.

R39 in some embodiments is ethyl.

R38 in some embodiments is the optionally substituted fragment of a therapeutic agent. In some such embodiments, the fragment of a therapeutic agent is

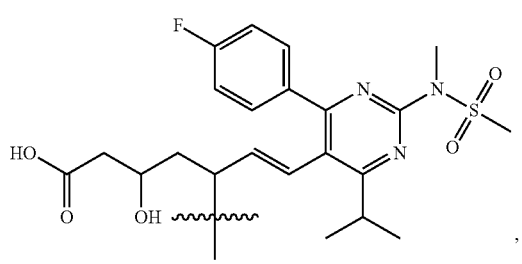 [SMILES: *C(/C=C/c1c(-c2ccc(F)cc2)nc(N(C)S(C)(=O)=O)nc1C(C)C)CC(O)CC(=O)O]

optionally substituted with one or more moieties C1-6alkyl, halo, and C6-18aryl. In some such embodiments, the substituent is methyl, such that R38 has the structure

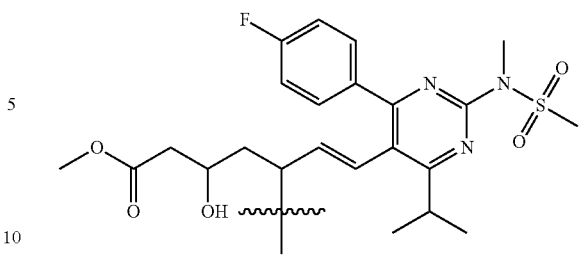

In some embodiments, the fragment of the therapeutic agent is

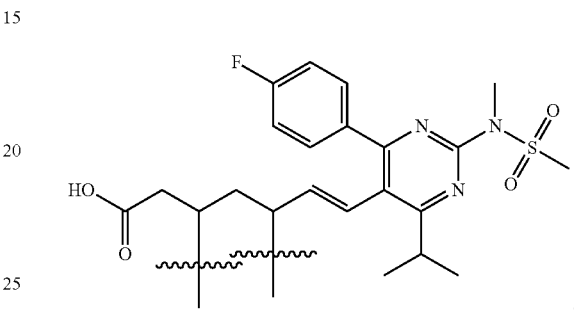

optionally substituted with

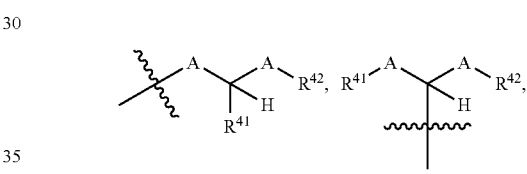

C1-6alkyl, halo, and C6-1 aryl. In some such embodiments, the substituent is

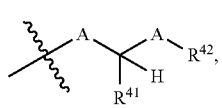

such that R38 has the structure

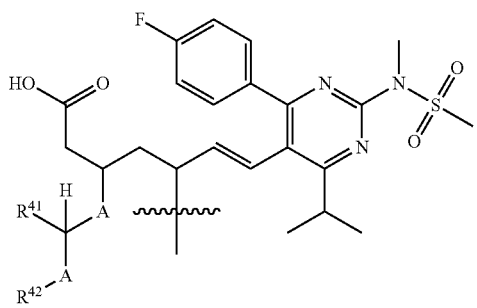

In some embodiments, A is O.
In some embodiments, R41 is H.
In some embodiments, R42 is ethyl.
In some embodiments, the compounds of Formula I, Ia, Ib, Ic, Id, Ie, If, or II as described herein are selected from the group consisting of

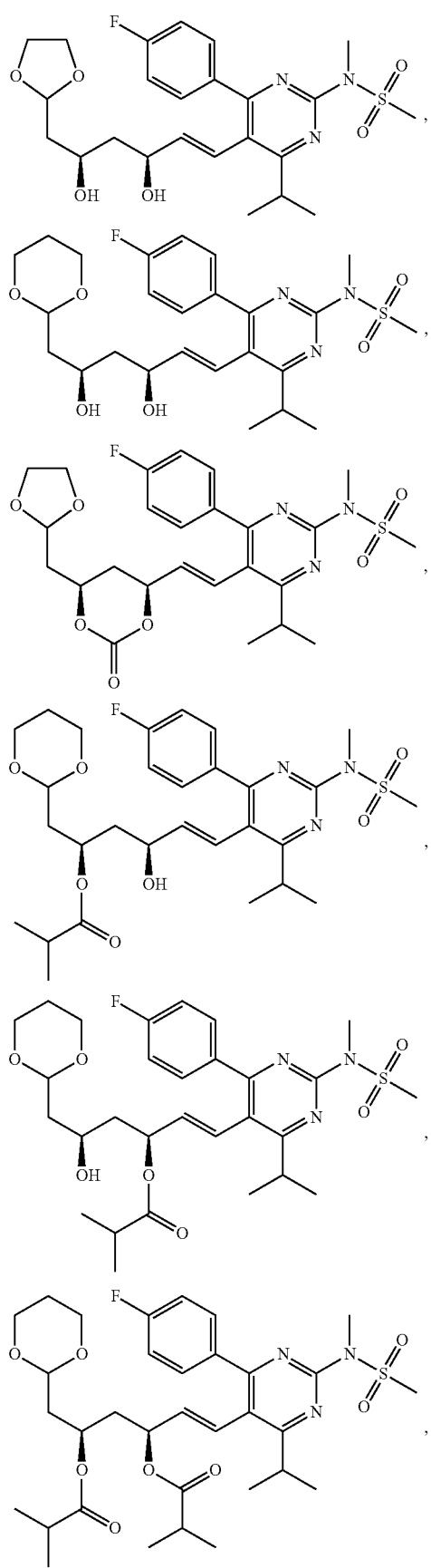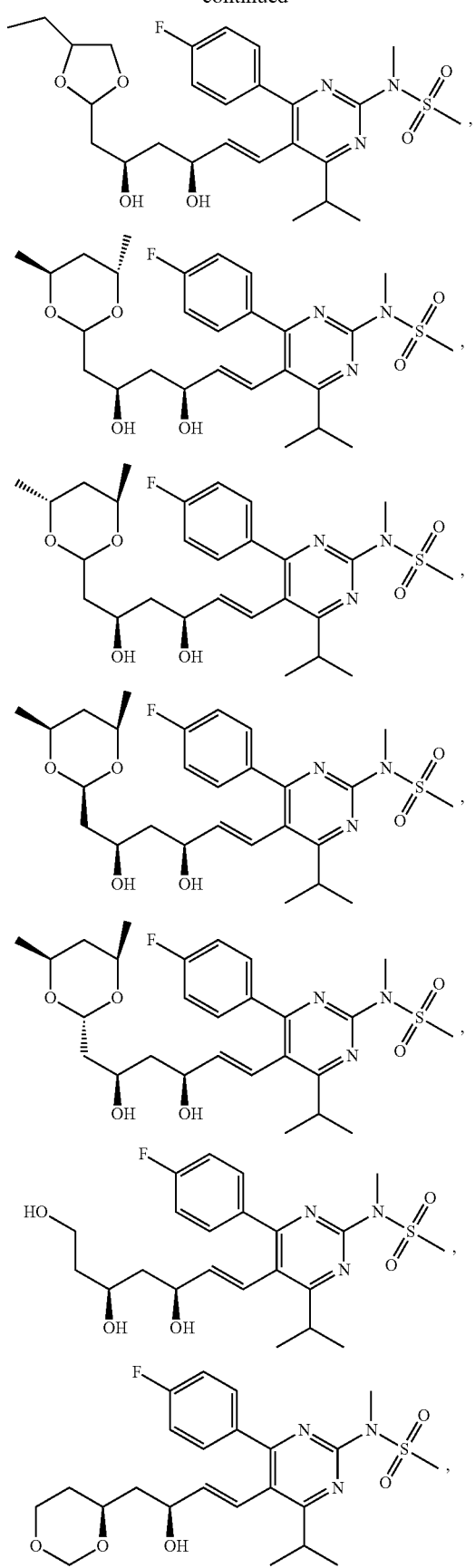

13
-continued
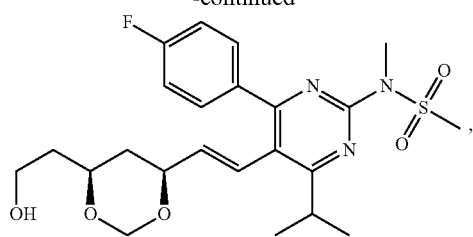
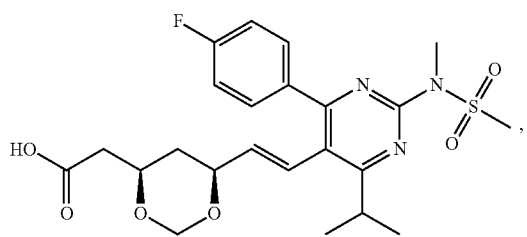
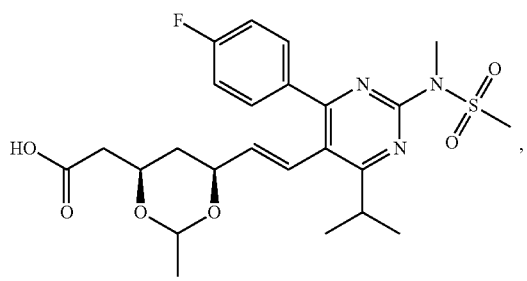
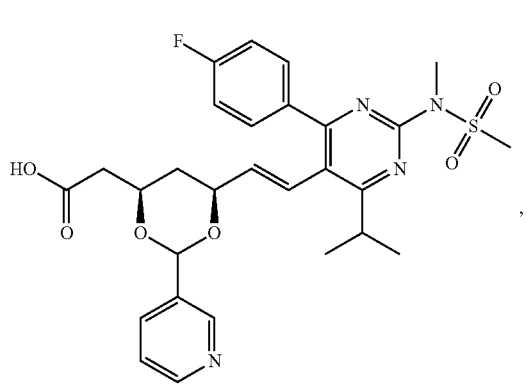
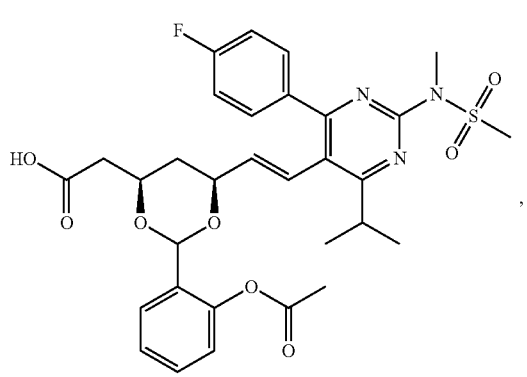
14
-continued
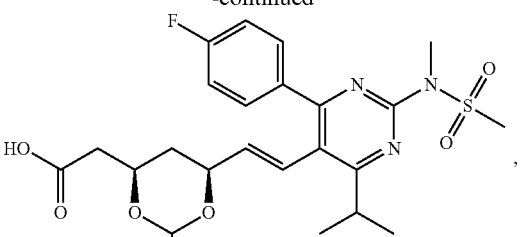
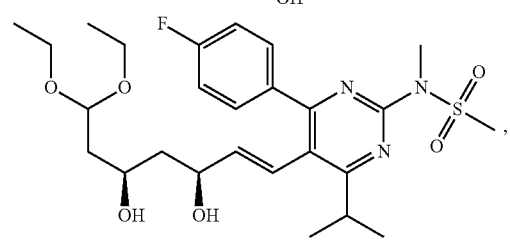
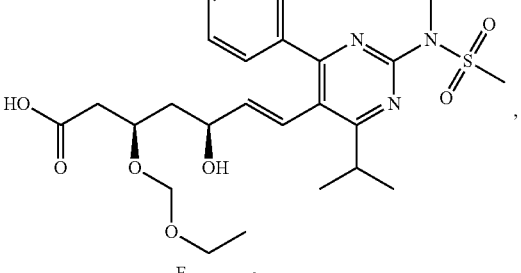
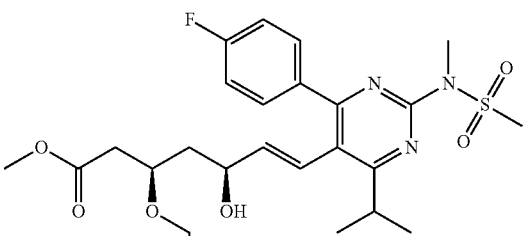
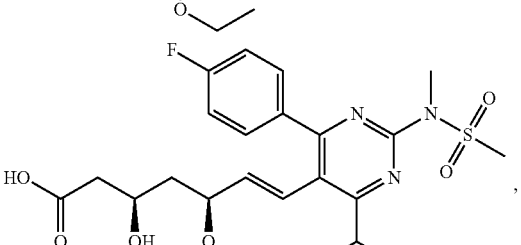
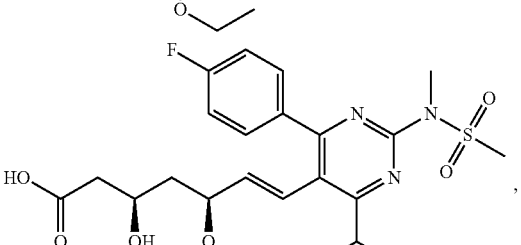

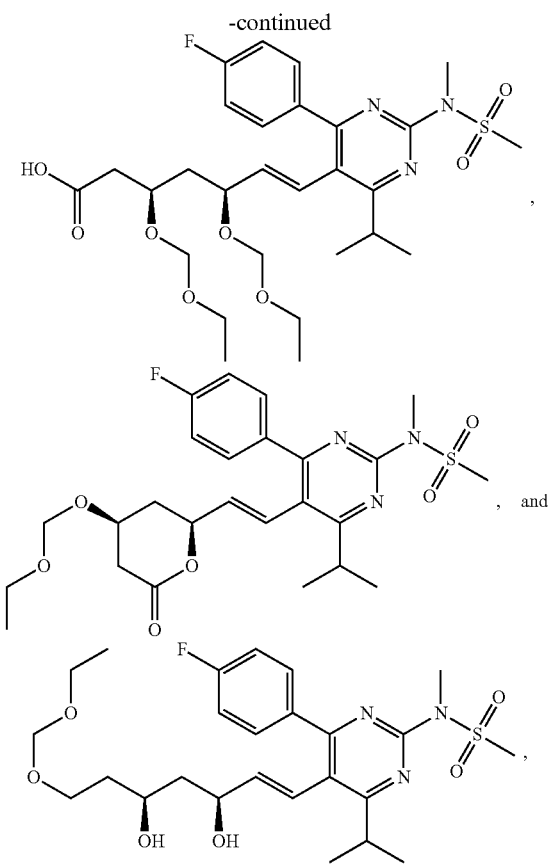

or pharmaceutically acceptable salts thereof.

In some embodiments, the pharmaceutically acceptable salts are selected from alkaline metal salts or ammonium salts. In some embodiments, the pharmaceutically acceptable salts are sodium salts, including disodium salts.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein, including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Definitions

Unless defined otherwise, all technical and scientific terms used herein have the same meaning as is commonly understood by one of ordinary skill in the art. All patents, applications, published applications, and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an," and "the" include plural referents unless the context clearly dictates otherwise. Unless otherwise indicated, conventional methods of mass spectroscopy, NMR, HPLC, protein chemistry, biochemistry, recombinant DNA techniques, and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
Ac Acetyl
aq. Aqueous
Bn Benzyl
Bz Benzoyl
BOC or Boc Cert-Butoxycarbony
° C. Temperature in degrees Centigrade
DCM Dichloromethane
DMF N,N-dimethylformamide
EA Ethyl acetate
Et Ethyl
g Gram(s)
h or hr Hour(s)
HATU 2-(7-aza-1H-benzotriazole-1-yl)-1,1,3,3-tetramethyluronium hexafluorophosphate
HPLC High-Performance Liquid Chromatography
iPr Isopropyl
m or min Minute(s)
MECN Acetonitrile
mL Milliliter(s)
NMR Nuclear magnetic resonance
PE Petroleum ether
PG Protecting group Ph Phenyl
rt Room temperature
TBDMSCl tert-Butyldimethylsilyl chloride
TBS tert-Butyldimethylsilyl
TEA Triethylamine
Tert, t tertiary
TFA Trifluoroacetic acid
THF Tetrahydrofuran
TIPDS Tetraisopropyldisiloxanylidene
TPDSCl Tetraisopropyldisiloxanylidene Chloride
TLC Thin-layer chromatography
TosOH p-Toluenesulfonic Acid
μL Microliter(s)

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and test-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-burimercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buuten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms, The heteroalkyl group may be designated as "$C_{1-}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. In various embodiments, a heteroalkyl may contain from 1 to 10 heteroatoms, for example, 1 to 5 heteroatoms, 1 to 3 heteroatoms, 2 heteroatoms, or 1 heteroatom.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. In some embodiments, of the ring members, from 1 to 5 are heteroatoms, for example, the heteroaryl may contain from 1 to 4 heteroatoms, from 1 to 3 heteroatoms, two heteroatoms, or one heteroatom. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropyimethyl, cyclobutylmethyl, cyclopropylethyl, cyclopropylbutyl, cyclobutylethyl, cyclopropylisopropyl, cyclopeptylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In some embodiments, of the ring members, from 1 to 5 are heteroatoms, for example, the heterocyclyl may contain from 1 to 4 heteroatoms, from 1 to 3 heteroatoms, two heteroatoms, or one heteroatom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is selected from hydrogen, optionally substituted $C_{1-6}$ alkyl, halogen, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, optionally substituted $C_{1-6}$ alkyl, halogen, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

A "C-carboxy" group refers to a "—C(=O)OR" group in which R is selected from hydrogen, halogen, optionally substituted $C_{1-6}$ alkyl, optionally substituted $C_{2-6}$ alkenyl, optionally substituted $C_{2-6}$ alkynyl, optionally substituted. $C_{3-7}$ carbocyclyl, optionally substituted $C_{6-10}$ aryl, optionally substituted 5-10 membered heteroaryl, and optionally substituted 3-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

A "sulfonyl" group refers to an "—SO$_2$R" group in which R is selected from hydrogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "S-sulfonamido" group refers to a "—SO$_2$NR$_A$R$_B$" group in which R$_A$ and R$_B$ are each independently selected from hydrogen, halogen, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "N-sulfonamido" group refers to a "—N(R$_A$)SO$_2$R$_B$" group in which R$_A$ and R$_B$ are each independently selected from hydrogen, halogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted. $C_{6-10}$ aryl, optionally substituted 5-10 membered heteroaryl, and optionally substituted 3-10 membered heterocyclyl, as defined herein.

A "C-amido" group refers to a "—C(=O)NR$_A$R$_B$" group in which R$_A$ and R$_B$ are each independently selected from hydrogen, halogen, optionally substituted. $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "N-amido" group refers to a "—N(R$_A$)C(=O)R$_B$" group in which R$_A$ and R$_B$ are each independently selected from hydrogen, halogen, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-5}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, a $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in Which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, halogen, optionally substituted $C_{1-6}$ alkyl, optionally substituted $C_{2-6}$ alkenyl, optionally substituted $C_{2-6}$ alkynyl, optionally substituted $C_{3-7}$ carbocyclyl, optionally substituted $C_{6-10}$ aryl, optionally substituted 5-10 membered heteroaryl, and optionally substituted 3-10 membered heterocyclyl as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1C_6$ alkoxy, $C_1$-$C_6$ alkoxy($C_1$-$C_6$)alkyl (i.e., ether), aryloxy, sulfhydryl (mercapto), hato($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

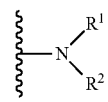

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

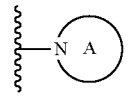

where ring A is a heterocyclyl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

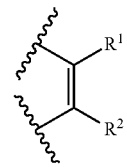

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

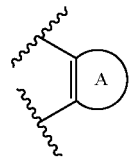

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

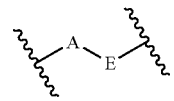

includes the substituent being oriented such that the A is attached at the leftmost attachment point of the molecule as well as the case in which A is attached at the rightmost attachment point of the molecule.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense, Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

A therapeutic effect relieves, to some extent, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

Methods of Preparation

The compounds disclosed herein may be synthesized by methods described below, or by modification of these methods. Ways of modifying the methodology include, among others, temperature, solvent, reagents, etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley. New York (1999), which are both hereby incorporated herein by reference in their entirety. The protecting groups may be removed at a convenient subsequent stage using methods known from the art. Synthetic chemistry transformations useful in synthesizing applicable compounds are known in the art and include, e.g., those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme I is provided for the guidance of the reader, and represents an example of a general strategy for making the compounds described herein. Other methods for preparing the compounds described herein will be readily apparent to the person of ordinary skill in the art in light of the following reaction schemes and examples.

Compounds of structure 4 can be prepared from precursors of structure 1 by protection of the diol, reduction of the carboxyl to the corresponding aldehyde (structure 3), acetalation, and then deprotection. Compounds of structure 5 can be obtained by acylation or further acetalation of the compounds of structure 4.

Compounds of structure 6 can be prepared from precursors of structure 1 by esterification followed by acetalation. Compounds of structure 7 can be prepared by direct acetalation of precursors of structure 1. Compounds of structure 8 can be obtained from precursors of structure 1 by lactonization followed by acetalation.

Compounds of structure 9 can be obtained by direct reduction of precursors of structure 1. Compounds of structures 10 and 11 can be prepared from compounds of structure 9 by treatment with formaldehyde.

Scheme I

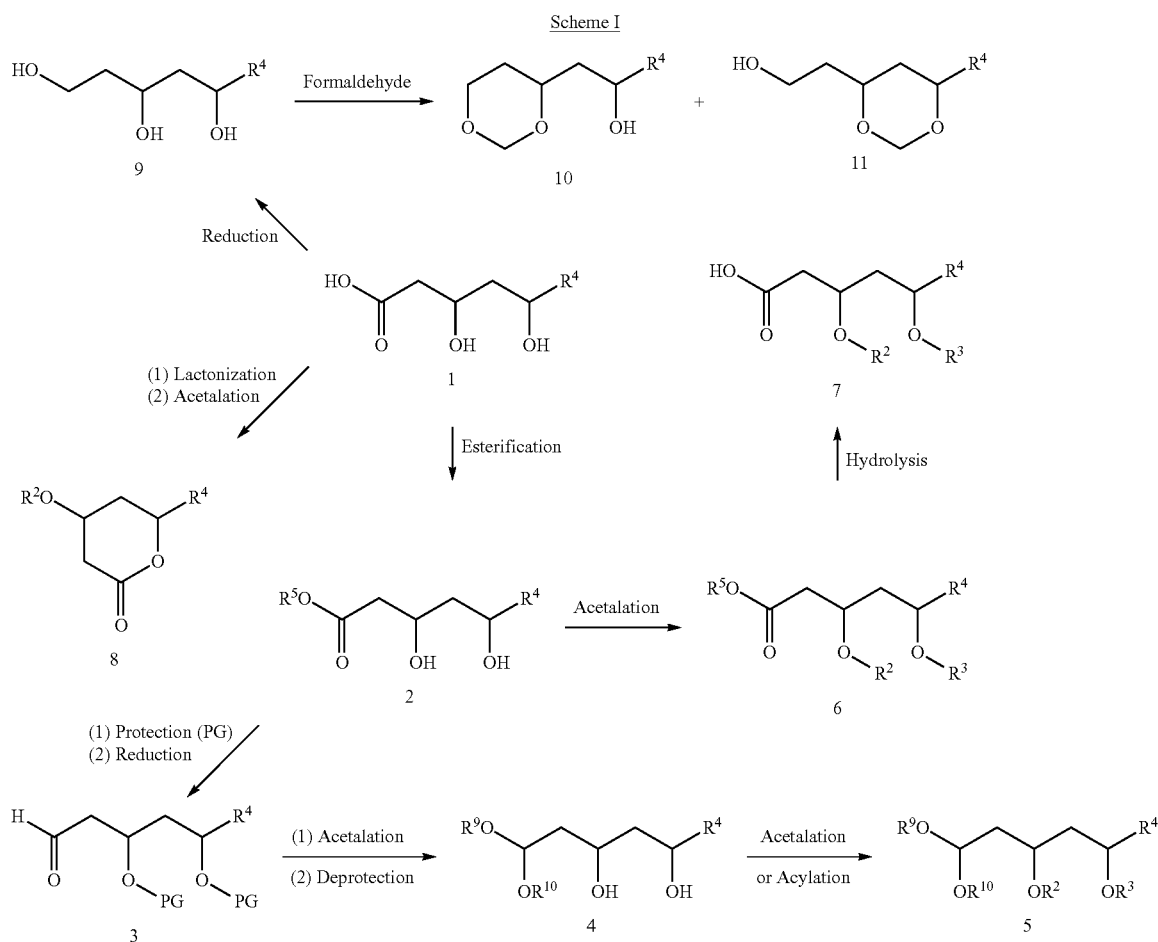

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds described above can be formulated into pharmaceutical compositions for use in treatment of these conditions. Standard pharmaceutical formulation techniques are used, such as those disclosed in Remington's The Science and. Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the compounds described above, some embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions described above may be in any of a variety of suitable forms for a variety of routes for administration, for example, for oral, nasal, rectal, topical (including transdertnal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9, Accordingly, buffers include acetate buffers, citrate buffers, phosphate buffers and borate buffers. Acids or bases may be used to adjust the pH of these formulations as needed.

In a similar vein, an ophthaltnically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharma Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating a liver disease, disorder, or condition by administering the compounds or pharmaceutical compositions described herein to a subject in need thereof. In some such embodiments, the liver disease, disorder, or condition involves the metabolism, storage, or homeostatic control of biochemical end products such as cholesterol, fatty acids, bile, triglycerides, plasma proteins, carrier proteins, lipoproteins, acute phase proteins, apolipoproteins, carbohydrates, hemostatic factors, fibrinolysis factors, thrombopoietin, insulin-like growth factor 1, hepcidin, angiotensinogen, vitamin A, vitamin D, vitamin B12, vitamin K, iron, copper, or catalase. In some particular embodiments, the liver disease, disorder, or condition being treated is liver fibrosis, cirrhosis, hepatitis, alcoholic liver disease, fatty liver, liver cancer, hemochromatosis, Wilson's disease, primary sclerosing cholangitis, alpha 1-antitrypsin deficiency, hyperglycemia, hypoglycemia, or diabetes.

Some embodiments of the present invention include methods of treating a cardiovascular disease, disorder, or condition, by administering the compounds or pharmaceutical compositions described herein to a subject in need thereof. In some particular embodiments, the cardiovascular disease, disorder, or condition is dyslipidemia or atherosclerosis. In other particular embodiments, the cardiovascular disease, disorder, or condition is hyperlipidemia.

Some embodiments of the present invention include methods of altering blood lipid concentration by administering the compounds or pharmaceutical compositions described herein to a subject in need thereof.

Some embodiments of the present invention include methods of inhibiting HMG-CoA reductase by administering the compounds or pharmaceutical compositions described herein to a subject in need thereof.

Some embodiments of the present invention include methods of reducing the side effects of liver-targeting or liver-activated drugs by administering the compounds or pharmaceutical compositions described herein, rather than their corresponding active drug compound, to a subject in need thereof. In some such embodiments, the corresponding active drug compound is a statin. Examples side effects that can be reduced include headache, difficulty sleeping, flushing of the skin, muscle aches, muscle tenderness, muscle weakness, drowsiness, dizziness, nausea, vomiting, abdominal pain, bloating, gas, diarrhea, constipation, or rash.

Some embodiments of the present invention include methods of increasing the therapeutic index of liver-targeting or liver-activated therapeutic agents.

In some embodiments, the subject is a mammal.

In some embodiments, the subject is a human.

Further embodiments include administering a combination of compounds to a subject in need thereof. A combination can include a compound or pharmaceutical composition described herein with an additional medicament.

Some embodiments include co-administering a compound or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment, the agents are administered through the same route, such as orally. In another embodiment, the agents are administered through different routes, such as one being administered orally and another being administered intravenously.

In some embodiments, the additional medicament is a cholesterol absorption inhibitor, a hypertension medicament, niacin, or aspirin. In some such embodiments, the cholesterol absorption inhibitor is ezetimibe. In some such embodiments, the hypertension medicament is a diuretic, a beta-blocker, an angiotensin-converting enzyme inhibitor, an angiotensin receptor blocker, a calcium channel blocker, an alpha blocker, an alpha-2 receptor agonist, a combined alpha and beta-blocker, a central agonist, a peripheral adrenergic inhibitor, or a vasodilator. Examples of hypertension medicaments that can be used as the additional medicament include acebutolol, alpha methyldopa, amiloride hydrochloride, amlodipine besylate, atenolol, benazepril hydrochloride, betaxolol, bepridil, bisoprolol fumarate, bumetanide, candesartan, captopril, carteolol hydrochloride, carvedilol, chlorthalidone, chlorothiazide, clonidine hydrochloride, diltiazem hydrochloride, doxazosin mesylate, enalapril maleate, eprosartan mesylate, felodipine, fosinopril sodium, furosemide, hydralazine hydrochloride, hydrochlorothiazide, guanabenz acetate, guanadrel, guanethidine nionosulfate, guanfacine hydrochloride, indapamide, irbesarten, isradipine, labetalol hydrochloride, lisinopril, losartan potassium, methyldopa, metolazone, metoprolol succinate, metoprolol tartrate, minoxidil, moexipril, nadolol, nicardipine, nifedipine, nisoldipine, penbutolol sulfate, perindopril, pindolol, prazosin hydrochloride, propranolol hydrochloride, quinapril hydrochloride, ramipril, reserpine, telmisartan, terazosin hydrochloride, trandolapril, triamterene, solotol hydrochloride, spironolactone, timolol maleate, valsartan, and verapamil hydrochloride.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

Some compounds of Formula I, Ia, Ib, Ic, Id, Ie, If, Ig, and II can be prepared as described below.

Example 1

N-(5-((3S,5R,E)-6-(1,3-Dioxolan-2-yl)-3,5-dihydroxy-hex-1-en-1-yl)-4-(4-fluorophenyl)-6-isopropylpyrimidin-2-yl)-N-methylmethanesulfonamide (Compound 101)

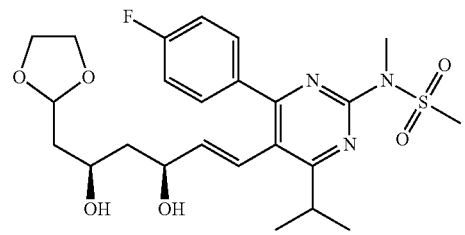 [SMILES: CC(C)c1nc(N(C)S(C)(=O)=O)nc(-c2ccc(F)cc2)c1/C=C/[C@@H](O)C[C@@H](O)CC1OCCO1]

To a solution of rosuvastatin (10.0 g, 20.8 mmol) in DMF (75.0 mL) was added 3-bromoprop-1-ene (4.20 g, 34.7 mmol, 1.67 eq). The solution was stirred at 25° C. and monitored by TLC. After 16 hours, the reaction mixture was concentrated under reduced pressure, diluted with $H_2O$, and extracted with DCM. After drying over $Na_2SO_4$, the combined organic layers were concentrated under reduced pressure. The concentrate was purified by column chromatography (PE/EA=1:1) to give rosuvastatin allyl ester (6.41 g, 12.3 mmol, 59% yield) as a light-yellow oil.

Imidazole (5.56 g, 81.7 mmol, 6.00 eq) was added to a solution of the allyl ester (6.91 g, 13.6 mmol) in DMF (50 mL), and then a solution of TIPDSCl (6.33 g, 27.22 mmol, 2.00 eq) in DMF (25 mL) was added dropwise. The resulting mixture was stirred at 25° C. for 16 hours and monitored by TLC. Afterward, the reaction mixture was concentrated under reduced pressure, diluted with $H_2O$, and extracted with DCM. The combined organic layers were dried over $Na_2SO_4$ and concentrated to give the crude mixture. Purification by column chromatography (PE/EA=5:1) afforded TIPDS-protected rosuvastatin allyl ester (10.0 g, 13.1 mmol, 96% yield) as a light-yellow oil.

To a solution of the TIPDS-protected rosuvastatin allyl ester (12.9 g, 16.8 mmol) in EtOH (200 mL) was added $NaBH_4$ (1.27 g, 33.7 mmol, 2.00 eq). The resulting mixture was stirred at 40° C. and monitored by TLC. After 16 hours, the reaction mixture was filtered, washed with EtOH, and concentrated under reduced pressure. Purification by column chromatography (PE: EA=5:1) yielded the primary alcohol (6.56 g, 9.24 mmol 55% yield) as a light-yellow oil.

To a solution of the primary alcohol (6.38 g, 8.99 mmol) in DCM (120 mL) was added Dess-Martin periodinane (4.58 g, 10.79 mmol, 1.20 eq). The reaction mixture was stirred at 25° C. for 16 hours while monitoring by TLC. The reaction mixture was filtered, concentrated under reduced pressure, diluted with DCM, and then washed with water. After drying over Na$_2$SO$_4$, the combined organic layers were concentrated under reduced pressure. The concentrate was purified by column chromatography (PE/EA=10:1) to afford the aldehyde (4.17 g, 5.89 mmol, 65% yield).

Ethylene glycol (87.7 mg, 1.41 mmol, 2.00 eq), TosOH (60.8 mg, 0.353 mmol, 0.50 eq) and MgSO$_4$ (10 g, 83 mmol) were added to a solution of the aldehyde (500 mg, 0.706 mmol) in DCM (50 mL). The resulting mixture was stirred at 60° C. for 48 hours and until HPLC (ET12043-33-P1B) indicated that 30% of the aldehyde was consumed. The reaction mixture was filtered and the filtrate washed with DCM. Afterward, the combined organics were concentrated, diluted with DCM, and washed with water. The combined organic layers were dried over Na$_2$SO$_4$ and concentrated under reduced pressure. Purification by column chromatography (PE/EA=25:1) gave the acetal (177 mg, 0.235 mmol, 33% yield) as a light-yellow oil.

To a solution of the acetal (602 mg, 0.80 mmol) in THF (50.0 mL) was added TEA-3HF (774 mg, 4.80 mmol, 6.00 eq). The resulting mixture was stirred at 30° C. for 16 hours and until TLC indicated that most of the acetal was consumed. The reaction mixture was concentrated and purified by column chromatography (PE/EA=25/1 to 3/1) to afford Compound 101 (328 mg, 0.64 mmol, 80% yield) as light-yellow oil. $^1$H NMR (400 MHz, CDCl$_3$): δ 7.65-7.62 (m, 2H), 7.09-7.05 (m, 2H), 6.63-6.58 (dd, J=16.0 and 1.65, 1H), 5.47-5.41 (dd, J=16.0 and 5.07, 1H), 5.00-4.98 (t, 1H), 4.45-4.42 (m, 1H), 4.17-4.12 (m 1H), 4.02-3.98 (m, 2H), 3.92-3.82 (m, 3H), 3.55 (s, 3H),3.50 (s, 3H), 3.40-3.31 (m, 1H), 1.89-1.81 (m, 2H), 1.59-1.50 (m, 3H), 1.44-1.40 (m, 1H), 1.24-1.25(d, J=6.62, 6H). [M+H]$^+$ calculated for C$_{24}$H$_{32}$FN$_3$O$_6$S: 510.21; found: 510.2.

Example 2

N-(5-((3S,5R,E)-6-(1,3-Dioxan-2-yl)-3,5-dihydroxyhex-1-en-1-yl)-4-(4-fluorophenyl)-6-isopropylpyrimidin-2-yl)-N-methylmethanesulfonamide (Compound 102)

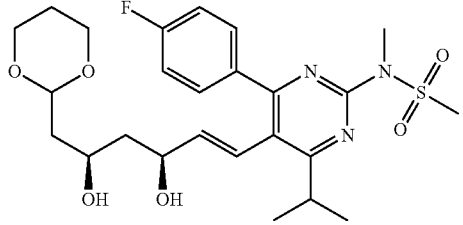 [SMILES: CC(C)c1nc(N(C)S(C)(=O)=O)nc(-c2ccc(F)cc2)c1/C=C/[C@@H](O)C[C@@H](O)CC1OCCCO1]

Compound 102 was prepared according to Scheme I from rosuvastatin and 1,3-dihydroxypropane in a manner similar to that of Compound 101. [M+H]$^+$ calculated for C$_{25}$H$_{34}$FN$_3$O$_6$S: 524.23; found: 524.3.

Example 3

N-(5-((E)-2-((4S,6R)-6-((1,3-Dioxolan-2-yl)methyl)-2-oxo-1,3-dioxan-4-yl)vinyl)-4-(4-fluorophenyl)-6-isopropylpyrimidin-2-yl)-N-methylmethanesulfonamide (Compound 103)

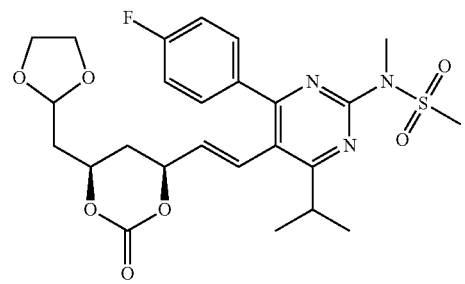 [SMILES: CC(C)c1nc(N(C)S(C)(=O)=O)nc(-c2ccc(F)cc2)c1/C=C/[C@@H]1C[C@H](CC2OCCO2)OC(=O)O1]

Compound 103 was prepared from treatment of Compound 101 with carbonyldiimidazole. [M+H]$^+$ calculated for C$_{25}$H$_{30}$FN$_3$O$_7$S: 536.19; found: 536.1.

Example 4

(2R,4S,E)-1-(1,3-Dioxan-2-yl)-6-(4-(4-fluorophenyl)-6-isopropyl-2-(N-methylmethylsulfonamido)pyrimidin-5-yl)-4-hydroxyhex-5-en-2-yl isobutyrate (Compound 104 and (3S,5R,E)-6-(1,3-dioxan-2-yl)-1-(4-(4-fluorophenyl)-6-isopropyl-2-(N-methylmethylsulfonamido)pyrimidin-5-yl)-5-hydroxyhex-1-en-3-yl isobutyrate (Compound 105)

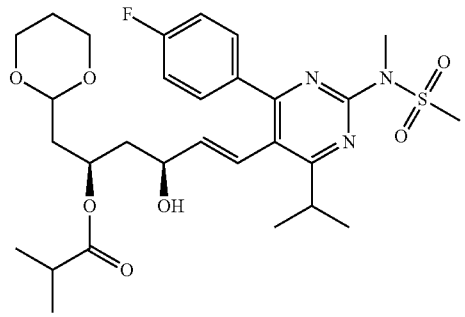

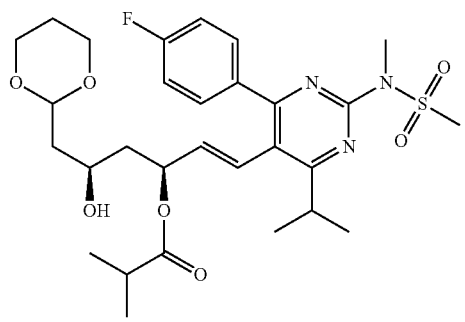

Compounds 104 and 105 were prepared as a mixture from treatment of Compound 102 with isobutyryl chloride in the presence of pyridine. [M+H]$^+$ calculated for C$_{29}$H$_{40}$FN$_3$O$_7$S: 594.27; found: 594.3.

Example 5

(2R,4S,E)-1-(1,3-Dioxan-2-yl-6-(4-(4-fluorophenyl)-6-isopropyl-2-(N-methylmethylsulfonamido)pyrimidin-5-yl)hex-5-ene-2,4-diyl bis(2-methylpropanoate) (Compound 106)

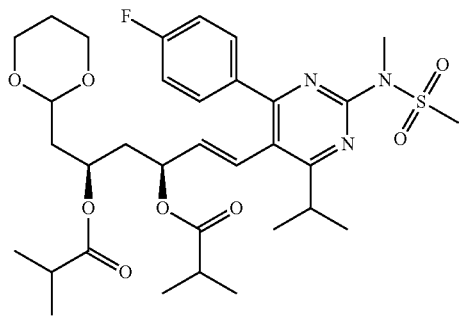 [SMILES: CC(C)C(=O)O[C@@H](CC1OCCCO1)C[C@@H](/C=C/c1c(-c2ccc(F)cc2)nc(N(C)S(C)(=O)=O)nc1C(C)C)OC(=O)C(C)C]

Compounds 106 were prepared from treatment of Compound 102 with isobutyryl chloride in the presence of pyridine. [M+H]$^+$ calculated for $C_{33}H_{46}FN_3O_8S$: 664.31; found: 664.3.

Example 6

N-(5-((3S,5R,E)-6-(4-Ethyl-1,3-dioxolan-2-yl)-3,5-dihydroxyhex-1-en-1-yl)-4-(4-fluorophenyl)-6-isopropylpyrimidin-2-yl1-N-methylmethanesulfonamide (Compound 107)

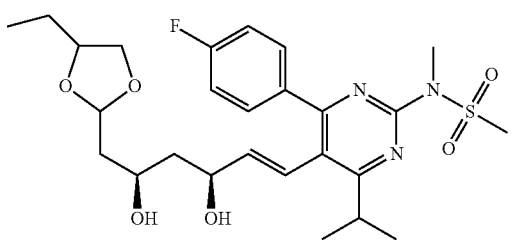 [SMILES: CCC1COC(C[C@H](O)C[C@H](O)/C=C/c2c(-c3ccc(F)cc3)nc(N(C)S(C)(=O)=O)nc2C(C)C)O1]

Compound 107 was prepared according to Scheme I from rosuvastatin and (±)-1,2-dihydroxybutane in a manner similar to that of Compound 101. [M+H]$^+$ calculated for $C_{26}H_{36}FN_3O_6S$: 538.24; found: 538.2.

Example 7

N-(5-((3S,5R,E)-6-((4S,6S)-4,6-Dimethyl-1,3-dioxan-2-yl-3,5-dihydroxyhex-1-en-1-yl)-4-(4-fluorophenyl)-6-isopropylpyrimidin-2-yl)-N-methylmethanesulfonamide (Compound 108) and N-(5-((3S,5R,E)-6-((4R,6R)-4,6-dimethyl-1,3-dioxan-2-yl-3,5-dihydroxyhex-1-en-1-yl)-4-(4-fluorophenyl)-6-isopropylpyrimidin-2-yl)-N-methylmethanesulfonamide (Compound 109)

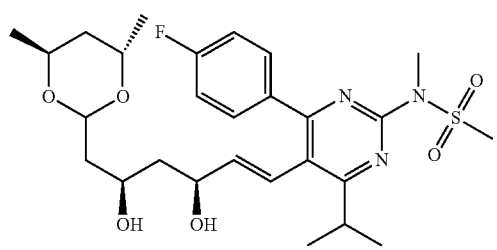

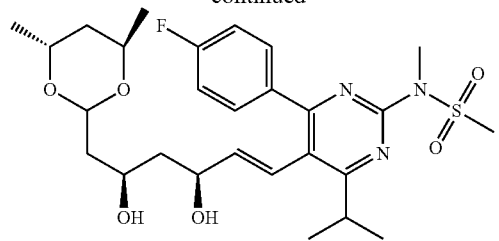

Compounds 108 and 109 were prepared as a mixture according to Scheme I from rosuvastatin and (±)-2,4-dihydroxypentane in a manner similar to that of Compound 101. [M+H]$^+$ calculated for $C_{27}H_{38}FN_3O_6S$: 552.26; found: 552.2.

Example 8

N-(5-((3S,5R,E)-6-((2S,4S,6R)-4,6-Dimethyl-1,3-dioxan-2-yl)-3,5-dihydroxyhex-1-en-1-yl)-4(4-fluorophenyl)-6-isopropylpyrimidin-2-yl)-N-methylmethanesulfonamide (Compound 110) and N-(5-((3S,5R,E)-6-((2R,4R,6R)-4,6-dimethyl-1,3-dioxan-2-yl)-3,5-dihydroxyhex-1-en-1-yl)-4-(4-fluorophenyl)-6-isopropylpyrimidin-2-yl)-N-methylmethanesulfonamide (Compound 111)

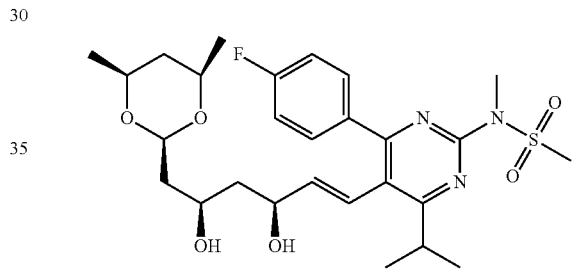

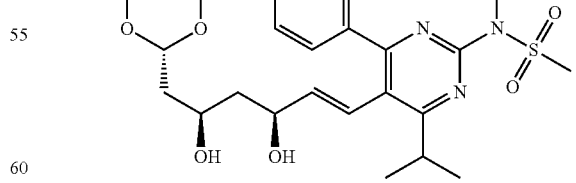

Compounds 110 and 111 were isolated as a mixture from the reaction in Example 7 operated according to Scheme I from rosuvastatin and (±)-2,4-dihydroxypentane in a manner similar to that of Compound 101. [M+H]$^+$ calculated for $C_{27}H_{38}FN_3O_6S$: 552.26; found: 552.2.

Example 9

N-(4-(4-Fluorophenyl)-6-isopropyl-5-(3S,5S,E)-3,5,7-trihydroxyhept-1-en-1-yl)pyrimidin-2-yl3-N-methylmethanesulfonamide (Compound 112)

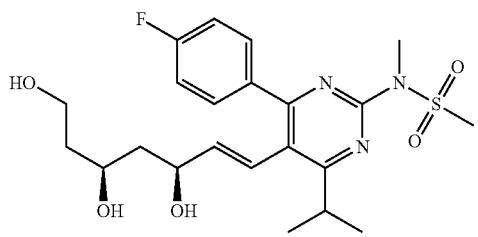 [SMILES: CC(C)c1nc(N(C)S(C)(=O)=O)nc(-c2ccc(F)cc2)c1/C=C/[C@@H](O)C[C@@H](O)CCO]

Compounds 112 was prepared by directly reduction of rosuvastatin with sodium borohydride. [M+H]$^+$ calculated for $C_{22}H_{30}FN_3O_5S$: 468.20; found: 468.2.

Example 10

N-(5-((S,E)-4-((S)-1,3-Dioxan-4-yl)-3-hydroxybut-1-en-1-yl)-4-(4-fluorophenyl)-6-isopropylpyrimidin-2-yl)-N-methylmethanesulfonamide (Compound 113)

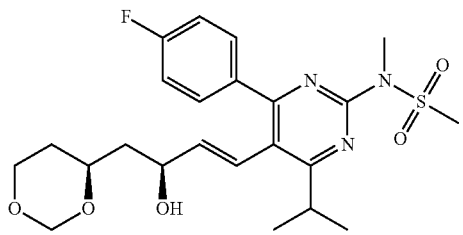 [SMILES: CC(C)c1nc(N(C)S(C)(=O)=O)nc(-c2ccc(F)cc2)c1/C=C/[C@@H](O)C[C@@H]1CCOCO1]

Compounds 113 was prepared according to a standard acetyl procedure from Compound 112 and formaldehyde. [M+H]$^+$ calculated for $C_{23}H_{30}FN_3O_5S$: 480.20; found: 480.2.

Example 11

N-(4-(4-Fluorophenyl)-5-((E)-2-((4S,6S)-6-(2-hydroxyethyl)-1,3-dioxan-4-yl)vinyl)-6-isopropylpyrimidin-2-yl)-N-methylmethanesulfonamide (Compound 114)

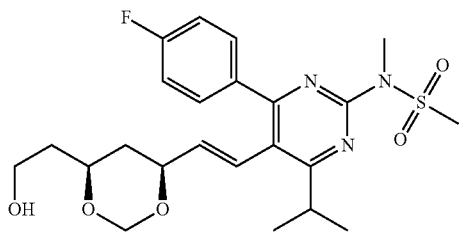 [SMILES: CC(C)c1nc(N(C)S(C)(=O)=O)nc(-c2ccc(F)cc2)c1/C=C/[C@@H]1C[C@H](CCO)OCO1]

Compounds 114 was isolated from the reaction in Example 10 to prepare Compound 113 according to a standard acetyl procedure from Compound 112 and formaldehyde. [M+H]$^+$ calculated for $C_{23}H_{30}FN_3O_5S$: 480.20; found: 480.2.

Example 12

2-((4R,6S)-6-((E)-2-(4-(4-Fluorophenyl)-6-isopropyl-2-(N-methylmethylsulfonamido)pyrimidin-5-yl)vinyl)-1,3-dioxan-4-yl)acetic acid (Compound 115)

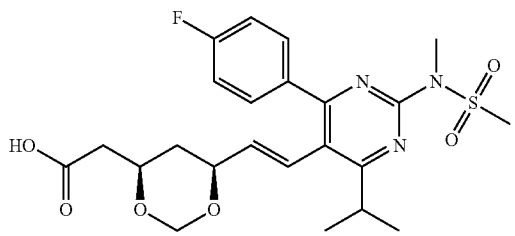 [SMILES: CC(C)c1nc(N(C)S(C)(=O)=O)nc(-c2ccc(F)cc2)c1/C=C/[C@@H]1C[C@H](CC(=O)O)OCO1]

Compounds 115 was prepared according to Scheme I from rosuvastatin and formaldehyde. [M+H]$^+$ calculated for $C_{23}H_{28}FN_3O_6S$: 494.18; found: 494.3.

Example 13

2-((4R,6S)-6-((E)-2-(4-(4-Fluorophenyl)-6-isopropyl-2-(N-methylmethylsulfonamido)pyrimidin-5-yl)vinyl)-2-methyl-1,3-dioxan-4-yl)acetic acid (Compound 116)

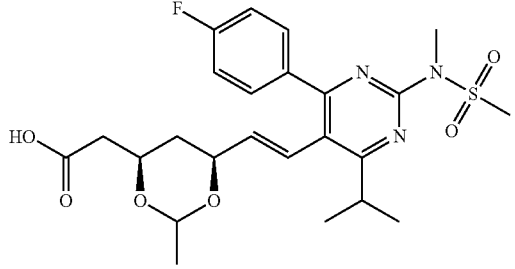

Compounds 116 was prepared according to Scheme I from rosuvastatin and acetaldehyde. [M+H]$^+$ calculated for $C_{24}H_{30}FN_3O_6S$: 508.19; found: 508.1.

Example 14

2-((4R6S)-6-((E)-2-(4-(4-Fluorophen71)-6-isopropyl-2-(N-methylmethylsulfonamido)pyrimidin-5-yl)vinyl)-2-(pyridin-3-yl)-1,3-dioxan-4-yl)acetic acid (Compound 117)

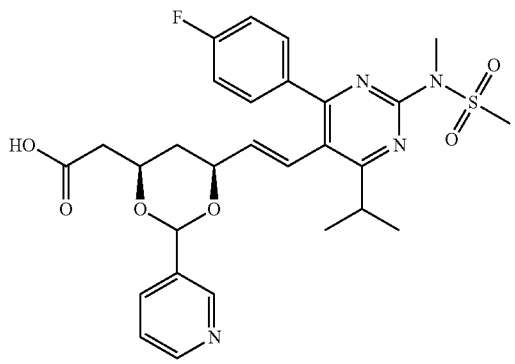

Compounds 117 was prepared according to Scheme I from rosuvastatin and nicotinaldehyde. [M+H]$^+$ calculated for $C_{28}H_{31}FN_4O_6S$: 571.20; found: 571.1.

Example 15

2-((4R,6S)-2-(2-Acetoxyphenyl)-6-((E)-2-(4-(4-fluorophenyl)-6-isopropyl-2-(N-methylmethylsulfonamido)pyrimidin-5-yl)vinyl)-1,3-dioxan-4-yl)acetic acid (Compound 118)

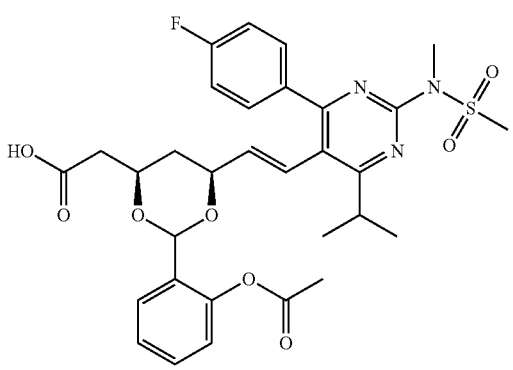

Compounds 118 was prepared according to Scheme I from rosuvastatin and nicotinaldehyde. [M+H]$^+$ calculated for $C_{31}H_{34}FN_3O_8S$: 628.22; found: 628.1.

Example 16

2-((4R,6S)-6-((E)-2-(4-(4-Fluorophenyl)-6-isopropyl-2-(N-methylmethylsulfonamido)pyrimidin-5-yl)vinyl-2-(3-hydroxypropyl)-1,3-dioxan-4-yl)acetic acid (Compound 119)

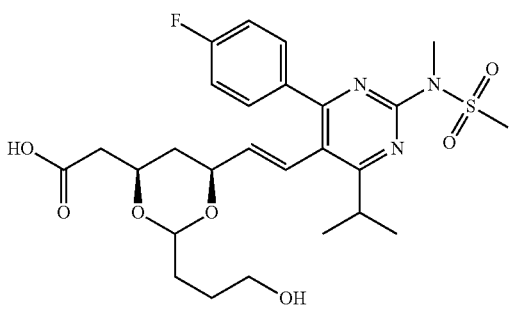

Compounds 119 was prepared according to Scheme I from rosuvastatin and 4-hydroxybutanal. [M+H]$^+$ calculated for $C_{26}H_{34}FN_3O_7S$: 552.22; found: 552.5.

Example 17

N-(5-((3S,5R,E)-7,7-Diethoxy-3,5-dihydroxyhept-1-en-1-yl)-4-(4-fluorophenyl-6-isopropylpyrimidin-2-yl)-N-methylmethanesulfonamide (Compound 120)

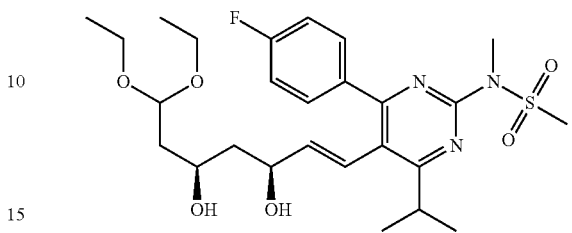

Compounds 120 was prepared according to Scheme I from rosuyastatin and ethanol in a manner similar to that of Compound 101. [M+H]$^+$ calculated for $C_{26}H_{38}FN_3O_6S$: 540.26; found: 540.2.

Example 18

(3R,5S,E)-3-(Ethoxymethoxy)-7-(4-(4-fluoropheny-6-isopropyl-2-(N-methylmethylsulfonamido)pyrimidin-5-yl)-5-hydroxyhep-6-enoic acid (Compound 121)

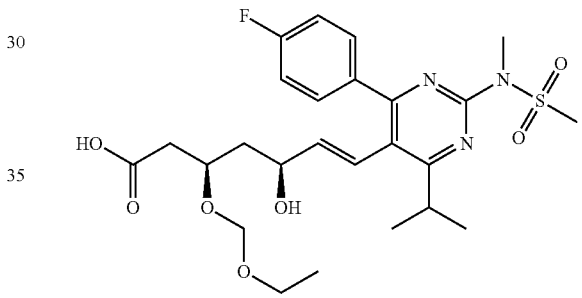

Compounds 121 was prepared according to a standard procedure from rosuvastatin and chloromethyl ethyl ether. [M+H]$^+$ calculated for $C_{25}H_{34}FN_3O_7S$: 540.22; found: 540.2.

Example 19

Methyl (3R,5S,E)-3-(ethoxymethoxy)-7-(4-(4-fluorophen₃4)-6-isopropyl-2-(N-methylmethylsulfonamido)pyrimidin-5-yl)-5-hydroxyhept-6-enoate (Compound 122)

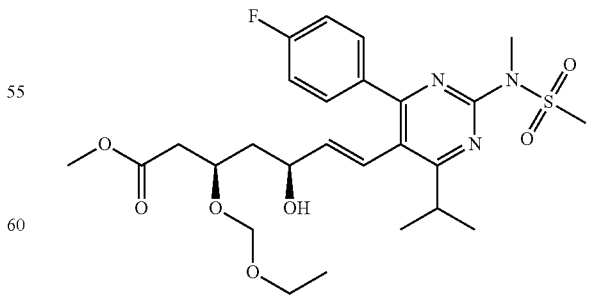

Compounds 122 was prepared according to a standard procedure from rosuvastatin and chloromethyl ethyl ether. [M+H]$^+$ calculated for $C_{26}H_{36}FN_3O_7S$: 554.24; found: 554.2.

Example 20

(3R,5S,E)-5-(Ethoxymethoxy)-7-(4-(4-fluorophenyl)-6-isopropyl-2-(N-methylmethylsulfonamido)pyrimidin-5-yl)-3-hydroxyhept-6-enoic acid (Compound 123)

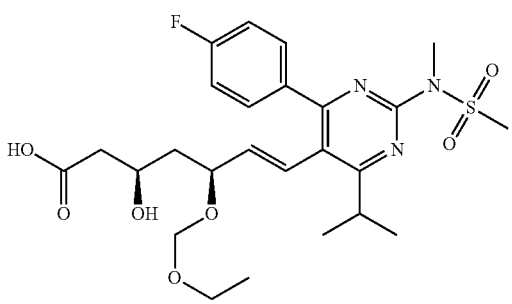 [SMILES: CCOCO[C@H](/C=C/c1c(-c2ccc(F)cc2)nc(N(C)S(C)(=O)=O)nc1C(C)C)C[C@@H](O)CC(=O)O]

Compounds 123 was prepared according to a standard procedure from rosuvastatin and chloromethyl ethyl ether. [M+H]$^+$ calculated for $C_{25}H_{34}FN_3O_7S$: 540.22; found: 540.2.

Example 21

Methyl (3R,5S,E)-5-(ethoxymethoxy)-7-(4-(4-fluorophenyl)-6-isopropyl-2-(N-methylmethylsulfonamido)pyrimidin-5-yl)-3-hydroxyhept-6-enoate (Compound 124)

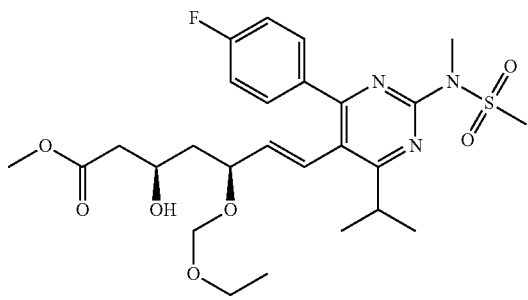

Compounds 124 was prepared according to a standard procedure from rosuvastatin and chloromethyl ethyl ether. [M+H]$^+$ calculated for $C_{26}H_{36}FN_3O_7S$: 554.24; found: 554.2.

Example 22

(3R,5S,E)-3,5-bis(Ethoxymethoxy)-7-(4-(4-fluorophen71)-6-isopropyl-2-(N-methylmethylsulfonamido)pyrimidin-5-yl)hept-6-enoic acid (Compound 125)

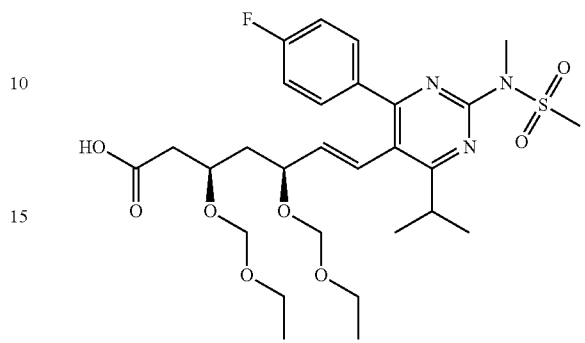

Compounds 125 can be prepared according to a standard procedure from rosuvastatin and chloromethyl ethyl ether. [M+H]$^+$ calculated for $C_{28}H_{40}FN_3O_8S$: 598.26.

Example 23

N-(5-((E)-2-((2S,4S)-4-(Ethoxymethoxy)-6-oxotetrahydro-2H-pyran-2-yl)vinyl)-4-(4-fluorophenyl)-6-isopropylpyrimidin-2-yl)-N-methylmethanesulfonamide (Compound 126)

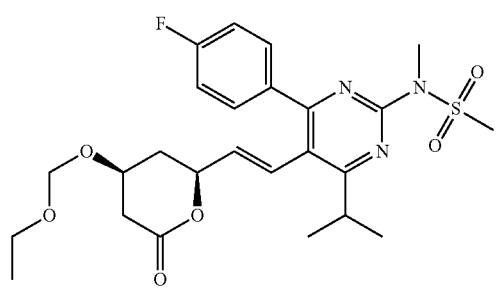 [SMILES: CCOCO[C@@H]1CC(=O)O[C@H](/C=C/c2c(-c3ccc(F)cc3)nc(N(C)S(C)(=O)=O)nc2C(C)C)C1]

Compounds 126 was prepared according to a standard procedure from rosuvastatin and chloromethyl ethyl ether. [M+H]$^+$ calculated for $C_{25}H_{32}FN_3O_6S$: 522.21; found: 522.2.

Example 24

N-(5-((3S,5S,E)-7-(Ethoxymethoxy)-3,5-dihydroxyhept-1-en-1-yl)-4-(4-fluorophenyl)-6-isopropylpyrimidin-2-yl)-N-methylmethanesulfonamide (Compound 127)

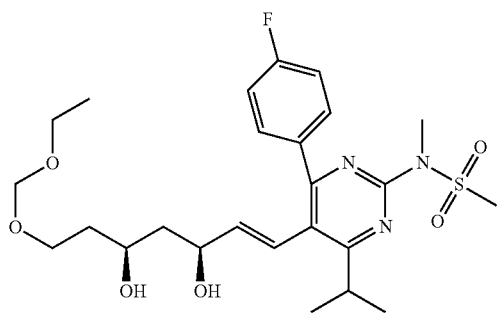 [SMILES: CCOCOCC[C@H](O)C[C@H](O)/C=C/c1c(-c2ccc(F)cc2)nc(N(C)S(C)(=O)=O)nc1C(C)C]

Compounds 127 can be prepared according to a standard procedure from rosuvastatin and chloromethyl ethyl ether. [M+H]$^+$ calculated for $C_{25}H_{36}FN_3O_6S$: 526.24.

Example 25

Tissue Distribution Following Oral Administration

The liver specificity of the disclosed compounds were determined and compared with their corresponding active drug compounds. The disclosed compounds and reference active drug compounds were administered at 5-20 mg/kg to fasted rats by oral gavage. Plasma concentrations of the active, metabolite, and the prodrug compounds in circulation and in the hepatic portal vein were determined by a standard HPLC-LV method. Concentrations of the same in the liver, small intestine, and other organs were measured by the standard LC-MS method.

Table 1 summarizes the results, which demonstrates improved liver distribution of the disclosed compounds relative to their active drug counterparts.

TABLE 1

| | Total Rosuvastatin Levels 1 and 5 Hours after 5 mg/kg Administration in Rats | | |
|---|---|---|---|
| Compound | Total rosuvastatin levels* in the liver (ng/g) | Total rosuvastatin levels* in blood (ng/mL) | Liver/Blood Ratio |
| Rosuvastatin | 1,046 | 43 | 24 |
| 101 | >1,000 | <50 | >24 |
| 104/105 | >3,000 | <100 | >24 |
| 108/109 | >10,000 | <500 | >24 |
| 110/111 | >14,000 | <500 | >24 |
| 120 | >10,000 | <500 | >24 |
| 121 | >3,000 | <100 | >24 |
| 123 | >10,000 | <500 | >24 |

*Total rosuvastatin level = rosuvastatin level at 1 hour + rosuvastatin level at 5 hours

What is claimed is:
1. A compound having the structure of Formula I:

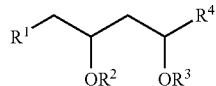

I or a pharmaceutically acceptable salt thereof, wherein:
$R^1$ is selected from the group consisting of optionally substituted $C_{1-8}$alkyl, —COOR$^5$, optionally substituted $C_{2-10}$alkoxyalkyl, and 3-12 membered heterocyclyl optionally substituted with one or more $R^{15}$, or alternatively:
 (i) $R^1$ and $R^2$ together with the atoms to which they are attached form an optionally substituted 4-10 membered heterocyclyl, or
 (ii) $R^1$ and $R^3$ together with the atoms to which they are attached form an optionally substituted 6-10 membered heterocyclyl;
$R^2$ is selected from the group consisting of H, —C(O)R$^6$, and optionally substituted $C_{2-10}$alkoxyalkyl, or alternatively:
 (i) $R^1$ and $R^2$ together with the atoms to which they are attached form an optionally substituted 4-10 membered heterocyclyl, or
 (ii) $R^2$ and $R^3$ together with the atoms to which they are attached form a 6-10 membered heterocyclyl, optionally substituted with one or more $R^7$;
$R^3$ is selected from the group consisting of H, —C(O)R$^8$, and optionally substituted $C_{2-10}$alkoxyalkyl, or alternatively:
 (i) $R^1$ and $R^3$ together with the atoms to which they are attached form an optionally substituted 6-10 membered heterocyclyl, or
 (ii) $R^2$ and $R^3$ together with the atoms to which they are attached form a 6-10 membered heterocyclyl, optionally substituted with one or more $R^7$;
$R^4$ is

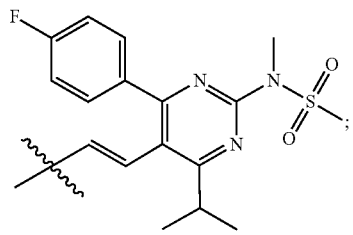

$R^5$ is selected from the group consisting of halogen, optionally substituted $C_{2-6}$alkynyl, optionally substituted $C_{6-10}$aryl, and optionally substituted 5-10 membered heteroaryl;
$R^6$ is selected from the group consisting of H, halogen, optionally substituted $C_{2-6}$alkenyl, optionally substituted $C_{2-6}$alkynyl, optionally substituted $C_{3-7}$carbocyclyl, and optionally substituted 3-10 membered heterocyclyl;
$R^8$ is selected from the group consisting of H, optionally substituted $C_{1-6}$alkyl, halogen, optionally substituted $C_{2-6}$alkenyl, optionally substituted $C_{2-6}$alkynyl, optionally substituted $C_{3-7}$carbocyclyl, optionally substituted $C_{6-10}$aryl, optionally substituted 5-10 membered heteroaryl, and optionally substituted 3-10 membered heterocyclyl; and
each $R^7$ is independently selected from the group consisting of optionally substituted $C_{1-8}$alkyl, oxo, optionally substituted $C_{6-18}$aryl, and optionally substituted 5-18 membered heteroaryl;
each $R^{15}$ is selected from the group consisting of $C_{1-6}$alkyl, $C_{1-6}$alkenyl, $C_{1-6}$alkynyl, $C_{1-6}$heteroalkyl, $C_{3-7}$carbocyclyl, 3-10 membered heterocyclyl, $C_{6-18}$aryl, $C_{6-18}$aryl $C_{1-6}$alkoxy, 5-10 membered heteroaryl, 5-10 membered heteroaryl $C_{1-6}$alkyl, halo, cyano, hydroxyl, $C_{1-6}$alkoxy, $C_{2-10}$alkoxyalkyl, aryloxy, sulfhydryl, halo$C_{1-6}$alkyl, halo$C_{1-6}$alkoxy, $C_{1-6}$alkylthio, $C_{6-18}$arylthio, and nitro;
wherein when an alkyl group is substituted, it is substituted with one or more substituents selected from the group consisting of: $C_1$-$C_6$alkyl; $C_1$-$C_6$alkenyl; $C_1$-$C_6$alkynyl; $C_1$-$C_6$heteroalkyl; $C_3$-$C_7$carbocyclyl optionally substituted with halo, $C_1$-$C_6$alkyl, $C_1$-$C_6$alkoxy, $C_1$-$C_6$haloalkyl, and $C_1$-$C_6$haloalkoxy; $C_3$-$C_7$carbocyclyl-$C_1$-$C_6$-alkyl optionally substituted with halo, $C_1$-$C_6$alkyl, $C_1$-$C_6$alkoxy, $C_1$-$C_6$haloalkyl, and $C_1$-$C_6$haloalkoxy; 3-10 membered heterocyclyl optionally substituted with halo, $C_1$-$C_6$alkyl, $C_1$-$C_6$alkoxy, $C_1$-$C_6$haloalkyl, and $C_1$-$C_6$haloalkoxy; 3-10 membered heterocyclyl-$C_1$-$C_6$-alkyl optionally substituted with halo, $C_1$-$C_6$alkyl, $C_1$-$C_6$alkoxy, $C_1$-$C_6$haloalkyl, and $C_1$-$C_6$haloalkoxy; aryl optionally substituted with halo, $C_1$-$C_6$alkyl, $C_1$-$C_6$alkoxy, $C_1$-$C_6$haloalkyl, and $C_1$-$C_6$haloalkoxy; aryl($C_1$-$C_6$)alkyl optionally substituted with halo, $C_1$-$C_6$alkyl, $C_1$-$C_6$alkoxy, $C_1$-$C_6$haloalkyl, and $C_1$-$C_6$haloalkoxy; 5-10 membered heteroaryl optionally substituted with halo, $C_1$-$C_6$alkyl, $C_1$-$C_6$alkoxy, $C_1$-$C_6$haloalkyl, and $C_1$-$C_6$haloalkoxy; 5-10 membered heteroaryl($C_1$-$C_6$) alkyl optionally substituted with halo, $C_1$-$C_6$alkyl, $C_1$-$C_6$alkoxy, $C_1$-$C_6$haloalkyl, and $C_1$-$C_6$haloalkoxy; halo; cyano; hydroxyl; $C_1$-$C_6$alkoxy; $C_1$-$C_6$alkoxy($C_1$-$C_6$)alkyl; aryloxy; sulfhydryl; halo($C_1$-$C_6$)alkyl; halo($C_1$-$C_6$)alkoxy; $C_1$-$C_6$alkylthio; arylthio; amino; amino($C_1$-$C_6$)alkyl; nitro; O-carbamyl ; N-carbamyl; O-thiocarbamyl; N-thiocarbamyl; C-amido; N-amido; S-sulfonamido; N-sulfonamido; C-carboxy; O-carboxy; acyl; cyanate; isocyanato; thiocyanato; isothiocyanato; sulfinyl; and sulfonyl;

wherein at least one of $R^2$ and $R^3$ is not H; and wherein if $R^1$ and $R^3$ together with the atoms to which they are attached form a 6 membered heterocyclyl, then $R^2$ is not H.

2. The compound of claim 1 having the defined 1,3-cis-stereochemistry shown in Formula Ia, Ib, Ic, Id, Ie, If, or Ig:

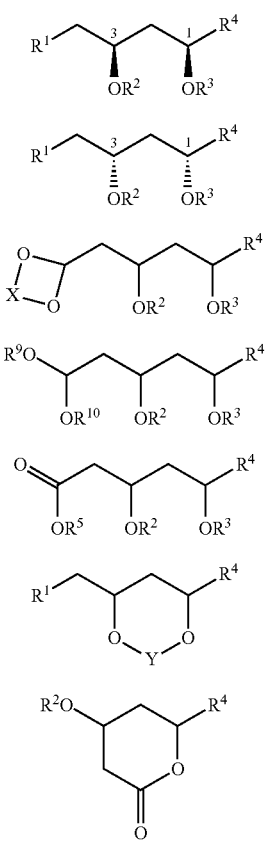

or a pharmaceutically acceptable salt thereof,
wherein X is an optionally substituted $C_{1-7}$alkylene linker;
wherein Y is a $C_{1-5}$alkylene linker, optionally substituted with one or more $R^7$; and
wherein each of $R^9$ and $R^{10}$ is independently an optionally substituted $C_{1-6}$alkyl.

3. The compound of claim 1, wherein $R^1$ is a $C_{1-8}$alkyl optionally substituted with one or more $R^{13}$, and wherein $R^{13}$ is selected from the group consisting of halo, cyano, hydroxyl, $C_{1-6}$alkoxy, $C_{6-10}$aryloxy, sulfhydryl, halo $C_{1-6}$alkoxy, $C_{1-6}$alkylthio, $C_{1-6}$arylthio, and nitro.

4. The compound of claim 1, wherein $R^1$ is —CH2OH.

5. The compound of claim 1, wherein $R^1$ is —COOR$^5$.

6. The compound of claim 1, wherein $R^1$ is a $C_{2-10}$alkoxyalkyl optionally substituted with one or more $R^{14}$, and wherein $R^{14}$ selected from the group consisting of halo, cyano, hydroxyl, $C_{1-6}$alkoxy, $C_{6-10}$aryloxy, sulfhydryl, halo $C_{1-6}$alkoxy, $C_{1-6}$alkylthio, $C_{6-10}$arylthio, and nitro.

7. The compound of claim 1, wherein $R^1$ is —CH$_2$OCH$_2$OCH$_2$CH$_3$ or —CH(OCH$_2$CH$_3$)$_2$.

8. The compound of claim 1, wherein $R^1$ is a 3-12 membered heterocyclyl substituted with one or more $R^{15}$, wherein $R^{15}$ is selected from the group consisting of $C_{1-6}$alkyl, $C_{3-7}$carbocyclyl, $C_{1-6}$alkoxy, $C_{6-18}$aryl, and halo.

9. The compound of claim 1, wherein $R^1$ is

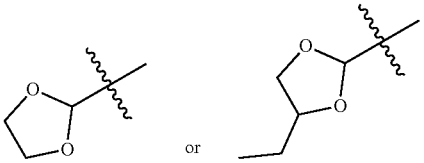

10. The compound of claim 1 , wherein $R^1$ is

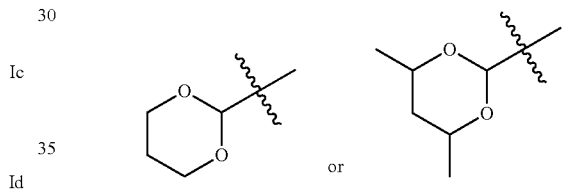

11. The compound of claim 1, wherein $R^2$ is H.

12. The compound of claim 1, wherein $R^2$ is —C(O)R$^6$.

13. The compound of claim 1, wherein $R^2$ is a $C_{2-10}$alkoxyalkyl optionally substituted with one or more $R^1$, and wherein $R^{17}$ selected from the group consisting of halo, cyano, hydroxyl, $C_{1-6}$alkoxy, $C_{6-10}$aryl, $C_{6-10}$aryloxy, sulfhydryl, halo$C_{1-6}$alkoxy, $C_{1-6}$alkylthio, $C_{6-10}$arylthio, and nitro.

14. The compound of claim 1, wherein $R^2$ is —CH$_2$OCH$_2$CH$_3$.

15. The compound of claim 1, wherein $R^3$ is H or —C(O)R$^8$.

16. The compound of claim 1, wherein $R^8$ is a $C_{1-6}$alkyl optionally substituted with one or more $R^{18}$, and wherein $R^{18}$ is selected from the group consisting of halo, cyano, hydroxyl, $C_{1-6}$alkoxy, $C_{6-10}$aryl, $C_{6-10}$aryloxy, sulfhydryl, halo$C_{1-6}$alkoxy, $C_{1-6}$alkylthio, $C_{6-10}$arylthio, and nitro.

17. The compound of claim 1, wherein $R^8$ is —CH(CH$_3$)$_2$.

18. The compound of claim 1, wherein $R^3$ is a $C_{2-10}$alkoxyalkyl optionally substituted with one or more $R^{19}$, and wherein $R^{19}$ is selected from the group consisting of halo, cyano, hydroxyl, $C_{1-6}$alkoxy, $C_{6-10}$aryl, $C_{6-10}$aryloxy, sulfhydryl, halo$C_{1-6}$alkoxy, $C_{1-6}$alkylthio, $C_{6-10}$arylthio, and nitro.

19. The compound of claim 1, wherein $R^3$ is —CH$_2$OCH$_2$CH$_3$.

20. The compound of claim 1, wherein $R^7$ is a $C_{1-8}$alkyl optionally substituted with one or more $R^{20}$, and wherein $R^{20}$ is selected from the group consisting of halo, cyano, hydroxyl, $C_{1-6}$alkoxy, $C_{6-10}$aryl, $C_{6-10}$aryloxy, sulfhydryl, halo$C_{1-6}$alkoxy, $C_{1-6}$alkylthio, $C_{6-10}$arylthio, and nitro.

21. The compound of claim 1, wherein $R^7$ is methyl, —CH$_2$CH$_2$CH$_2$OH, or oxo.

22. The compound of claim 1, wherein $R^7$ is a $C_{6-18}$aryl optionally substituted with one or more $R^{21}$, wherein $R^{21}$ is selected from the group consisting of $C_{1-6}$alkyl, halo, cyano, hydroxyl, $C_{1-6}$alkoxy, halo $C_{1-6}$alkyl, halo $C_{1-6}$alkoxy, nitro, —C(=O)NR$^{22}$R$^{23}$, —N(R$^{24}$)C(=O)R$^{25}$, —C(=O)OR$^{26}$, —OC(=O)R$^{27}$, and —C(=O)R$^{28}$, and wherein each of $R^{22}$, $R^{23}$, $R^{24}$, $R^{25}$, $R^{26}$, $R^{27}$, and $R^{28}$ is independently selected from the group consisting of hydrogen, $C_{1-6}$alkyl, $C_{2-6}$alkenyl, $C_{2-6}$alkynyl, $C_{3-7}$carbocyclyl, $C_{6-10}$aryl, 5-10 membered heteroaryl, and 3-10 membered heterocyclyl.

23. The compound of claim 22, wherein $R^{21}$ is selected from the group consisting of C1-6alkyl, halo, cyano, hydroxyl, $C_{1-6}$alkoxy, halo $C_{1-6}$alkyl, halo $C_{1-6}$alkoxy, nitro, —C(=O)NR$^{22}$R$^{23}$, —N(R$^{24}$)C(=O)R$^{25}$, —C(=O)OR$^{26}$, —OC(=O)R$^{27}$, and —C(=O)R$^{28}$, and of $R^{22}$, $R^{23}$, $R^{24}$, $R^{25}$, $R^{26}$, $R^{27}$, and $R^{28}$ is independently selected from the group consisting of hydrogen, $C_{1-6}$alkyl, $C_{2-6}$alkenyl, $C_{2-6}$alkynyl, $C_{3-7}$carbocyclyl, $C_{6-10}$aryl, 5-10 membered heteroaryl, and 3-10 membered heterocyclyl.

24. The compound of claim 1, wherein $R^7$ is a phenyl.

25. The compound of claim 1, wherein $R^7$ is

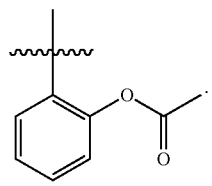 [SMILES: *c1ccccc1OC(C)=O]

26. The compound of claim 1, wherein R7 is a 5-18 membered heteroaryl optionally substituted with one or more $R^{29}$, wherein $R^{29}$ is selected from the group consisting of $C_{1-6}$alkyl, halo, cyano, hydroxy, $C_{1-6}$alkoxy, halo$C_{1-6}$alkyl, halo$C_{1-6}$alkoxy, nitro, —C(=O)NR$^{30}$R$^{31}$, —(R$^{32}$)C(=O)R$^{33}$, —C(=O)OR$^{34}$, —OC(=O)R$_{35}$, and —C(=O)R$^{36}$, and wherein each of $R^{30}$, $R^{31}$, $R^{32}$, $R^{33}$, $R^{34}$, $R^{35}$, and $R^{36}$ is independently selected from the group consisting of hydrogen, $C_{1-6}$alkyl, $C_{2-6}$alkenyl, $C_{2-6}$alkynyl, $C_{3-7}$carbocyclyl, $C_{6-10}$aryl, 5-10 membered heteroaryl, and 3-10 membered heterocyclyl.

27. The compound of claim 1, wherein $R^7$ is a 6 membered heteroaryl.

28. The compound of claim 1, wherein $R^7$ is

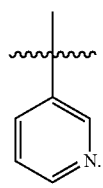 [SMILES: *c1cccnc1]

29. A compound selected from the group consisting of

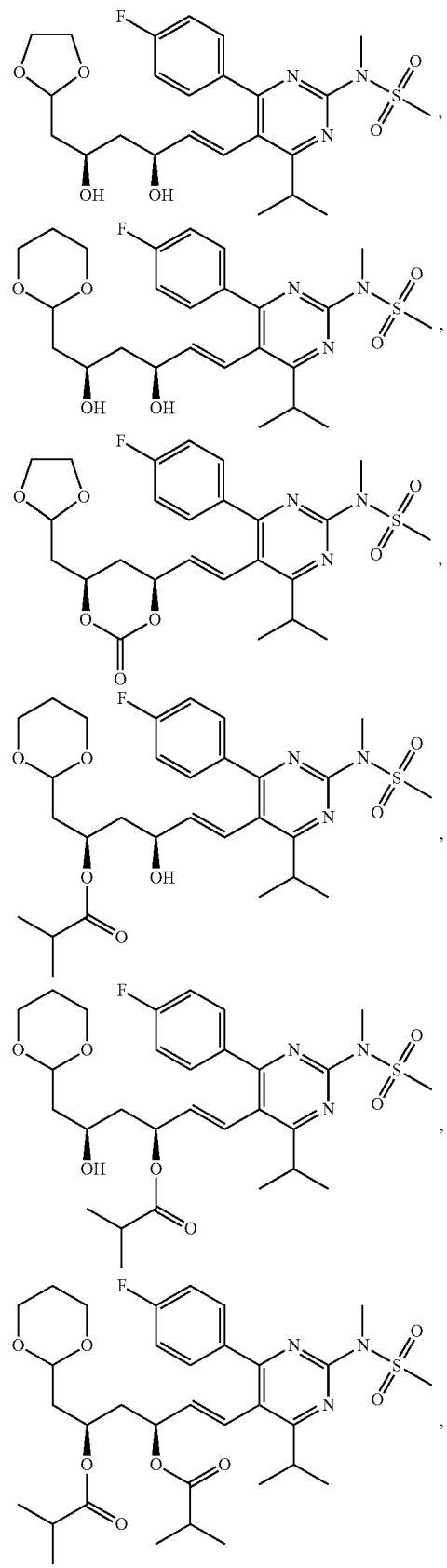

51
-continued
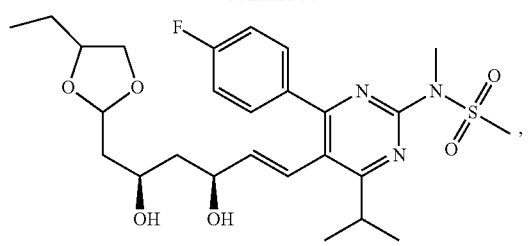
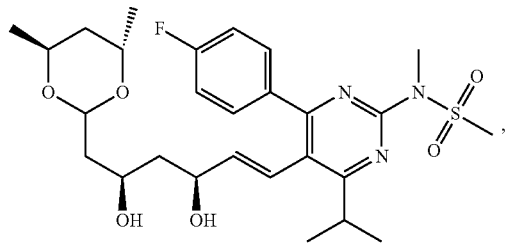
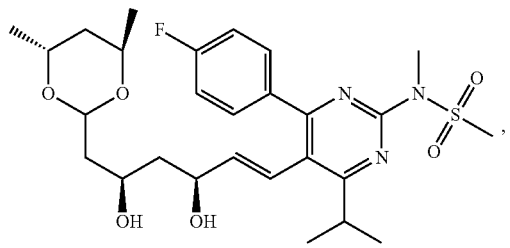
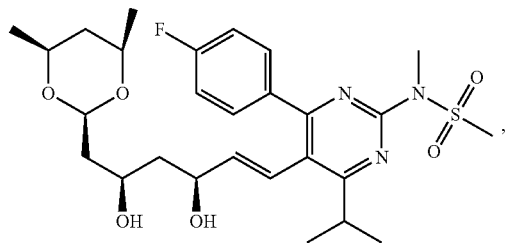
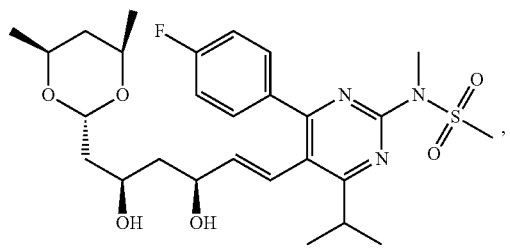
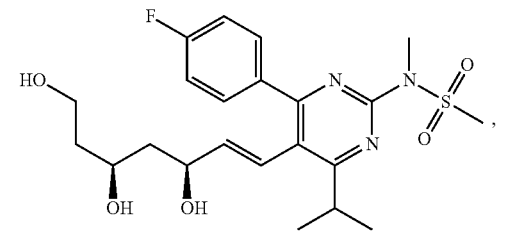
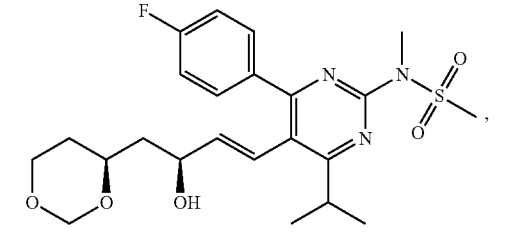
52
-continued
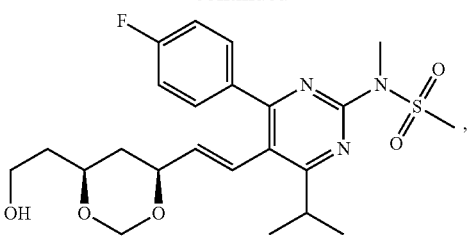
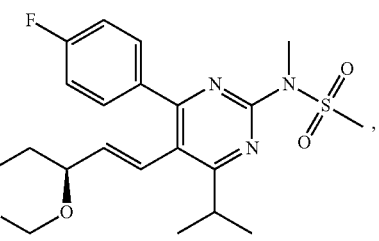
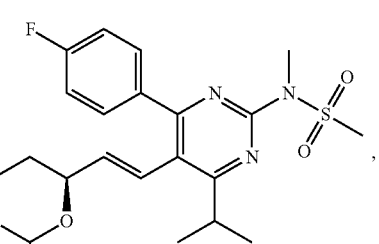
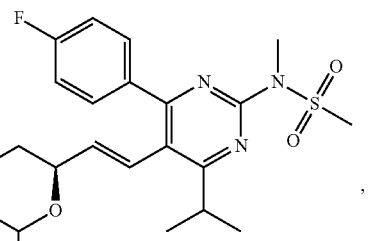
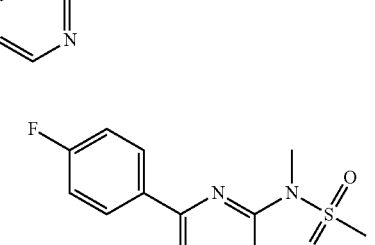
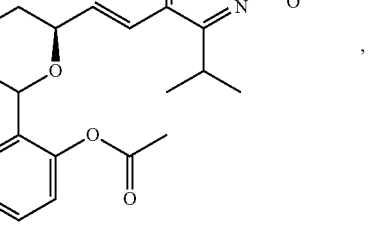

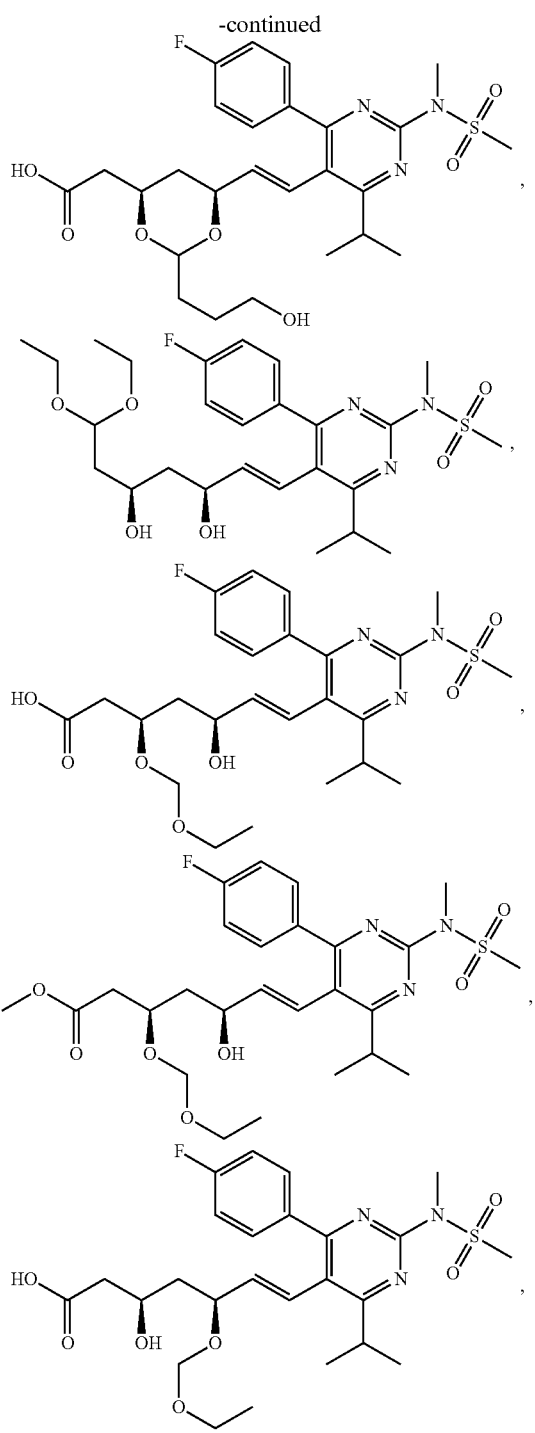
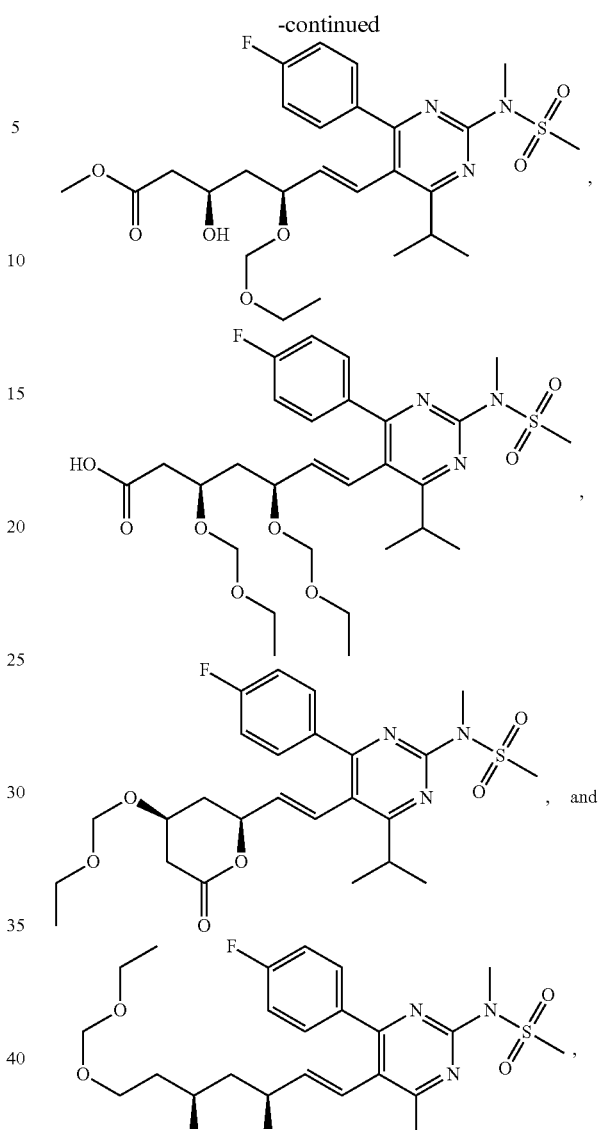
or pharmaceutically acceptable salts thereof.
30. A pharmaceutical composition comprising a therapeutically effective amount of a compound of claim 1, and a pharmaceutically acceptable excipient.
31. A method of inhibiting HMG-CoA reductase, comprising administering a compound of claim 1 to a subject in need thereof.
* * * * *